US007054823B1

(12) United States Patent
Briegs et al.

(10) Patent No.: US 7,054,823 B1
(45) Date of Patent: May 30, 2006

(54) CLINICAL TRIAL MANAGEMENT SYSTEM

(75) Inventors: Karen L. Briegs, Neshanic Station, NJ (US); David Detoro, Lebanon, NJ (US); Andrew Keim, Voorhees, NJ (US); Jean-Louis Saillot, Berkeley Heights, NJ (US)

(73) Assignee: Schering Corporation, Kenilworth, NJ (US)

( * ) Notice: Subject to any disclaimer, the term of this patent is extended or adjusted under 35 U.S.C. 154(b) by 880 days.

(21) Appl. No.: 09/655,667

(22) Filed: Sep. 6, 2000

Related U.S. Application Data

(60) Provisional application No. 60/153,344, filed on Sep. 10, 1999.

(51) Int. Cl.
*G06F 17/60* (2006.01)
(52) U.S. Cl. .................. 705/2; 705/3; 707/1; 715/700
(58) Field of Classification Search ................ 705/3, 705/2, 41, 29, 28; 600/300, 544; 707/9, 707/1, 10; 382/115
See application file for complete search history.

(56) References Cited

U.S. PATENT DOCUMENTS

| 5,694,469 | A | * | 12/1997 | Le Rue | ........................ | 705/51 |
| 5,732,401 | A | * | 3/1998 | Conway | ....................... | 705/29 |
| 5,734,883 | A | * | 3/1998 | Umen et al. | ................... | 707/1 |
| 5,737,539 | A | * | 4/1998 | Edelson et al. | ............... | 15/447 |
| 5,991,731 | A | * | 11/1999 | Colon et al. | .................... | 705/3 |
| 5,995,937 | A | * | 11/1999 | DeBusk et al. | ................ | 705/2 |
| 6,108,635 | A | * | 8/2000 | Herren et al. | .................. | 705/2 |
| 6,173,068 | B1 | * | 1/2001 | Prokoski | ..................... | 382/115 |

FOREIGN PATENT DOCUMENTS

WO  WO 9849647 A1 * 11/1998

OTHER PUBLICATIONS

Lamb, Kristen A. Bridging the Gap between Drug Discovery and Market. Introduction: The Rise of Contract Research Organizations. Feb. 2, 1998. [Retrieved on Jun. 2, 2003]. Retrieved from Internet. URL: <http://leda.law.harvard.edu/leda/data/203/klamb.pdf>.*

* cited by examiner

*Primary Examiner*—Joseph Thomas
*Assistant Examiner*—Natalie A. Pass

(57) ABSTRACT

A system for designing and monitoring clinical trials includes a main database of information concerning prior clinical trials and resources available to conduct future clinical trials. In part information in the main database is obtained through data links to other databases in the enterprise, e.g., human resources and finance databases. Some of the information in the main database concerns prior clinical trials and is, in part, in the form of protocols of (a) scheduled visits of a test subject to a treatment site, (b) measurement of prescribed physical attributes of the subject during the visits and (c) administration of at least one prescribed medical product to the subject during the visit to determine over time the subject's response thereto. The protocols of prior clinical trial are stored in the main database in the form of a software template.

40 Claims, 75 Drawing Sheets

FIG. 4

PROSIT – Never Never Land

File | Edit | View | Actions | Modules | Window | Help

| Protocol of Request ID | Number Req Submit Date | Protocol Site | Request Administration | Physician | Protocol Number | Protocol Title |
|---|---|---|---|---|---|---|
| RQ-0000001 | 01-MAR-199 | Country Administration | Design | Darling, Wendy | -000012 | Mometasone vs. Budesonide in Asth |
| RQ-0000002 | 26-MAR-199 | Pre-Study Visit | Study Planning | Darling, Wendy | -000065 | Mometasone vs. Budesonide in Asth |
| RQ-0000003 | 26-MAR-199 | Site Contact | Study Tracking | Darling, Wendy | | Comparative Study of Topical Cortic |
| RQ-0000004 | 26-MAR-199 | Laptop | | Darling, Wendy | | Effects of rHuL-10 on Cytochrome P |
| RQ-0000005 | 26-MAR-199 | Milestones | Pan, Peter J | Medicine, Cheif | | Absorption, Metabolism and Excreti |
| RQ-0000006 | 26-MAR-199 | Clinical Supplies | Pan, Peter J | Darling, Wendy | | Endometrial Histologic Effects of Or |
| RQ-0000007 | 26-MAR-199 | | Pan, Peter J | Medicine, Cheif | | Comparison of Mometasone Furoste |
| RQ-0000010 | 31-MAR-199 | | Pan, Peter J | Medicine, Cheif | -000112 | Comparison of Mometasone Furoste |
| RQ-0000079 | 08-APR-1998 | SUBMITTED Never Never Land | Pan, Peter J | Darling, Wendy | | Mometasone |
| RQ-0000080 | 03-APR-1998 | ASSIGNED Never Never Land | Pan, Peter J | Darling, Wendy | -P00008 | Mometasone vs. Budesonide In Asth |
| RQ-0000103 | 07-MAY-1998 | SUBMITTED Never Never Land | Pan, Peter J | Darling, Wendy | | nge ipgq3lkop3 |

FIG. 5

PROSIT – UNITED STATES

Protocol Number Request Details [New]

Request No:      Submit Date:      Status: NEW

Schering No:      Schering Name:

Requester: Rispoli, Marc C

Project Physician:

Program:

Mktd. Dose Form:

Project Accounting Code: - -

Monitoring Area:

Expense Center: 1477-RESEARCH SYS

Phase:

Protocol Type:

Working Title:

SPRI US IND:
International:

FIG. 6

PROSIT – UNITED STATES

Protocol Administration: I-P00324

Protocol: I-P00324 ▷ Schering No: 000049     Schering Name: ANTERON

Working Title: testing the new Prosit build version 1.04

Administration | Personnel | External Organizations

— Protocol Status —

Protocol Status: Amendment in Progress    Study Status: | PLANNED |    Active: ☑

Finalize Date: | 04-NOV-1998 |    Notification: ▷    Notif. Date: ▷

Notif. Reason:

— Administration/Accounting —

Therapeutic Team: ▷    Expense Center: 1477-RESEARCH SYS

Program: INTERNATIONAL ALLERGY    Mktd. Dose Form: ALKM SRINJ

Project Acct. Code: F01-000049-303E    Originating Sub: United States

Monitoring Area: MEDICAL AND SCIENTIFIC AFFAIRS    Amend. Version: 1    Event Manager: ☑

Protocol Type: I- MEDICAL RESEARCH INTERNATIO    Final Amend. Date:

PROSIT – Never Never Land

Protocol Design 000065

Protocol: -000065  Schering No. 032088  Schering Name: MOMETASONE
Working Title: Mometasone vs. Budesonide in Asthma

| Design | Medication | Visit Map | Procedures | Optional Fields | Subject Eligibility | Study Objectives |

Working Title: Mometasone vs. Budesonide in Asthma

Protocol Title: Efficacy and safety of mometasone furoate dry powder and budesonide powder (pulmicort turbuhaler) in the treatment of asthma Primary Indication: 493 Asthma    Phase: Phase III IND/HA Ref No:

Study Population: Adults

Data Collection Tool: CRF

Synopsis: Salbutamol MDI acceptable for reversibility

Secondary Indications:
4930 EXTRINSIC ASTHMA
4931 INTRINSIC ASTHMA

FIG. 9

PROSIT – Never Never Land

Protocol Design: -000065

Protocol: -000065 ▶ Schering No. 032088   Schering Name: MOMETASONE
Working Title: Mometasone vs. Budesonide in Asthma

| Design | Medication | Visit Map | Procedures | Optional Fields | Subject Eligibility | Study Objectives |

| Test Drug Number | Test Drug name | Role | Amendment |
|---|---|---|---|
| 032088 ▶ | MOMETASONE | PRIMARY ▶ | ▶ |
| ▶ | | | |

Test drug number can not be modified once saved, to change a test drug number delete it and re add it.

| Strength | Regimen | Dose Form | Route | Amendment ID |
|---|---|---|---|---|
| 100mcg | 2x daily | INHAL PWD ▶ | INTRANASAL ▶ | ▶ |
| 200mcg | 2 an 4x daily | INHAL PWD ▶ | INTRANASAL ▶ | ▶ |
| | | | | ▶ |

FIG. 10

PROSIT – Never Never Land

Protocol Design 000065

Protocol: -000065 ▸ Schering No. 032088  Schering Name: MOMETASONE
Working Title: Mometasone vs. Budesonide in Asthma

| Design | Medication | Visit Map | Procedures | Optional Fields | Subject Eligibility | Study Objectives |

| Visit ID | Visit Label | Study Phase | Prev. Visit ID | Days Since Prior Visit Min | Days Since Prior Visit Max | Enrollment Visit | Amendment ID |
|---|---|---|---|---|---|---|---|
| 1 | Test Recruitment | SCREENING ▸ |  | 0 | 0 | ☐ |  |
| 2 | Baseline | TREATMENT ▸ | 1 | 7 | 14 | ☐ |  |
| 3 | 1st Evaluation | TREATMENT ▸ | 2 | 5 | 9 | ☐ |  |
| 4 | 2nd Evaluation | TREATMENT ▸ | 3 | 5 | 9 | ☐ |  |
| 5 | Final Evaluation | FOLLOW UP ▸ | 4 | 25 | 31 | ☐ |  |
| 6 | 1st Evaluation Short | TREATMENT ▸ | 5 | 7 | 14 | ☐ |  |
| 7 | Final Evaluation Short | FOLLOW UP ▸ | 6 | 25 | 31 | ☐ |  |
| 8 |  |  | 7 |  |  | ☐ |  |

FIG. 12

PROSIT – Never Never Land

Protocol Design 000065

Protocol: -000065  Schering No. 032088  Schering Name: MOMETASONE
Working Title: Mometasone vs. Budesonide in Asthma

| Design | Medication | Visit Map | Procedures | Optional Fields | Subject Eligibility | Study Objectives |

Treatment Schedule: Treatment Schedule 1

| Procedure Name | Visit # > 1 | 2 | 3 | 4 | 5 |
|---|---|---|---|---|---|
| LABORATORY EVALUATION | ☑ | ☐ | ☐ | ☐ | ☐ |
| MEDICAL HISTORY | ☑ | ☐ | ☐ | ☐ | ☐ |
| VITAL SIGNS | ☑ | ☑ | ☑ | ☑ | ☑ |
| PHYSICAL EXAMINATION | ☐ | ☑ | ☐ | ☐ | ☑ |
| ECG | ☐ | ☐ | ☐ | ☐ | ☑ |

FIG. 13

PROSIT – Never Never Land

Protocol Design 000065

Protocol: -000065 ▸ Schering No. 032088    Schering Name: MOMETASONE
Working Title: Mometasone vs. Budesonide in Asthma

| Design | Medication | Visit Map | Procedures | Optional Fields | Subject Eligibility | Study Objectives |

| Subject Optional Field Name | Data Type |
|---|---|
| HEIGHT | Decimal ▸ |
| AGE ASTHMA ONSET | Integer ▸ |
| CONCOMITANT MED WASHOUT | Yes/No ▸ |
| | ▸ |

| Visit Optional Field Name | Date Type |
|---|---|
| ASTHMA SEVERITY | Integer ▸ |
| TREATMENT RESPONSE CORE | Integer ▸ |
| | ▸ |

FIG. 14

PROSIT – Never Never Land

Protocol Design P00008

Protocol: -P-00008  Schering No. 032088  Schering Name: MOMETASONE
Working Title: Mometasone vs. Budesonide in Asthma

| Design | Medication | Visit Map | Procedures | Optional Fields | Subject Eligibility | Study Objectives |

Reason for Ineligibility

- EXCLUDED CONCOMITANT MEDICATION
- DID NOT MEET ENTRANCE CRITERIA
- SUBJECT DID NOT WISH TO PARTICIPATE
- EXCLUDED CONCOMITANT ILLNESS

Reason for Discontinuation

| DID NOT MEET ENTRANCE CRITIERA | NC |
| DISEASE IS NOT SEVERE ENOUGH | DN |
| DISEASE IS TOO SEVERE | DS |
| EXCLUDED CONCOMITANT ILLNESS | EI |
| EXCLUDED CONCOMITANT MEDICATION | EM |
| HISTORY IS NOT APPROPRIATE FOR ENTRY | HN |
| RECENT EXCLUDED HOSPITALIZATION OR PROCEDURE | EH |
| SUBJECT AGE IS NOT APPROPRIATE | SA |
| SUBJECT DID NOT RETURN FOR SCREENING | SS |
| SUBJECT DIED PRIOR TO SCREENING | SD |

FIG. 15

PROSIT – Never Never Land

Protocol Design P00008

Protocol: -P-00008 ▸ Schering No. 032088    Schering Name: MOMETASONE
Working Title: Mometasone vs. Budesonide in Asthma

| Design | Medication | Visit Map | Procedures | Optional Fields | Subject Eligibility | Study Objectives |

Reason for Ineligibility
- EXCLUDED CONCOMITANT MEDICATION ▸
- PREGNANCY ▸
- DISEASE IS TOO SEVERE ▸

Reason for Discontinuation
- ADVERSE EVENT ▸
- PRE-ATRO ▸
- TREATMENT FAILURE, DX STATUS MOD/SEVERE ▸
- LOST TO FOLLOWUP ▸
- INVESTIGATOR DEEMS NOT IN SUBJECT'S INTEREST ▸
- NON-COMPLIANCE ▸
- DID NOT MEET PROTOCOL ELIGIBILITY ▸

| | |
|---|---|
| ADMINISTRATIVE | 70 |
| ADVERSE EVENT | 10 |
| CLEARED | 80 |
| COMPLETE | 00 |
| DEATH | 99 |
| DID NOT ENTER NEXT PHASE | 51 |
| DID NOT MEET CROSSOVER REQUIREMENTS | 64 |
| DID NOT MEET PROTOCOL ELIGIBILITY | 60 |
| DID NOT MEET PROTOCOL REQUIREMENTS | 63 |
| DID NOT MEET RANDOMIZATION CRITIERA | 65 |

FIG. 16

PROSIT -- Never Never Land

Protocol Design P00008

Protocol: -P-00008 ▶ Schering No. 032088  Schering Name: MOMETASONE
Working Title: Mometasone vs. Budesonide in Asthma

| Design | Medication | Visit Map | Procedures | Optional Fields | Subject Eligibility | Study Objectives |

Special Components

- EFFICACY
- BIOEQUIVALENCY

Design Considerations

- DOUBLE BLIND
- ACTIVE COMPARISON
- PARALLEL GROUP
- RANDOMIZED
- FOUR WAY CROSSOVER
- LATIN SQUARE
- NO TREATMENT CONTROL
- OPEN LABEL
- PARALLEL GROUP
- PLACEBO CONTROL
- PLACEBO WASHOUT
- RANDOMIZED
- SINGLE BLIND
- THREE WAY CROSSOVER

FIG. 17

PROSIT – UNITED STATES

File | Edit | View | Actions | Modules | Window | Help

Refresh
Finalize Protocol               Alt+R
Amend Protocol
Finalize Amendment
Event Manager
Amendment History Protocol Admi...
Protocol: I-P0...                          g Name: ANTERON
Working Title:

| Administration | Personnel | External Organizations |

Protocol Status
Protocol Status: Finalized          Study Status: Enrollment Ongoing          Active: ☑
Finalize Date: 12-MAR-19981998      Notification:                              Notif. Date:
Notif. Reason:

Administration/Accounting
Therapeutic Team: Allergy/Asthma (Allergy)    Expense Center: 834 Mgt Devel & Planning
Program: LINE EXTENSION ALLERGY               Mktd. Dose Form: Oral Powd-GMP
Project Acct. Code: C01-032088-123G           Originating Sub: United States
Monitoring Area: MARKETING                    Amend. Version:
Protocol Type: I- MEDICAL RESEARCH DOMESTIC   Final Amend. Date:          Event Manager: ☑

FIG. 18

PROSIT – UNITED STATES

Master Task List

| Seq | Task Name | Task Type | Task ID | Milestone |
|-----|-----------|-----------|---------|-----------|
| 1 | Completion of Clinical Program | SIMPLE | 50 | ✓ |
| 2 | Investigator Agreement Sent to HQ | SIMPLE | 23 | ✓ |
| 3 | Curriculum Vitae of Principal Investigators(s) | SIMPLE | 39 | ✓ |
| 4 | CV of Laboratory Director(s) Received in S | SIMPLE | 43 | ✓ |
| 5 | Informed Consent Task (Trans) | SIMPLE | 26 | ✓ |
| 6 | Gov. Regualtory App. (w/trans) Received in Sub | SIMPLE | 30 | ✓ |
| 7 | CV of Laboratory Director(s) Received in Sub | SIMPLE | 34 | ✓ |
| 8 | this is a new master task that was created by mark fung-a- | SIMPLE | 439 | ✓ |
| 9 | this is another very long task name that was created on the | SIMPLE | 441 | ✓ |
| 10 | Site Administration | SIMPLE | 447 | ✓ |
| 11 | Site Administration- Location/Personnel | SIMPLE | 448 | ✓ |
| 12 | Site Administration- Personnel and Location | SIMPLE | 457 | ✓ |
| 13 | Mark | SIMPLE | 482 | ✓ |
| 14 | Site Administration | SIMPLE | 499 | ✓ |
| 15 | First Data Discrepancy Report Available | SIMPLE | 529 | ✓ |
| 16 | Master Task Comm | SIMPLE | 569 | ✓ |
| 17 | First Subject/first Visit (Protocol) | SIMPLE | 570 | ✓ |
| 18 | Root | SIMPLE | 0 | |
| 19 | Design Start | SIMPLE | 48 | ✓ |
| 20 | Primary Stat Analysis Results Released | SIMPLE | 15 | ✓ |

| Rollup Task Name | Type | System ID |
|---|---|---|

FIG. 19

PROSIT – UNITED STATES

Core Task List

| Core Task List | Core Site Instructions | | | Milestone Indicator |
|---|---|---|---|---|
| Seq | Name | | Task Type Name | |
| 1 | Protocol Number Assigned | ▷ | EVENT MANAGER SIMPLE | ▷ |
| 2 | Final Protocol Date | ▷ | EVENT MANAGER SIMPLE | ▷ |
| 3 | Final CRF / RDE Screens Available | ▷ | SIMPLE | ▷ |
| 4 | First Site Initiated | ▷ | SUMMARY | ▷ |
| 5 | First Subject Enrolled (Protocol) | ▷ | SUMMARY | ▷ |
| 6 | First Subject / First Visit | ▷ | SUMMARY | ▷ |
| 7 | Enrollment Cutoff (Protocol) | ▷ | EVENT MANAGER SIMPLE | ▷ |
| 8 | Last Subject / Last Visit (Protocol) | ▷ | EVENT MANAGER SIMPLE | ▷ |
| 9 | Last CIVE / Data Discrepancy In-house. | ▷ | SIMPLE | ▷ |
| 10 | Data Cleanup Complete (Protocol) | ▷ | EVENT MANAGER SIMPLE | ▷ |
| 11 | Database Locked | ▷ | EVENT MANAGER SIMPLE | ▷ |
| 12 | Primary Stat Analysis Results Released | ▷ | SIMPLE | ▷ |
| 13 | Final Statistical Results Released | ▷ | SIMPLE | ▷ |
| 14 | Final Data Listins Released | ▷ | SIMPLE | ▷ |
| 15 | Final PCS Date | ▷ | SIMPLE | ▷ |
| 16 | Last Data In-house/SPRI HQ (Protocol) | ▷ | EVENT MANAGER SIMPLE | ▷ |
| 17 | Last Site Initiated (to Date) | ▷ | SUMMARY | |
| 18 | (New) | ▷ | | |

FIG. 20

PROSIT – UNITED STATES

| Core Task List | Core Site Instructions | | | | |
|---|---|---|---|---|---|
| Seq | Task Name | | Task Type Name | Milestone Indicator | TIA Indicator |
| 24 | Prestudy Visit Form(s) Received in Subsidary | ▷ | SIMPLE | ▷ | ▷ |
| 25 | Prestudy Visit Form(s) Sent to HQ | ▷ | SIMPLE | ▷ | ▷ |
| 26 | Protocol Signed by Investigator Rec. in Sub. | ▷ | SIMPLE | ▷ | ▷ |
| 27 | First Subject Enrolled (Site) | ▷ | AUTOMATIC ROLL-UP | ▷ | ▷ |
| 28 | Protocol Signed by Investigator Sent to HQ | ▷ | SIMPLE | ▷ | ▷ |
| 29 | Site Initiated | ▷ | AUTOMATIC ROLL-UP | ▷ | ▷ |
| 30 | First Subject Screened | ▷ | AUTOMATIC ROLL-UP | ▷ | ▷ |
| 31 | All Data In-house (Site) | ▷ | MANUAL ROLL-UP | ▷ | ▷ |
| 32 | Written Ethics Committee App. (w/trans) Sent | ▷ | SIMPLE | ▷ | ▷ |
| 33 | Written Ethics Committee App. (w/trans) Rec. | ▷ | SIMPLE | ▷ | ▷ |
| 34 | Data Clean-up Complete (Site) | ▷ | MANUAL ROLL-UP | ▷ | ▷ |
| 35 | Enrollment Complete (Site) | ▷ | MANUAL ROLL-UP | ▷ | ▷ |
| 36 | this is a new master task that was created by mark f | ▷ | SIMPLE | ▷ | ▷ |
| 37 | New Requirement | ▷ | SIMPLE | ▷ | ▷ |
| 38 | Site Administration-Personnel and Location | ▷ | SIMPLE | ▷ | ▷ |
| 39 | Site Administration | ▷ | SIMPLE | ▷ | ▷ |
| 40 | Site Administration | ▷ | SIMPLE | ▷ | ▷ |
| 41 | this is another very long task name that was created | ▷ | SIMPLE | ▷ | ▷ |
| 42 | Milestone task added to check the duration | ▷ | SIMPLE | ▷ | ▷ |
| 43 | A master task with the milestone indc | ▷ | SIMPLE | ▷ | ▷ |

FIG. 21

PROSIT – UNITED STATES

Template Tab Folder

Template: 1352    Changed: ☑    Country: UNITED STATES

Name: Template to test the milestone indc change

Template | Site Instructions

| Seq | Task Name | Days | Task Type Name | |
|---|---|---|---|---|
| 1 | USA-Template to test the molestone indc change | | USER DEFINED | |
| 2 | Protocol Number Assigned | 1 | EVENT MANAGERS | |
| 3 | Final Protocol Date | 0 | SIMPLE | |
| 4 | Final CRF / RDE Screen Date | 0 | SIMPLE | |
| 5 | First Site Initiated | 0 | SUMMARY | |
| 6 | First Subject / First Visit (Protocol) | 0 | SIMPLE | |
| 7 | Enrollment Complete (Protocol) | 0 | EVENT MANAGERS | |
| 8 | Last Subject / Last Visit (Protocol) | 0 | EVENT MANAGERS | |
| 9 | Data Cleanup Complete (Protocol) | 0 | EVENT MANAGERS | |
| 10 | Last Data Discrepancy Resolved | 0 | SIMPLE | |
| 11 | Database Locked | 0 | EVENT MANAGERS | |
| 12 | Primary Stat Analysis Results Released | 0 | SIMPLE | |
| 13 | Final Statistical Results Released | 0 | SIMPLE | |
| 14 | Final Data Listings Released | 1 | SIMPLE | |
| 15 | Final PCS Date | 0 | SIMPLE | |
| 16 | First Subject Enrolled | 0 | SUMMARY | |
| 17 | First Subject First Visit | 0 | SUMMARY | |
| 18 | Budget Info. Sheet (signed & dated by Inv.) Rec. | | SIMPLE | |

FIG. 22

PROSIT – Never Never Land

Study Planning

Protocol: A-P00216   Schering No: 032088   Schering Name: MOMETASONE

Country: Never Never Land   Plan Status: DRAFT   Plan Version: 0

| Protocol Projections | Study Planning | Site Instructions |

Select a Template

| Template Name | Template ID |
|---|---|
| Allergy | 693 |
| Anti-infectives | 695 |
| CNS | 697 |
| Cardiovascular | 696 |
| Core Task Template | 694 |
| Dermatology | 698 |
| Oncology | 699 |

[Select]   [Cancel]

FIG. 23

PROSIT – Never Never Land

Study Planning

Protocol: A-P00216  Schering No. 032088  Schering Name: MOMETASONE

Country: NEVER NEVER LAND  Plan Status: DRAFT  Plan Version: 0

| Protocol Projections | Study Planning | Site Instructions |

| | Planned | Latest Est. |
|---|---|---|
| Evaluable Subjects | 40 | |
| Subjects to Enroll | 50 | |
| Sites NEVER NEVER LAND | 2 | |
| Sites International | 0 | |
| Sites Per Monitor | 2 | |
| Sites Per HQ CRA | 0 | |
| Monitoring Interval wks | 6 | |
| Min No Subjects Per Site | 25 | |
| Average Subjects Per Site | 0 | |

Monitoring Countries  Planned  Latest Est.
NEVER NEVER LAND  0  0

Totals  0  0

FIG. 24

PROSIT – Never Never Land

Study Planning

Protocol: A-P00216 ▼  Schering No. 032088  Schering Name: MOMETASONE

Country: NEVER NEVER LAND ▼  Plan Status: DRAFT ▼  Plan Version: 0

| Protocol Projections | Study Planning | Site Instructions |

| Seq | Task Name | Latest Date | Actual Date | | | Latest | |
|-----|-----------|-------------|-------------|---|---|--------|---|
| 1 | AP00216 - NNL | 18-JUN-1998 | 18-JUN-1998 | 0 | 0 | 18-JUN-1998 | 18-JUN-1999 | 0 |
| 2 | Protocol Number Assigned | 18-JUN-1998 | 18-JUN-1998 | 0 | 0 | 18-JUN-1998 | 18-JUN-1998 | 0 |
| 3 | Protocol Approved | 00-000-0000 | 00-000-0000 | 0 | 0 | 00-000-0000 | 00-000-0000 | 0 |
| 4 | Investigators Identified | 00-000-0000 | 00-000-0000 | 1 | 0 | 00-000-0000 | 00-000-0000 | 1 |
| 5 | Pre-Study Visits Conducted | 00-000-0000 | 00-000-0000 | 0 | 0 | 00-000-0000 | 00-000-0000 | 0 |
| 6 | Last Pre-Study Visit Report | 00-000-0000 | 00-000-0000 | 0 | 0 | 00-000-0000 | 00-000-0000 | 0 |
| 7 | First Site Initiated | 00-000-0000 | 00-000-0000 | 0 | 0 | 00-000-0000 | 00-000-0000 | 0 |
| 8 | First Subject First Visit | 00-000-0000 | 00-000-0000 | 0 | 0 | 00-000-0000 | 00-000-0000 | 0 |
| 9 | Enrollment Complete (Protocol) | 00-000-0000 | 00-000-0000 | 0 | 0 | 00-000-0000 | 00-000-0000 | 0 |
| 10 | Last Subject / Last Visit (Protoc | 00-000-0000 | 00-000-0000 | 0 | 0 | 00-000-0008 | 00-000-0000 | 0 |
| 11 | All Data In house (Protocol) | 00-000-0000 | 00-000-0000 | 0 | 0 | 00-000-0000 | 00-000-0000 | 0 |
| 12 | Database Locked | 00-000-0000 | 00-000-0000 | 0 | 0 | 00-000-0000 | 00-000-0000 | 0 |
| 13 | Primary Stat Analysis Results | 00-000-0000 | 00-000-0000 | 0 | 0 | 00-000-0000 | 00-000-0000 | 0 |
| 14 | Protocol Analysis Final | 00-000-0000 | 00-000-0000 | 1 | 0 | 00-000-0000 | 00-000-0000 | 0 |
| 15 | CSR Approved | 00-000-0000 | 00-000-0000 | 0 | 0 | 00-000-0000 | 00-000-0000 | 0 |
| 16 | (New) | | | | | | | |

FIG. 25

PROSIT – Never Never Land

Study Planning

Protocol: P-P00124  Schering No. 000105  Schering Name: ESTRADIOL
Country: NEVER NEVER LAND  Plan Status: DRAFT  Plan Version: 0

Study Planning | Site Instructions | Protocol Projections | SMP Study Plan | SMP Site Instructions

| Seq | Task Name | Planned Start Dt | Planned End Dt | Planned | Planned Min Delay | Latest Start Dt | Latest End Dt | Latest Days | Latest Min Relay |
|---|---|---|---|---|---|---|---|---|---|
| 1 | PP00124 – USA | 12-AUG-1999 | 12-AUG-1999 | 0 | | 12-AUG-1999 | 12-AUG-1999 | 0 | |
| 2 | Protocol Number Assigned | 12-AUG-1999 | 12-AUG-1999 | 0 | | 12-AUG-1999 | 12-AUG-1999 | 0 | |
| 3 | Final Protocol Date | 00-000-0000 | 00-000-0000 | 0 | 0 | 00-000-0000 | 00-000-0000 | 0 | 0 |
| 4 | Final CRF/RDI Screens Available | 00-000-0000 | 00-000-0000 | 1 | 0 | 00-000-0000 | 00-000-0000 | 1 | 0 |
| 5 | First Site Initiated | 00-000-0000 | 00-000-0000 | 1 | 0 | 00-000-0000 | 00-000-0000 | 1 | 0 |
| 6 | First Subject Enrolled (Protocol) | 00-000-0000 | 00-000-0000 | 0 | 0 | 00-000-0000 | 00-000-0000 | 0 | 0 |
| 7 | First Subject First Visit | 00-000-0000 | 00-000-0000 | 0 | 0 | 00-000-0000 | 00-000-0000 | 0 | 0 |
| 8 | Enrollment Cutoff (Protocol) | 00-000-0000 | 00-000-0000 | 0 | 0 | 00-000-0000 | 00-000-0000 | 0 | 0 |
| 9 | Last Subject/Last Visit (Protocol) | 00-000-0000 | 00-000-0000 | 0 | 0 | 00-000-0000 | 00-000-0000 | 0 | 0 |
| 10 | Last CIVE/Data Discrepancy InHo | 00-000-0000 | 00-000-0000 | 0 | 0 | 00-000-0008 | 00-000-0000 | 0 | 0 |
| 11 | Data Cleanup Complete (Protoco | 00-000-0000 | 00-000-0000 | 0 | 0 | 00-000-0000 | 00-000-0000 | 0 | 0 |
| 12 | Database Locked | 00-000-0000 | 00-000-0000 | 0 | 0 | 00-000-0000 | 00-000-0000 | 0 | 0 |
| 13 | Primary Stat Analysis Results Re | 00-000-0000 | 00-000-0000 | 5 | 0 | 00-000-0000 | 00-000-0000 | 5 | 0 |
| 14 | Final Statistical Results Releas | 00-000-0000 | 00-000-0000 | 0 | 0 | 00-000-0000 | 00-000-0000 | 0 | 0 |
| 15 | Final Data Listings Released | 00-000-0000 | 00-000-0000 | 0 | 0 | 00-000-0000 | 00-000-0000 | 0 | 0 |

FIG. 28

PROSIT – Never Never Land

Site Number Request

| Request No | Submit Date | Status | Country | Prefix | Protocol | Site | Requester | Investigator | |
|---|---|---|---|---|---|---|---|---|---|
| RQ-10293 | 28-MAY-1998 | ASSIGNED | Never Never Land | Q | P00036 | 1 | Training, One | Investigator, One | Never Never Land |
| RQ-10294 | 28-MAY-1998 | ASSIGNED | Never Never Land | Q | P00036 | 2 | Training, Two | Investigator, Two | Never Never Land |
| RQ-10295 | 28-MAY-1998 | ASSIGNED | Never Never Land | Q | P00036 | 3 | Training, Three | Investigator, Three | Never Never Land |
| RQ-10296 | 28-MAY-1998 | ASSIGNED | Never Never Land | Q | P00036 | 4 | Training, Four | Investigator, Four | Never Never Land |
| RQ-10297 | 28-MAY-1998 | ASSIGNED | Never Never Land | Q | P00036 | 5 | Training, Five | Investigator, Five | Never Never Land |
| RQ-10298 | 28-MAY-1998 | ASSIGNED | Never Never Land | Q | P00036 | 6 | Training, Six | Investigator, Six | Never Never Land |
| RQ-10299 | 28-MAY-1998 | ASSIGNED | Never Never Land | Q | P00036 | 7 | Training, Seven | Investigator, Seven | Never Never Land |
| RQ-10300 | 28-MAY-1998 | ASSIGNED | Never Never Land | Q | P00036 | 8 | Training, Eight | Investigator, Eight | Never Never Land |
| RQ-10301 | 28-MAY-1998 | ASSIGNED | Never Never Land | Q | P00036 | 9 | Training, Nine | Investigator, Nine | Never Never Land |
| RQ-10302 | 28-MAY-1998 | ASSIGNED | Never Never Land | Q | P00036 | 10 | Training, Ten | Investigator, Ten | Never Never Land |
| RQ-10303 | 28-MAY-1998 | ASSIGNED | Never Never Land | Q | P00036 | 11 | Training, Eleven | Investigator, Eleven | Never Never Land |
| RQ-10304 | 28-MAY-1998 | ASSIGNED | Never Never Land | Q | P00036 | 12 | Training, Twelve | Investigator, Twelve | Never Never Land |
| RQ-10305 | 28-MAY-1998 | ASSIGNED | Never Never Land | Q | P00036 | 13 | Training, Thirteen | Investigator, Thirteen | Never Never Land |
| RQ-10306 | 28-MAY-1998 | ASSIGNED | Never Never Land | Q | P00036 | 14 | Training, Fourteen | Investigator, Fourteen | Never Never Land |
| RQ-11047 | 22-DEC-1998 | RETURNED | Never Never Land | Q | P00041 | 1 | Training, One | Hook, Captain | Never Never Land |
| RQ-11048 | 22-DEC-1998 | ASSIGNED | Never Never Land | Q | P00041 | 1 | Training, One | Hook, Captain | Never Never Land |
| RQ-11049 | 22-DEC-1998 | ASSIGNED | Never Never Land | Q | P00041 | 2 | Training, One | Bell, Tinker | Never Never Land |
| RQ-11050 | 22-DEC-1998 | RETURNED | Never Never Land | Q | P00041 | 2 | Training, One | Bell, Tinker | Never Never Land |
| RQ-11067 | 28-DEC-1998 | RETURNED | Never Never Land | B | P00100 | | Training, One | Investigator, Eight | Never Never Land |
| RQ-11068 | 28-DEC-1998 | RETURNED | Never Never Land | A | P00102 | | Training, One | Bell, Tinker | Never Never Land |
| RQ-11069 | 28-DEC-1998 | RETURNED | Never Never Land | A | P00102 | | Training, One | Bell, Tinker | Never Never Land |
| RQ-11070 | 28-DEC-1998 | RETURNED | Never Never Land | A | P00102 | | Training, One | Big Chief, Red | Never Never Land |
| RQ-11071 | 28-DEC-1998 | ASSIGNED | Never Never Land | A | P00102 | 1 | Training, One | Bell, Tinker | Never Never Land |
| RQ-11072 | 28-DEC-1998 | ASSIGNED | Never Never Land | A | P00102 | 2 | Training, One | Big Chief, Red | Never Never Land |

FIG. 29

PROSIT – Never Never Land – [Site Request Details (New)]

Request No:      Submit Date:      Status: NEW

Protocol: A-P00102

Requester: Training, Six

Investigator:

Location: Never Never Land

Site Number:

FIG. 30

PROSIT – UNITED STATES

Site Administration

Protocol: I-P00324  Schering No: 000049  Schering Name: ANTERON
Site No: 1  Investigator: Abdulhay, G  Country: UNITED STATES Site Administration | Post Study Eval.

Protocol
Study Status: PLANNED  Notification: RESUME STUDY
Notification Reason:

Site Status: PLANNED  Effective Amendment: 1
Data Collection Tool: CRF  Effective Date: 04-NOV-1998

Projected Enrollment
Req. Minimum: 0  Site Enrollment: 1

Budget
Procedure Level ○ Site Level ●

Prim. Location: YYY  Currency: U.S. DOLLARS
Pre-Study Visit:

| Name | Function | Phone | Fax | Local Inv. No |
| Abdulhay, G | PRINCIPAL INVESTIGATOR | | | |

FIG. 31

PROSIT – UNITED STATES

Site Administration

| | | | | |
|---|---|---|---|---|
| Protocol: | I-P00324 ▷ | Schering No: 000049 | Schering Name: | ANTERON |
| Site No: | 1 ▷ | Investigator: Abdulhay, G | Country: | UNITED STATES |

Site Administration | Post Study Eval.

Global Assessment: NOT RECOMMENDED ▷   Evaluated By: Rispoli, Marc C ▷

Evaluated On: 12-NOV-1998

| | | | | |
|---|---|---|---|---|
| ADEQUACY OF PATIENT SOURCE | GOOD ▷ | DRUG STORAGE AREA | ADEQUATE ▷ |
| FACILITIES | GOOD ▷ | LABORATORY | VERY GOOD ▷ |
| PRINCIPAL/CO-PRINCIPAL INVESTIGAT | VERY GOOD ▷ | PI'S TIME TO CONDUCT/SUPE | VERY GOOD ▷ |
| STUDY STAFF | VERY GOOD ▷ | SUB INVESTIGATOR(S) | VERY GOOD ▷ |

FIG. 32

PROSIT – UNITED STATES

Site Personnel & Locations

Protocol: 1-P00324  Schering No: 000049  Schering Name: ANTERON
Site No: 1  Investigator: Abdulhay, G  Country: UNITED STATES Locations | SP Personnel | Non SP Personnel | Non SP Personnel Locations

| Active | Primary | Location | Role | Country | Address |
|---|---|---|---|---|---|
| ☑ | ☐ | HELSINGIN YUOPPIST | (CO)SPONS | FINLAND | KESKUSSAIRAALA MEILAHDENTI |
| ☑ | ☐ | 3V45 HSC MCMASTER | CENTRAL IR | CANADA | This is address line 1 for external organization printing 123456 |
| ☑ | ☐ | 410-2000 CREDIT VALL | CONTRACTI | CANADA | |
| ☑ | ☐ | SCICOR, INC. | CENTRAL IR | UNITED STATES | 8211 SCICOR DRIVE MISSISSAUGA |
| ☑ | ☐ | KENILWORTH | CENTRAL IR | UNITED STATES | ADDRESS |
| ☑ | ☑ | YYYY | CENTRAL L | CANADA | YYYY |
| ☑ | ☐ | | | | |

FIG. 33

PROSIT – UNITED STATES

Site Personnel & Locations

Protocol: I-P00324  Schering No: 000049  Schering Name: ANTERON
Site No: 1  Investigator: Abdulhay, G  Country: UNITED STATES Locations | SP Personnel | Non SP Personnel | Non SP Personnel Locations

| Active | Write | Employee | Responsibility | Active Date | Inactive Date | Country | Expense |
|---|---|---|---|---|---|---|---|
| ✓ | ✓ | Rispoli, Marc C | SITE REQUESTER | 03-NOV-1998 | 00--0000 | USA | RESEARC |
| ✓ | ✓ | Lee, J S | Clinical Data Coordi | 12-NOV-1998 | 00--0000 | USA | CHEM PR |
| ✓ |   |   |   | 05-JAN-1999 | 00--0000 |   |   |

FIG. 34

PROSIT -- UNITED STATES

Site Personnel & Locations

Protocol: I-P00324　　Schering No: 000049　　Schering Name: ANTERON
Site No: 1　　Investigator: Abdulhay, G　　Country: UNITED STATES Locations | SP Personnel | Non SP Personnel | Non SP Personnel Locations

| Active | Person | Responsibility | Active Date | Inactive Date | Country | Phone No. |
|---|---|---|---|---|---|---|
| ☐ | Aapro, Mary S | Principal Investigator | 03-NOV-1998 | 03-NOV-1998 | U.S. VI | 908-603-3952 |
| ☑ | Aarons-You Ok AL | Data Entry Clerk/Data C | 04-NOV-1998 | 04-NOV-1998 | U.S.A. | |
| ☑ | Abdulhay, G | Principal Investigator | 04-NOV-1998 | 04-NOV-1998 | U.S.A. | 234-243-1234 |
| ☑ | Aaronson, AL | Dietician | 12-NOV-1998 | 12-NOV-1998 | U.S.A. | |
| ☑ | Aaronson, D | Hospital Administrator | 12-NOV-1998 | 12-NOV-1998 | SAMOA | |
| ☑ | 656566, 67777 76 | Contract/Grant Administr | 12-NOV-1998 | 12-NOV-1998 | U.S.A. | 1234 |
| ☑ | Abbamont, T | IRB Chairman | 05-JAN-1999 | 05-JAN-1999 | | |

FIG. 35

PROSIT – UNITED STATES

Site Personnel & Locations

Protocol: I-P00324  Schering No: 000049  Schering Name: ANTERON
Site No: 1  Investigator: Abdulhay, G  Country: UNITED STATES Locations | SP Personnel | Non SP Personnel Associated Site Personnel: Aaronson, D   Non SP Personnel Locations

| Primary | Location | Role | Country | Address | City |
|---|---|---|---|---|---|
|  | SCICOR, INC. | CENTRAL IRB/EC | USA | 8211 SCICOR DRIVE | IND |
|  | YYYY | CENTRAL LABORATORY | CAN | YYYY | YY |
|  | 410-2000 CREDIT VALL | CONTRACT RESEARCH ORG. | CAN | MISSISSAUGA | ON |
|  | 3V45 HSC MCMASTER | CENTRAL IRB/EC | CAN | This is address line 1 for external organization printing 123456 | HAI |
| ✓ | HELSINGIN YUOPISTO | (CO)SPONSORING ORG. | FIN | KESKUSSAIRAALA MEILAHDENTIE2 002 |  |
|  | KENILWORTH | CENTRAL IRB/EC | USA | ADDRESS | City |
|  |  |  |  |  |  |

FIG. 36

PROSIT – UNITED STATES

Site Study Tracking

Protocol: 1-P00324 ▼  Schering No: 000049  Schering Name: ANTERON

Country: UNITED STATES ▼  Site No: 1 ▼  INVESTIGATOR: Abdulhay, G ▼

| Seq | Task Name | Latest Date | Actual Date | |
|---|---|---|---|---|
| 1 | 1P00324- USA | | | |
| 2 | Completed Grant Request Form Received in Sub. | 00-000-0000 | 02-NOV-1998 | ☐ |
| 3 | CV of Laboratory Director(s) Received in S | 00-000-0000 | 00-000-0000 | ☐ |
| 4 | Budget Info Sheet (signed & dated by Inv.) Rec. | 00-000-0000 | 00-000-0000 | ☐ |
| 5 | CV of Laboratory Director(s) Received in Sub. | 00-000-0000 | 00-000-0000 | ☐ |
| 6 | CV of Laboratory Director(s) Sent to HQ | 00-000-0000 | 00-000-0000 | ☐ |
| 7 | Completed Grant Request Form Sent to HQ | 00-000-0000 | 00-000-0000 | ☐ |
| 8 | Curriculum Vitae of Principal Inv.(s) Rec. in | 00-000-0000 | 00-000-0000 | ☐ |
| 9 | Curriculum Vitae of Principal Investigators | 00-000-0000 | 00-000-0000 | ☐ |
| 10 | Curriculum Vitae of Sub-Inv.(s) Received in S | 00-000-0000 | 00-000-0000 | ☐ |
| 11 | Curriculum Vitae of Subinvestigator(s) Sent t | 00-000-0000 | 00-000-0000 | ☐ |
| 12 | Doc. Of Quality Control Proc. Or Cert. Rec. in | 00-000-0000 | 00-000-0000 | ☐ |
| 13 | Doc. Of Quality Control Proc. Or Cert. Sent to | 00-000-0000 | 00-000-0000 | ☐ |
| 14 | FDA Form 1572 Received in Sub. | 00-000-0000 | 00-000-0000 | ☐ |
| 15 | FDA Form 1572 Sent to HQ | 00-000-0000 | 00-000-0000 | ☐ |
| 16 | Gov. Regulatory App. (w/trans.) Sent to HQ. | 00-000-0000 | 00-000-0000 | ☐ |
| 17 | Gov. Regulatory App. (w/trans.) Received in S | 00-000-0000 | 00-000-0000 | ☐ |
| 18 | Informed Consent Task (Trans) | 00-000-0000 | 00-000-0000 | ☐ |
| 19 | Informed Consent Doc. (with translation) Sent | 00-000-0000 | 00-000-0000 | ☐ |
| 20 | Site Closed | 00-000-0000 | 00-000-0000 | ☐ |

FIG. 37

PROSIT – UNITED STATES

Site Budget

Protocol: I-P00324　　Schering No: 000049　　Schering Name: ANTERON

Site No: 1　　Investigator : Abdulhay,G.　　Currency: U.S. Dollars　　Revision:

| Administration | Site Payees | Site Budget | Subject Costs |

Status:

Amendment:

Submit Date: 00--0000

Effective Date: 00--0000

Overhead Percent: 0.00

FIG. 38

PROSIT – UNITED STATES

Site Budget

Protocol: [I-P00324]  Schering No: 000049  Schering Name: ANTERON

Site No: [1]  Investigator: Abdulhay, G.  Currency: U.S. Dollars  Revision:

| Administration | Site Payees | Site Budget | Subject Costs |

Local Payee  Global Payee  Finance Code

[10th SYMPOSIUM MOLECULAR]

FIG. 39

PROSIT – Never Never land

Site Budget

Protocol: A-P00102   Schering No: 000001   Schering Name: STEROIDS FOR SKIN TESTS
Site No: 4   Investigator: Big Chief, Red   Currency: GOURDE   Revision: 1

Administration | Site Payees | Site Budget | Subject Costs

Protocol: P00102   Site No 4   Revision: 1-IN Revision   Effective Date:   Amendment:

| Line Item | OH | Default Payee | Unit Cost | Units | Total |
|---|---|---|---|---|---|
| SUBJECT COSTS | | | | | |
| PROCEDURE COSTS | | | | | |
| Laboratory Evaluation | ☐ | Captain Hook | 10.00 | 5 | 50.00 |
| Medical History | ☑ | | 100.00 | 2 | 200.00 |
| | ☑ | | .00 | | |
| ADDITIONAL VISIT COSTS | | | | | |
| Evaluation | ☐ | 10th SYMPOSIL | 100.00 | 3 | 300.00 |
| | ☐ | | .00 | | |
| ADJUSTMENTS | | | | | |
| Recovery | ☐ | | 100.00 | 2 | 200.00 |
| | ☐ | | .00 | | |
| OTHER COSTS | | | | | |
| Advertisement | ☐ | 10th SYMPOSIL | 100.00 | 2 | 200.00 |
| Discovery | ☐ | Captain Hook | 20.00 | 3 | 60.00 |
| TOTAL BUDGET | | | | | 1,060.00 |
| PREVIOUSLY APPROVED | | | | | |

REQUIRED

FIG. 40

PROSIT – UNITED STATES

Site Budget

Protocol: I-P00324  Schering No: 000049  Schering Name: ANTERON

Site No: 1  Investigator: Abdulhay, G  Currency: U.S. DOLLARS  Revision

| Administration | Site Payees | Site Budget | Subject Costs |

Treatment Schedule: Treatment Schedule 1

| Line Item | Visit # > Subjects Budgeted > | 1 | 2 | 3 |
|---|---|---|---|---|
| 13C-UREA BREATH TEST | | $.00 | $.00 | $.00 |
| 12-LEAD ECG | | $.00 | $.00 | $.00 |
| 2-VIEW XRAY | | $.00 | $.00 | $.00 |
| 24-HOUR URINE COLLECTION | | $.00 | $.00 | $.00 |
| 4-VIEW XRAY | | $.00 | $.00 | $.00 |

FIG. 41

PROSIT – UNITED STATES

Pre-Study Visit

Protocol: I-P00324　　Schering No: 000049　　Schering Name: ANTERON
Pre-Study Visit No.: 10566　　Principal Investigator: Abdulhay, G　　Country: NORWAY

| Pre-Study Visit | SP Personnel | NSP Personnel | Discussion Items | Evaluation |

Potential Investigator: Aasebo, U　　Potential Investigator: Location Name

Country: AFGHANISTAN

Visit Date: 18-NOV-1998　　Time: 16:25　　Finalized: 00- -0000

Schering Participants:
Rispoli, Marc C

Investigator Site Participants: Non-Registered( )
Aasebo, U

FIG. 42

PROSIT – UNITED STATES

Pre-Study Visit

Protocol: I-P00324 ▽   Schering No: 000049   Schering Name: ANTERON
Pre-Study Visit No.: 10566 ▽   Principal Investigator: Abdulhay, G   Country: NORWAY

| Pre-Study Visit | SP Personnel | NSP Personnel | Discussion Items | Evaluation |

Registered Site Personnel

| | Title |
|---|---|
| Aasebo, U ▷ | |
| ▷ | |

Non-Registered Site Personnel

| Last Name | First Name | Title |
|---|---|---|
| | | |

FIG. 43

PROSIT – UNITED STATES

Pre-Study Visit

Protocol: [1-P00324]  Schering No: 000049   Schering Name: ANTERON
Pre-Study
Visit No. [10566]  Principal Investigator: Aasebo, U    Country: NORWAY Pre-Study Visit | SP Personnel | NSP Personnel | Discussion Items | Evaluation

STUDY CONSIDERATIONS

- ☑ Pre Clinical Data
- ☑ Clinical Data
- ☑ Investigator Brochure
- ☑ Protocol
- ☑ Case Report Forms
- ☑ Monitoring Responsibilities
- ☑ Study Schedule
- ☑ Principal Investigator Responsibilities
- ☑ Sub-Investigator Responsibilities
- ☑ Staff Responsibilites
- ☑ Grant
- ☑ Payment Schedule

ETHICAL CONSIDERATIONS

- ☑ Cirriculum Vitae
- ☑ Principal Investigator
- ☑ Co-Principal Investigator
- ☑ Sub-Investigator
- ☑ Lab Director
- ☑ Laboratory Certification
- ☑ Laboratory Q.C. Procedures
- ☑ Laboratory Reference Ranges
- ☑ DEA Regulations and Drug Control
- ☑ Adequecy and Accuracy of Records
- ☑ Availability of Patient Records
- ☑ Drug Accountability and Disposition

- ☑ IRB/EC
- ☑ Approval Documents
- ☑ Responsibilities
- ☑ Retention of Records
- ☑ Informed Consent
- ☑ FDA 1572 OR
- ☑ Investigator Agreement
- ☑ Nature of FDA Inspection

FIG. 44

PROSIT – UNITED STATES

Pre-Study Visit

Protocol: 1-P00324  Schering No: 000049  Schering Name: ANTERON
Pre-Study Visit No.: 10566  Principal Investigator: Aasebo, U  Country: NORWAY

| Pre-Study Visit | SP Personnel | NSP Personnel | Discussion Items | Evaluation |

Global Assessment: RECOMMENDED

ADEQUACY OF PATIENT SOURCE: GOOD   DRUG STORAGE AREA:
FACILITIES:                        LABORATORY:
PRINCIPAL INVESTIGATOR / PRINCI    PI'S TIME TO CONDUCT/SUPERVISE: VERY GOOD
STUDY STAFF:                       SUB INVESTIGATORS:

FIG. 45

PROSIT – United States

Visit Contact

Protocol: I-P00324　　Site No: 1　　Schering No: 000049　　Schering Name: ANTERON
Contact: 00011286 - 04 –Nov-1998 unfinalized

| Visit Contact | Discussion Items |

Contact Information
Originator: Rispoli, Marc C　　Reason: CLINICAL STUDY SUPPLIES
Date: 04-Nov-1998　　Time: 00:00

Meeting Location
○ Site Roster:
● Other: testing the new prosit 1.03.1 build

Recommendation
The investigator site is:　● Recommended　　○ Not Recommended

Schering Participants
Rispoli, Marc C

Non-Schering Participants
Aapro, Mary S

PROSIT – United States

Visit Contact

Protocol: 1-P00324  Schering No: 000049  Schering Name: ANTERON

Site No: 1  Contact: 00011286 - 04 – Nov -1998 unfinalized

| Visit Contact | Discussion Items |

New Pre-Clinical or Clinical Data
- ☐ Efficacy
- ☐ Adverse Events

Protocol Adherence
- ☐ Subject Selection
- ☐ Conduct of Study
- ☐ Adverse Events
- ☐ Concomittant Medications

Case Report Form (CRF) Records
- ☐ CRF Completion vs. Patient Enrollment
- ☐ CRF Completeness
- ☐ CRF Availability, Storage and Retention

Personnel Responsibilities
- ☐ Principal Investigator
- ☐ Sub-Investigator
- ☐ Staff

Facilities
- ☐ Location of Patient Info.
- ☐ Clinical Laboratory
- ☐ Equipment
- ☐ Other

Clinical Supplies
- ☐ Quantity
- ☐ Storage
- ☐ Dispensing
- ☐ Packaging/Labeling/Coding
- ☐ Randomization
- ☐ Recertification Date
- ☐ Drug Disclosure Envelopes
- ☐ Documentation of Accountability

Monitoring Activities
- \* ☐ Action taken by P1 and Monitor to correct deficiency
- \* ☐ Source Document Verification Completed
- \* ☐ Consents Reviewed
- \* ☐ Source Document Checked \* Required to finalize the site contact

FIG. 48a

PROSIT – UNITED STATES

Site Tracking

Protocol: [ I-P00324 ▽ ]   Schering No: 000049   Schering Name: ANTERON

Site: [ 1 ]   Contact: 11286   Visit Unfinalized   As of: [ 04-Nov-1998 ▽ ]

| Enrollment Tracking | Ineligible For Screening |

| | Enrollment as of Unfinalized Site Visit | Enrollment as of Finalized Visit |
|---|---|---|
| Potential Subjects Ineligible for Screening: | 2 | |
| Number of Subjects Screened: | 10 | 0 |
| Number of Subjects Failed Screening: | 2 | 0 |
| Number of Subjects Enrolled: | 8 | 1 |
| Number of Subjects Discontinued Total: | 2 | 0 |
|    Adverse Events: | 1 | 0 |
|    Other: | 1 | 0 |
| Number of Subjects Complete: | 5 | 0 |
| Number of Subjects Ongoing: | 1 | 0 |

FIG. 48b

PROSIT – Never Never Land

Site Tracking

Protocol: 000065   Schering No: 032088   Schering Name: MOMETASONE
Site: 1   Contact: 2856   Telephone  Unfinalized   As of: 30-Mar-1998

Enrollment Tracking | Ineligible For Screening

| | Number of Subjects as of 30-Mar-98 | Percent of Site Total |
|---|---|---|
| Site Total: | 1 | |
| Reason For Ineligibility | | |
| PREGNANCY | 1 | 100.0 |
| EXCLUDED CONCOMITANT MEDICATION | 0 | 0.0 |
| DISEASE IS TOO SEVERE | 1 | 100.0 |

FIG. 49

PROSIT – UNITED STATES

Subject Visit Tracking

Protocol: 1-P00324   Site No: 1   Contact: 11286   Initials: [ ]

Screening Number: 1   Subject Number: 3

Subject | Visit Summary | Discount | Unsched | 2 | 1

Gender: MALE   Date of Birth: 01-Jan-1971   Age at Enrollment: 27 Years   Discontinuation Visit Signed Consent: 02-Nov-1998   Last Visit Number: 0

Enrollment: 09-Nov-1998   Current Phase: MAINTENANCE

Therapy Started: 00--0000   Complete: [ ]   Useable/Evaluable: [ ]

Therapy Ended: 00--0000   Reason For Discontinuation:

Days On Therapy:   Discontinuation Date: 30-Nov-1998

Additional Subject Date:

SUBJECT 1:

FIG. 50

PROSIT – UNITED STATES

Subject Visit Tracking

Protocol: I-P00324  Site No: 1  Contact: 11286

Screening Number: 1  Subject Number: 3  Initials:

| Subject | Visit Summary | Discount | Unsched | 2 | 1 |

| Visit No | Amendment | Visit Label | Visit Date | Delta | To Do | CRF Status | SDV Status |
|---|---|---|---|---|---|---|---|
| 1 | | Visit 1 | 09-Nov-1998 | | ☐ | COLLECTED | <100% |
| 2 | | Visit 2 | 16-Nov-1998 | 6 | ☐ | PARTIALLY COLLECTED | <100% |
| 3 | | Unscheduled Visit | 23-Nov-1998 | | ☑ | PARTIALLY COLLECTED | |
| 4 | | Discontinued Visit | 30-Nov-1998 | | ☑ | NOT COLLECTED | |

Ready                                                                 05-Jan-1999

FIG. 51

PROSIT – UNITED STATES

Formulated Materials Requisition

FMR Req. ID: 184

Administration | Materials

Protocol Information
Protocol Number: A-P00240    Schering No: 000028    A AND D

|  |  |  | Marketed |
| --- | --- | --- | --- |
| Program Code: | F05 | Schering No: 000028 | Dose Form: Bolus |
| Expense Center: | 1495-WORLDWIDE RSCH QA | | |
| Requisition Source: | ANIMAL HEALTH DOMESTIC/INTERNATIONAL | | |
| Requested by: | Desontos, Marc | | |
| Authorized by: | Desontos, Marc | | |

Date Required For Packaging: 22-Dec-1998    Blinding Required: ☐

Special Directions and Blinding (explain blinding requirements if any):

FIG. 52

PROSIT – UNITED STATES

PSR Request: Protocol Packaging

Protocol: I-P00324　Schering No: 000049　Schering Name: ANTERON

Country: UNITED STATES　PSR No: 1489

| PSR Information | Components | Ship To |

Project Accounting Code: F01 – 000049 – 303E　Exp Center: 1477 RESEARCH SYS

New Protocol / Site: ☐　Study Type: ⊙ Blind　○ Open

Special Instructions:

Study Monitor: Grint, P C

Random Code Format: CODE ENVELOPES

Requested by: Rispoli, Marc C

Authorized by: 3,3

Required Ship Date: 31-Mar-1999

IND Labeling Date: 00--0000

Attachments:
PROTOCOL: ☐
LABEL FORMAT: ☐
LABELING INSTRUCTIONS: ☐
DEA FORM 222C: ☐
CONFIRMATION DEA REG: ☐

Random Code
Generation ID: _____　Select Sites:

FIG. 53

PROSIT – UNITED STATES

PSR Request: Protocol Packaging

Protocol: C-C98005   Schering No: 032088   Schering Name: MOMETASONE

Country: UNITED STATES   PSR No 1606

PSR Information | Components | Ship To

| Schering No: | Schering Name | Test Dose Form | Strength/Concentration | Package Description | Required Units |
|---|---|---|---|---|---|
| 032088 | MOMETASONE | ORAL AERPR | UNKNOWN | | |

FIG. 54

PROSIT – UNITED STATES

PSR Request: Protocol Packaging

Protocol: [I-P00324 ▽]  Schering No: 000049   Schering Name: ANTERON

Country: [UNITED STATES ▽]   PSR No [1489 ▽]

PSR Information | Components | Ship To |

Location: [SCHERING CANADA INC.] [▽]

Address: [170 ONEIDA STREET]

City: [POINTE CLAIRE]   US State / Other: [ ]

Postal Code: [H9R 1B4]   Country: [CANADA]

Phone: [ ]   Fax: [514 426 7300]

Attention: [ ]

FIG. 55

PROSIT – UNITED STATES

Material Transfer Request

Protocol: [C-P98615 ▽]  Schering No: 034117  Schering Name: DESLORATADINE

Country: [UNITED STATES ▽]  Site No: [1 ▽]  MTR No: [ ▽ ]

MTR Details | Ship To

Inventory Location: [          ▽]  Requested Ship Date: [00--0000]

Requested By: [Caprio, Denise M ▽]

Authorized By: [          ▽]  Intended Use Of Material: [☑]

Expense Center: 1751 SR DIR INTL CLIN RES

| Material Type | Batch No. | PSR No. | FMR No. | Quantity On Hand |
|---|---|---|---|---|
| [ ▽] | [ ▽] | [ ▽] | [ ▽] | _____ |

FIG. 56

PROSIT – UNITED STATES

Material Transfer Request

Protocol: C-P98615  Schering No: 034117  Schering Name: DESLORATADINE

Country: UNITED STATES  Site No: 1  MTR No: AA000637

MTR Details | Ship To

Location:
Address:
City:  State/Province:
Postal Code:  Country:
Phone:  Fax:
Attention:
Shipping/Packaging Instructions:

FIG. 57

PROSIT – UNITED STATES

Random Code Request - New

Protocol: Q-P00759   Schering No: 032088   Schering Name: MOMETASONE

Random Code Req ID:   Date Prepared: 00--0000   Ptcl Finalization Date: 21-Jul-1999

To:

From: Caprio, Denise, M

Random Code Type:

Generate Random Code by: 00--0000   Copies:

Number of United States Sites: 2   Random Code Generation ID:

Number of International Sites:   First United States Site ID: 1

Subjects Randomized by:   First International Site ID: 1

Subjects Replaced by:

Subject nbr assigned by:   Treatment Arm   Subjects   Comments:

Number of Stratification:   Total Subjects: 0

FIG. 58

PROSIT – United States

Check Control

Unsend: RENOWSKIG ▷    Renowski , George

Check Out )

Date: 13-Jul-1999   Extra Items ☐   Status: Checked out data available

| Protocol | Site | Primary Location | Site Investigator | Site Requestor |
|---|---|---|---|---|
| B93214 ▷ | ▷ | No Site – Ptcl only | | |
| B94055. ▷ | ▷ | No Site – Ptcl only | | |
| B94056. ▷ | ▷ | No Site – Ptcl only | | |

| Request Date | Status | Check In Date | Checked In Date | Reply from Server |
|---|---|---|---|---|

FIG. 59

PROSIT – Never Never Land

Subject Detail Report

PROSIT – SUBJECT DETAIL REPORT

| Schering No. | Working Study Title | | Protocol No.-Site No. |
|---|---|---|---|
| 032088 MOMETASONE | retesting the 110 visit map id st | | H000017 |
| Principal Investigator | Study Location | | Monitor |
| Daniel W Aaronson, MD | ifhdghdghdghcffghdfhdfhdf, USA | | |

SUBJECT: 6001/KM/1
Gender: M          Last Visit Date:   09-APR-1998    Reason for Discontinuation
Age: 30 years      Last Visit Label:  Visit 3
Date of Birth: 07-Aug-1967    Tx Started:
Signed Consent:    Tx Stopped:
Evaluable:         Days on Tx (to date):

As of: 05-MAR-1998    Contact ID: 6038

| Visit | Date (Delta) | SDY | CRF Status | Pages Collected |
|---|---|---|---|---|
| Screening | 05-MAR-1998 (0) | | | |
| Visit 1 | 12-MAR-1998 (5) | 100% | COLLECTED | |
| Visit 2 | 26-MAR-1998 (12) | 100% | COLLECTED | |
| Visit 3 | 09-APR-1998 (12) | 100% | COLLECTED | |
| | | | COLLECTED | |

SUBJECT: 6002/KG/2
Gender: F          Last Visit Date:   09-APR-1998    Reason for Discontinuation
Age:               Last Visit Label:                  DEATH
Date of Birth: 26-JUL-1969    Tx Started:

Ready                                                         6/18/98 14:07:04

FIG. 61

PROSIT – Never Never Land

Site / Subject Summary Report

PROSIT – SITE / SUBJECT SUMMARY REPORT

| Schering No. | Working Study Title | | Protocol No.-Site No. |
|---|---|---|---|
| 032088 MOMETASONE | MOMETASONE VS. Budesonide in Athsma | | 0000033-1 |
| Principal Investigator | Study Location | | Monitor |
| J G ORTIZ | ENGELWOOD, CO, UNITED STATES | | |

Site 1 Details

Site Status: ENROLLMENT ONGOING    # Subjects Projected:    Data Collection Tool: CRF

| Enrollment Summary | Site Level | Subj. Level' | Milestones | | Monitoring Summary | CRF |
|---|---|---|---|---|---|---|
| # Subj. Ineligible for Screening: | 0 | 0 | Site Initiation Visit Date: | | Total Visits Completed: | 6 |
| # Subj. Screened: | 0 | 2 | First Subject Screened: | | Visits Monitored: | 4 (66%) |
| # Subj. Failed Screening: | 0 | 0 | First Subject Enrolled: | | Visits 100% SDV: | 1 (16%) |
| # Subj. Enrolled (% Projected) | 0 | 2 | Last Subj. Enrolled to Date: | | Visits Collected: | 4 (66%) |
| # Subj. Ongoing: | 0 | 1 | Enrollment Complete: | | Date of Last Contact: | 25-MAR-1998 |
| # Subj. Discontinued: | 0 | 0 | Last Subject Last Visit: | | Date of Last Visit: | 25-MAR-1998 |
| # Subj. Complete: | 0 | 1 | Close Out Visit: | | Visits at the Site: | 1 |

Per Subject Summary

| Subject ID | Age | Gender | Date Enrolled | Status | Last Visit (phase) | Last Visit Date | Reason for Discontinuation | Eval | Date RX Started | Date RX Stopped |
|---|---|---|---|---|---|---|---|---|---|---|
| 600 1DL 1 | 25 years | M | | O | t1v1 SCR | 04-FEB-1998 | | UN | | |

Start | Micrsoft Word Report | PROSIT – Never Ne...    2:00PM

FIG. 62

PROSIT – Never Never Land

Monitoring Status Report

PROSIT – MONITORING STATUS REPORT

| Schering No. | Working | Title | Protocol No.-Site No. |
|---|---|---|---|
| 032088 MOMETASONE | | MOMETASONE VS. Budesonide in Athsma | 0000000-1 |
| Principal Investigator | Study Location | | Monitor |
| J G ORTIZ | ENGELWOOD, CO, UNITED STATES | | |

Site 1 Summary    As Of 25-MAR-1998    Site Contact No: 2626

| | Visits | | Subjects | |
|---|---|---|---|---|
| Protocol: | Amended | Completed | 6 | Projected: |
| Site: | Enrollment Ongoing | Monitored | 4 (88%) | Actual # Screened: 2 |
| Visits at the Site: | 4 | 100% SDV | 1 (18%) | Actual # Cancelled: 1 |
| Date of Last Visit: | 25-MAR-1998 | Collected | 4 (88%) | Actual # Completed: 1 |

| Site 1 Details Subject | V1 | V2 | V3 | V4 | V5 | V6 | V7 | V8 | V9 | V10 | V11 | V12 | V13 | V14 | V15 |
|---|---|---|---|---|---|---|---|---|---|---|---|---|---|---|---|
| 600WDV1 | (100) | (k) | (k) | (100) | | | | | | | | | | | |
| 7ICR18007 | | | | | | | | | | | | | | | |
| Completed | 2 | 1 | 1 | 1 | 0 | 0 | 1 | 0 | 0 | 0 | 0 | 0 | 0 | 0 | 0 |
| Monitored | 1 | 1 | 1 | 1 | 0 | 0 | 0 | 0 | 0 | 0 | 0 | 0 | 0 | 0 | 0 |
| Collected | 1 | 1 | 1 | 1 | 0 | 0 | 0 | 0 | 0 | 0 | 0 | 0 | 0 | 0 | 0 |

Legend: C= Completed:100=100%;SDV=Collected: xxxxx = D xxxxxxx
V1- xxxxxx V2- xxxxxxx V4xxxxxxx

FIG. 63

PROSIT – Never Never Land

Site Personnel & Locations Information Report

PROSIT – SITE PERSONNEL & LOCATIONS INFORMATION SHEET

| Schering No. | 032066 MOMETASONE | | Working Title | Mom vs. Bud in Asthma |
|---|---|---|---|---|
| Protocol No. | AP00045-1 | | Expense Center | 1763–CLINICAL RESEARCH–ALLERGY II |
| Principal Investigator | J TABAS COMINGUILLAN | | Monitoring Country | Never Never Land |

NON SP PERSONNEL

Maid, Mer
IRB CHAIRMAN
NNL
Active: 22-Apr-1998

Tabascominguillan, J
Principal investigator
NNL
Active: 22-Apr-1998

Bell, Tinker
STUDY COORDINATOR
NNL
Active: 22-Apr-1998

CENTRAL IRB/EC

MERMAID ROCK
2 Stone Skip
NNL

TREATMENT CENTER

PIRATE SHIP
Out at Sea

Ready                                    6/18/98 14:07:04

FIG. 64

PROSIT – UNITED STATES

Contact Information Report

PROSIT – CONTACT INFORMATION SHEET

| Schering No. | 000058 NIACIN | Working Title | | domestic |
|---|---|---|---|---|
| Protocol No. | A000001 | | | |

PROTOCOL A000001    EXTERNAL ORGANIZATIONS

CENTRE UNIVERSITAITRE DE SANTE   #1200          National Genetics Institute
Gunn, Mark C   Aarons, A L                                   Kadman, D
DE L LESTRIE 3001 12E AVENUE   1200 Fleet Street   5839 Green Valley Circle # 104
97                                                        FAX: 1-310-996-6610
Voice:                                                    FAX: 1-310-996-6610
Fax:           FAXCAN                                     Culver City   USA
Quebec NORD                    Manchester London UK
         SHERBROOKE, QUE
Site: 1                        SP PERSONNEL Rispoli, Marc C
Grint, P C                     PROJECT PHYSICIAN
DSS Specialist                 KEY PRODUCT MGMT.
Il-10 IN 10D/HIV               USA
USA                            www.tester.com
Active: 26-Feb-1998            Active: 26-Feb-1998

Gunn, Mark C
SITE REQUESTOR
WORLDWIDE RSCH QA
USA

Ready                                              2/26/98 9:52:37

FIG. 65

PROSIT – Never Never Land

File | Edit | Actions | Modules | Forms | Window | Help

Pre-Study Visit

EDT Form 1578
Investigator Assessment
Investigator Report
Investigator Request

Protocol: 000065
Pre-Study Visit No.: 2867

Pre-Study Investigator Visit

Investigator Formalization Form
EMP Form
Formulated Materials Request
Packaging/Shipment Request Form
Material Order Request Form Pre-Study Visit  SP Per
Potential Investigator: Hook, Cap

MOMETASONE

Country: Never Never Land

Country: Never Never Land
Visit Date: 31-Mar-1998  Time: 11:00   Finalized: 00-0000   [Evaluation]

Schering Participants:

Pan, Peter J
Butt, Thud

Investigator Site Participants:   Non-Registered ( )

Deck, Hanz
Hook, Captain
Smee, Mister

CLINICAL TRIAL MANAGEMENT SYSTEM

This application claims the benefit of U.S. Provisional Application No. 60/153,344 filed Sep. 10, 1999. The present invention is directed to the management of clinical trials and, more particularly, to computer software applications and databases that facilitate the management of clinical trials.

BACKGROUND OF THE INVENTION

Before a new drug can be approved for sale to the public, governmental agencies require proof that the drug is safe for use and effective in treating some condition. To establish this, drug companies conduct tests of the drug. These tests may involve giving the drug to animals and measuring the result. However, where the drug is intended for humans, a final phase in the testing process is the conducting of clinical trials in which the drug is administered to humans and the results are measured. These tests are expensive and time consuming to design and carry out. If errors are made during the tests, the resulting data may be useless, and the test may have to be repeated, delaying the ultimate approval of the drug, resulting in lost income to the drug company, and the additional expense of repeating the tests.

In order to ameliorate the potential for flawed clinical trials, various companies offer software that is intended to help manage these tests. For example, the Fraser Williams Company of Birmingham, UK, sells its Impact software for this purpose. IBM sells a program called ClinWare for the same purpose. The programs Sitebase from Parexel International Corporation of Boston, Mass.; and e.Power Clinical by Universal Systems Inc. of Chantilly, Va., all serve similar purposes.

It frequently occurs that a clinical trial for a new drug will be conducted at multiple locations nationally and internationally. This helps to test the drug on diverse populations, to assess environmental differences, and to spread the burden of locating and managing a large number of people who will become the test subjects of the trial. Since laws governing clinical tests vary from country to country, the administrative management of the protocol for the trial may have to be tracked differently, yet the administrative data must be sufficiently uniform for it to be combined into total trial management results. Further, the administrative data from the different sites of the trial must be integrated in an efficient way into a single database. However, providing access to this database from around the world and by numerous users, can lead to performance degradation, e.g., slow performance and problems with access. Prior systems do not adequately address this problem.

While the prior systems allow for the design of linear trials, it may be that a protocol requires split treatment, depending on the subject's response to the drug during treatment. In particular, if the early outcome is one result the treatment is governed by procedure A, and is governed by procedure B if the result is otherwise. The prior systems cannot adequately plan and track and display such complex trials.

The prior systems require extensive maintenance to input information on the personnel and medications available for the clinical trial. Consequently, methods for reducing the data input requirements would be beneficial. Further, information in one trial may be the same as information in another trial, but be identified with a different name. Similarly, information given the same name can be very different. Management of this nomenclature and definition problem is particularly important in situations where there is a need to combine the planning and tracking results of several trials.

The development of protocols for clinical trials is an ongoing procedure. Thus, there is a need to be able to easily modify a protocol to include new requirements. It should also be easy to tailor a global protocol to meet country and site requirements. Most prior systems lack this degree of flexibility.

SUMMARY OF THE INVENTION

The present invention is directed to an efficient clinical trial management system that allows for the rapid development of protocols on a hierarchical basis using templates. The templates include required tasks that can be linked to programs previously developed with the templates and can be updated as needed. Further, the system is designed to incorporate data from other databases to reduce data input requirements and to standardize definitions.

In an illustrative embodiment of the invention, a clinical trial management system includes a database which is used and maintained by a software application driven by a graphical user interface. The system allows for the creation and management of a plurality of clinical trials worldwide. Other databases in an enterprise, e.g., Human Resources, are linked to the system and provide a rapid means for inputting and maintaining information in the system database.

The system is modular in nature, having a variety of modules to handle different aspects of the development and management of a clinical trial. These modules include a Protocol module for establishing tracking information about a clinical trial (e.g., a protocol number) as well as the design of the administration of the protocol, e.g., the assignment of personnel to conduct the trial.

The main module is a Study Planning & Tracking module which defines master and core tasks for any trial, and allows the use of templates to design the plan for the trial. This module also allows for active tracking of the trial. If the definition of master or core tasks is changed by a system administrator, this new or different task is replicated in all templates. Further, new templates can be created by modifying old ones or by entry of a completely new one.

There is also a Site Management module for establishing information about a site where a trial is to be conducted (e.g., a site number, budget, etc.) and the resources at the site (e.g., personnel available at that site). A Site Contact module allows for the tracking of information received from visits to the sites where the trial is being conducted. In addition there is a Remote or Laptop module that allows information at a remote site to be entered onto a laptop computer at the remote site and later downloaded to the system. A Clinical Supplies module provides information as to the type and dosages of medications and medical devices that are available for the trial. This module also allows the system user to create shipping instructions for these materials so they will be available at the trial sites and/or allows the user to revise the trial, e.g. use different supplies, based on the materials which are available.

The system also includes a Report module that generates various standard and customized reports on individual clinical trials and the entire clinical trial operation across the world.

One feature of trials developed using the system is the Event Manager which automatically determines when an event in the trial has occurred that has an effect on another process in the trial. In effect this allows the completion of the last of a series of lower level tasks to trigger notification of the completion of the overall task.

The system also has a significant data replication capability. In the first instance, the system is connected to other databases, such as the Human Resources and Clinical Supplies databases of the company. As employees join and leave the company, this information is naturally maintained in the company Human Resources database. The system of the present invention provides a link to this database so that when a trial is being designed, all of the available personnel can displayed for selection. This is achieved without having to input this data into the clinical trial system separately, thus saving in time, effort and expense. A similar connection is made to the Clinical Supplies database which keeps track of the drugs and medical devices available for use. As these materials are used by personnel in the company or new ones are produced, the quantity and type of inventory changes. By having a link to this database, the designer of a clinical trial can determine what products are available, and can reserve them for the trial. As necessary, links can be made to other databases to import information as needed, which eliminates the need to create and maintain other separate databases for use by the system.

In a preferred configuration the system is a main file server and database at a central location, e.g., the research headquarters of a company. It is linked to subsidiary processors and databases at remote locations, e.g., in other States or countries. All of the system information is held in the main database, and subsets of that data are maintained at the remote locations. A further replication system is maintained so that an update of data at the remote or main databases will propagate to the other databases. Rules are provided to avoid conflicts. For example, the database at a remote subsidiary location will have only data related to that site and certain core information cannot be changed remotely. A change in core information at the main location automatically replicates to the necessary remote locations. The remote subsidiary locations can store some information that is not replicated to the main database, but all critical information is replicated. Also, the subsidiary locations have priority with respect to modifying particular rows of some data tables, even in the main database.

Once the clinical trial has been planned, it can be displayed graphically as a Visit Map which shows the times when a patient is to visit a site to receive medication and/or be tested. This is particularly helpful when according to the plan, different courses of action are to be taken for the patient depending on interim results of the trial.

BRIEF DESCRIPTION OF THE DRAWINGS

The foregoing and other features of the present invention will be more readily apparent from the following detailed description and drawings of an illustrative embodiment of the invention in which:

FIG. 4 is the main Protocol Request screen of the system of the present invention;

FIG. 5 is the Protocol Number Request Details screen of the invention;

FIG. 6 is the Protocol Administration screen of the invention;

FIG. 7 is the Employee Roster screen of the invention;

FIG. 8 is the Protocol Design screen of the invention;

FIG. 9 shows the Medications Tab on the Protocol Design screen of the invention;

FIG. 10 shows the Visit Map Tab on the Protocol Design screen of the invention;

FIG. 12 shows the Procedures Tab on the Protocol Design screen;

FIG. 13 shows the Optional Fields Tab on the Protocol Design screen;

FIG. 14 shows the Subject Eligibility Tab on the Protocol Design screen;

FIG. 15 shows the Reasons for Discontinuance area of the Subject Eligibility Tab of FIG. 14;

FIG. 16 shows the Study Objectives Tab on the Protocol Design screen;

FIG. 17 shows the Protocol Amendment screen of the invention;

FIG. 18 shows the Master Task List for the protocol design of the invention;

FIG. 19 shows the Core Task List for the protocol design of the invention;

FIG. 20 shows the Core Site Instruction List for the protocol design of the invention;

FIG. 21 shows the Template Tab Folder for the protocol design of the invention;

FIG. 22 shows the Template Dialog Box for the protocol design of the invention;

FIG. 23 shows the Protocol Projections Tab of the Study Planing screen of the invention;

FIG. 24 shows the Study Planing Tab of the Study Planing screen;

FIG. 25 shows the SMP Study Planing Tab of the Study Planing screen;

FIG. 28 shows the Site Number Request screen of the invention;

FIG. 29 shows the Site Request Detail screen of the invention;

FIG. 30 shows the Site Administration tab of the Site Administration screen of the invention;

FIG. 31 shows the Post-Study Evaluation tab of the Site Administration screen;

FIG. 32 shows the Site Personnel & Locations screen of the invention;

FIG. 33 shows the Company Personnel tab of the Site Personnel & Locations screen of the invention;

FIG. 34 shows the Non-employee Personnel tab of the Site Personnel & Locations screen;

FIG. 35 shows the Non-employee Locations tab of the Site Personnel & Locations screen;

FIG. 36 shows the Site Study Tracking screen according to the invention;

FIG. 37 shows the Site Budget screen according to the invention;

FIG. 38 shows the Site Payee tab of the Site Budget screen;

FIG. 39 shows the Site Budget tab of the Site Budget screen;

FIG. 40 shows the Subject Cost tab of the Site Budget screen;

FIG. 41 shows the Pre-Visit screen of the invention;

FIG. 42 shows the Non-employee tab of the Pre-Visit screen;

FIG. 43 shows the Discussions tab of the Pre-Visit screen;

FIG. 44 shows the Evaluations tab of the Pre-Visit screen;

FIG. 45 shows the Visit Contact screen according to the invention;

FIG. 46 shows the Non-Contact Visit screen according to the invention;

FIG. 47 shows the Discussion Item tab for the Contact screens;

FIG. 48a shows the Site Tracking screen of the invention at the Enrollment Tracking tab;

FIG. 48b shows the Ineligible For Screening tab of the Site Tracking screen;

FIG. 49 shows the Subject Visit Tracking screen of the invention;

FIG. 50 shows the Visit Summary tab of the Subject Visit Tracking screen;

FIG. 51 shows the Clinical Supplies screen of the invention;

FIG. 52 shows the Packaging/Shipping Request ("PSR") screen of the invention;

FIG. 53 shows the Components tab of the PSR Packaging screen;

FIG. 54 shows "Ship To" tab of the PSR Packaging screen;

FIG. 55 shows the Material Transfer Request ("MTR") Details screen of the invention;

FIG. 56 shows the "Ship To" tab of the MRT screen;

FIG. 57 shows the Random Code Request screen of the invention;

FIG. 58 shows the Check-In/Check-Out Status screen of the invention;

FIG. 59 shows the Subject Detail Report screen of the invention;

FIG. 61 shows the Site/Subject Summary Report of the invention;

FIG. 62 shows the Monitoring Status Report of the invention;

FIG. 63 show the Site Personnel & Location Report of the invention;

FIG. 64 shows the Contact Information Report of the invention; and

FIG. 65 shows the Forms menu on the mail screen.

DESCRIPTION OF AN ILLUSTRATIVE EMBODIMENT

Figure 1:
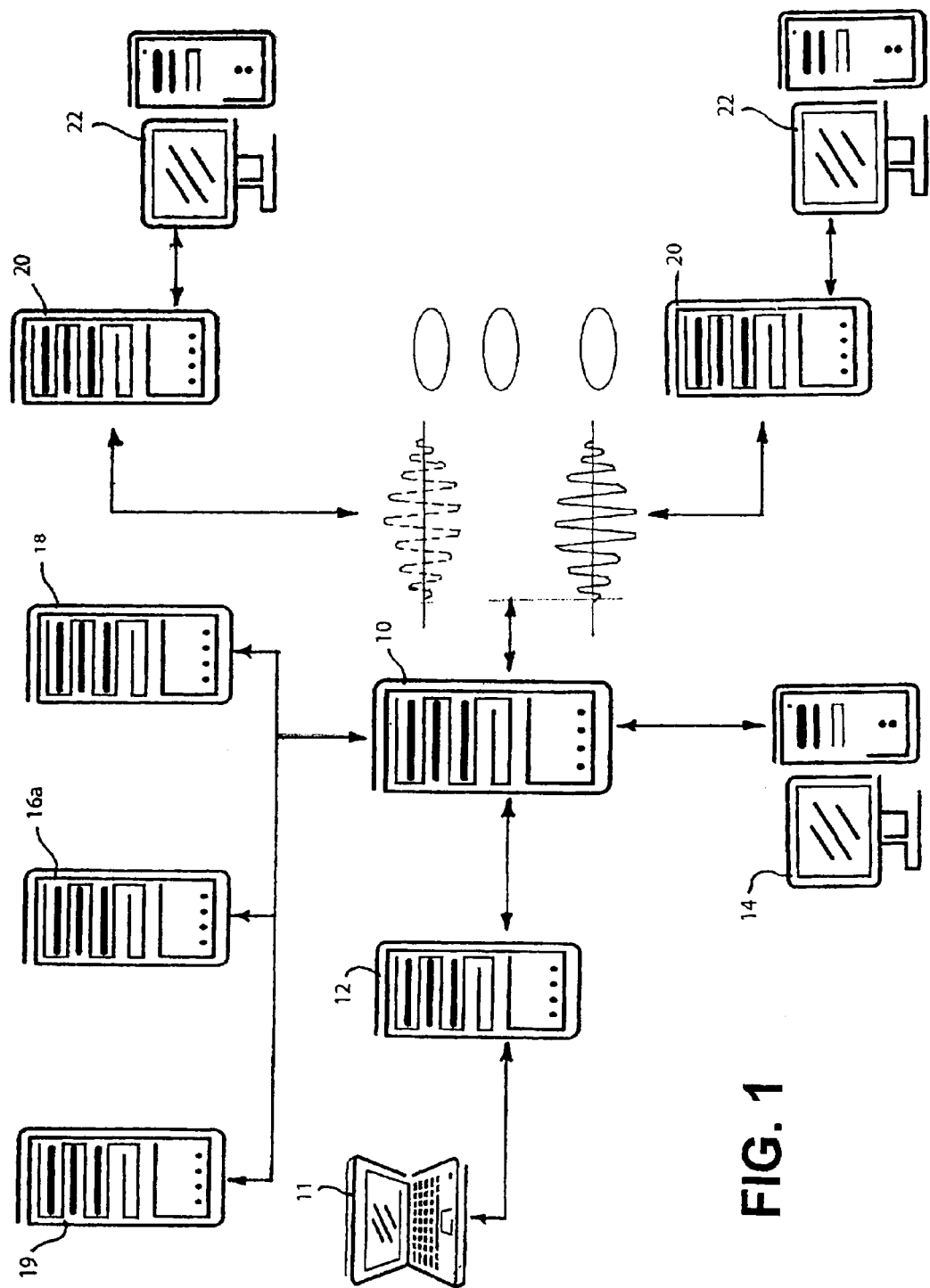
FIG. 1 is a block diagram of the hardware used to implement an embodiment of the present invention.
Figure 2A:
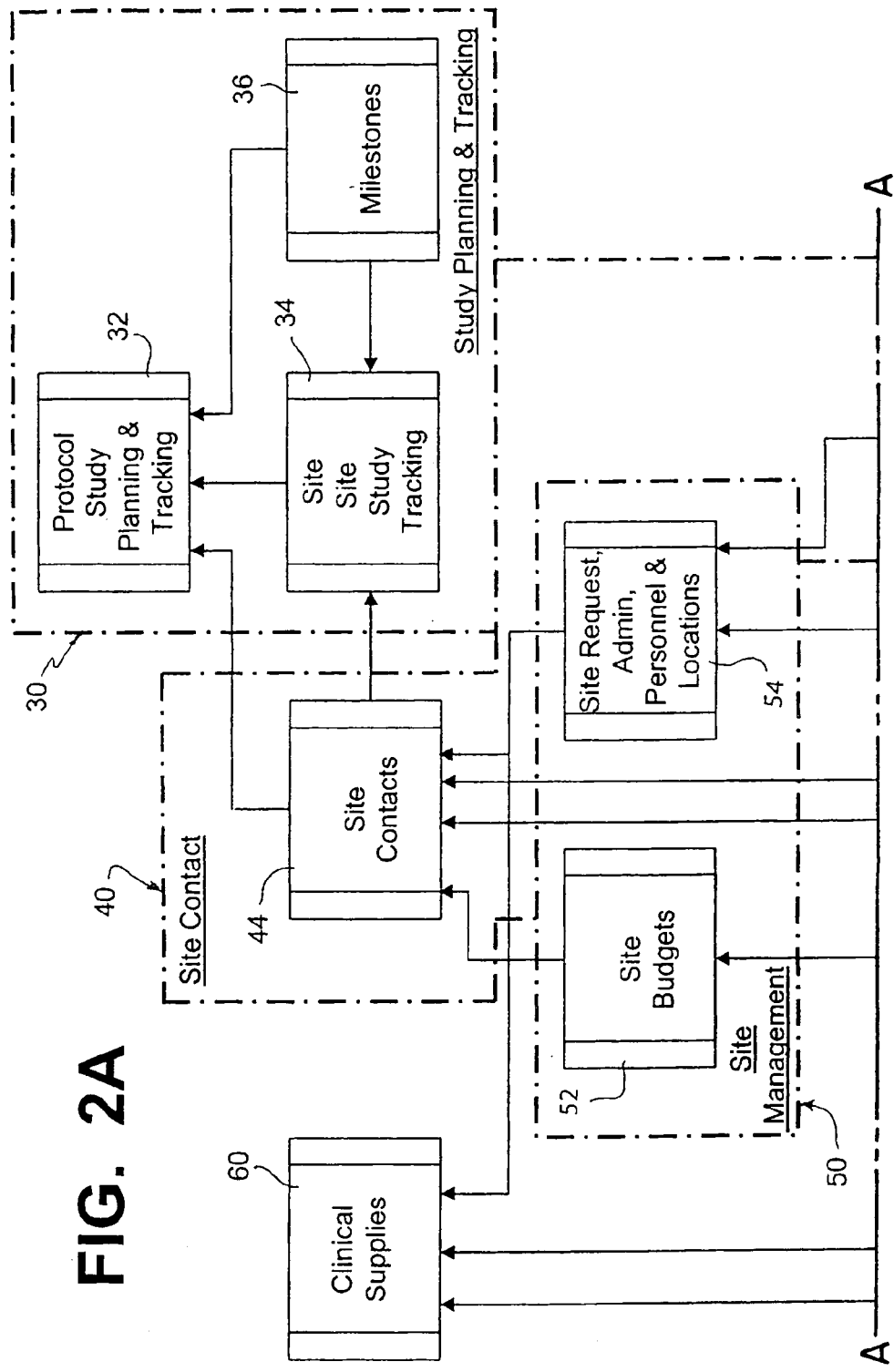
FIG. 2 is a diagram showing the interconnection of various software modules that form parts of the system of the present invention.
Figure 2B:
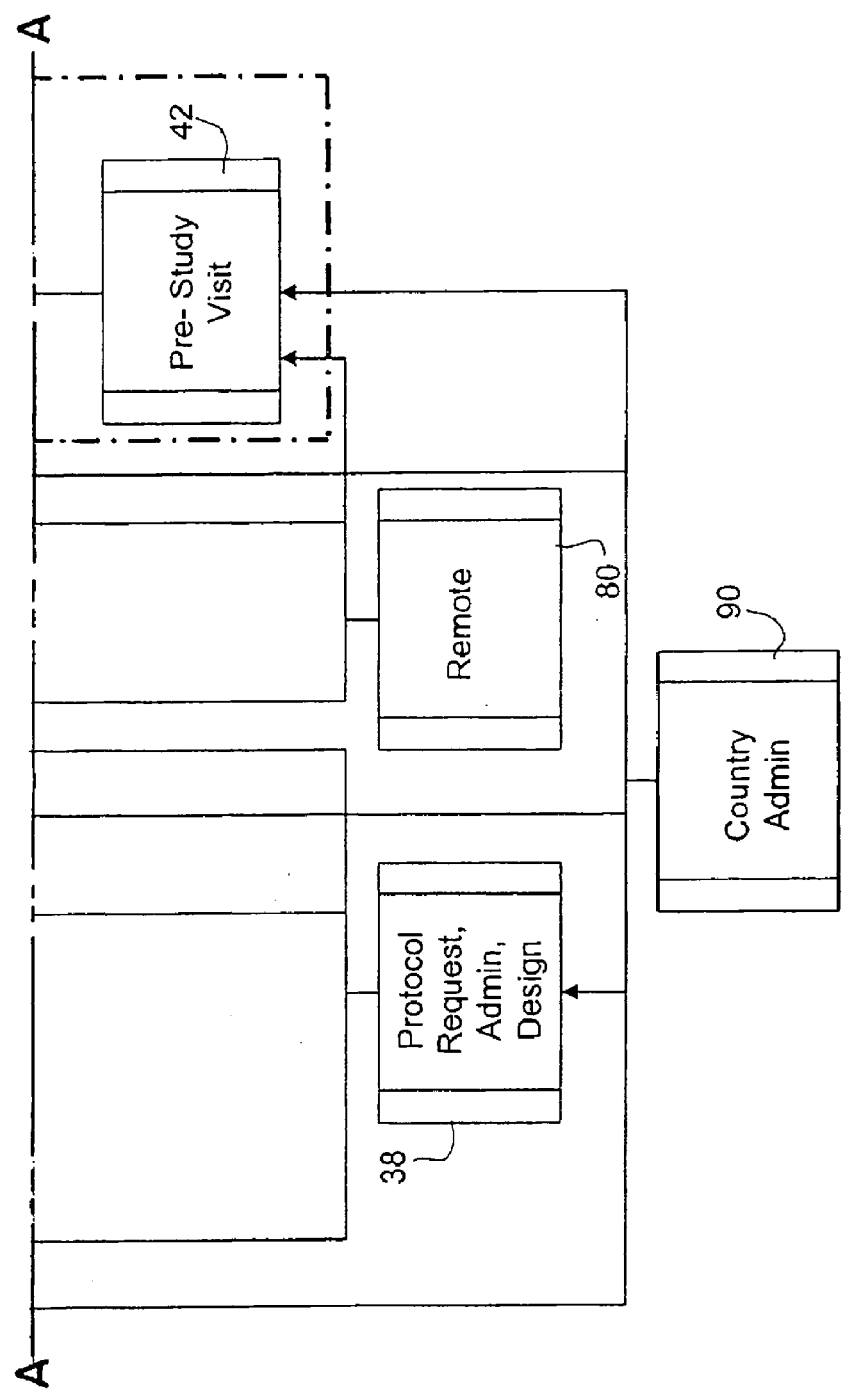

In FIG. 1 there is shown an arrangement of processors (file servers and databases) for carrying out one embodiment of the present invention. This physical arrangement operates according to a program which allows multiple clinical trails to be designed and monitored throughout the world.

1. Hardware Arrangement

In this embodiment, it is assumed that the system is being utilized by a pharmaceutical company in the United States to conduct clinical trials at various locations within the United States as well as at various sites throughout the world. The application software typically is shared by a main database server 10, a user processor 14, remote or subsidiary/country servers 20 and subsidiary user processors 22. The database server 10 can be a R6000 running UNIX AIX v4, ORACLE Server v7.3.4, and SQL*Net software, and TCP/IP communications. There is also a check-out/check-in server 12 for use with laptop computers 11. This server can be a Compaq Proliant 2500, with a 17 Gig hard drive and running Windows NT server v 4, SQL* Net, and SQL Anywhere v5 software, with TCP/IP communications. The user or client processor 14 as well as the subsidiary user processor 22 can be a Pentium or higher PC running MS Windows 95, SQL*Net and SQL Anywhere v5 software, and connecting with the main database 10 using TCP/IP protocols. This allows the physical hardware to be located at any remote location necessary.

In FIG. 1 the user 14 will be assumed to be someone with supervisory rights allowing them access to the entire database. This, however, is solely for the purpose for illustration. In practice there will be numerous users and a hierarchy of access rights to control the nature and extent of their access to the data in the database.

The main data is stored in the database connected to the database server 10. This will include all material data input into the system. In addition, as shown, there is a link between the system database and other cooperating databases that may have information of use to the system. In this particular instance there is a connection between the database 10 and a Human Resources database 16. This Human Resources database is one ordinarily maintained by the company and which is constantly updated by human resource personal, so that it contains a complete up-to-date listing of the personnel employed directly by the company or who are under contract to the company. It also contains information about various company locations and the location of clinical trial partners throughout the world.

A further corporate database, the Clinical Supplies database 18, is also shown connected to the system database 10. This clinical supplies database is normally maintained, availability by the Clinical Supplies department of the corporation. It keeps track of the production, availability and distribution of clinical supplies, which are different than the production supplies distributed through commercial channels. Thus, investigatory drugs and devices are typically produced by this group and stocked by it, while production manufacturing will typically deal with governmental health authority, e.g. FDA approved drugs that are being commercially distributed. Thus, if an investigator has created a new drug and wants to establish a clinical trial for it, the supplies of that drug would be created by the Clinical Supplies department and the inventory of it would be maintained in the Clinical Supplies database 18. Information on budget allocations, costs, etc. can be provided to the system from a Finance database 19 normally maintained by the company, at least as regards operations in the geographical location of the main database. Any convenient means can be provided to make the link between database 10 and these associated databases, e.g., a dedicated line or the Internet using TCP/IP protocols.

Besides the databases shown in FIG. 1, advantageous use can be made of other databases of the enterprise. For example, databases of regulatory information, clinical documentation, codes and libraries of information can be effectively linked to the system to provide access to useful data without having to manually load it into the system.

It frequently occurs that clinical trials are conducted at more than one location and typically at a location other than the corporate headquarters of the company operating the system. These other locations can be in various States throughout the United States and at various countries throughout the world. The present system contemplates a two tier system for handling such arrangements. For example, the main database may handle several clinical trial sites located in the United States. However, trial sites at subsidiaries outside the United States can be handled by subsidiary servers 20 in those countries. Such sites, for example, could be the residences or offices of investigators who are participating in the clinical trials, such as hospitals or universities, in the foreign countries. While in FIG. 1 only two such servers are shown, it should be understood that they can be numerous.

The clients of the system, which in the case of a foreign country would likely be those personnel engaged in managing the trial, would have TCP/IP connections to the subsidiary/country database server 20 in their geographical location. The subsidiary servers 20 can be a Compaq Proliant 2500 with 17 to 54 Gig of hard drive space. It could run NT Server v4, Oracle Server v713.4, SQL*Net, and SQL Anywhere v5 with TCP/IP communications. The actual size of the hard drives for the subsidiary servers 20 depends on whether or not data is mirrored and whether or not the local country database will have a significant amount of information which is deemed as unnecessary to be stored on the centralized database 10 in the U.S. Typically, each country will have a subsidiary server 20, which is addressed by a plurality of users 22.

The system includes the hardware set forth in FIG. 1, as well as software to cause it to operate in the desired manner.

2. Software Overview

The system automates tasks ranging from protocol and site number assignment, to monitoring visit report creation, to full-scale study time-line planning and tracking. It is designed so that data can be re-used for multiple functions. This means that information entered into one area of the system will be accessible throughout the application to many users for use over and over again. Some of the primary users of this information, either directly or indirectly, are:

Study Monitors, who use the system to record the status of studies at their sites and their patients, and to subsequently generate site related documentation to substantiate due diligence in study monitoring;

Clinical Research Management personnel, who uses the system status information to monitor study progress and to adjust the organization's activities and deployment of resources;

Clinical Documentation Management personnel, who rely on the FDA required forms generated through the use of the system;

Clinical Manufacturing/Clinical Statistics personnel, who manufacture, randomize, package and ship drugs and other medical devices for clinical studies based on output from the system; and Clinical Research Finance personnel, who allocate funding based on budget studies generated by the system;

The system is structured from the point of view of the person acting as the creator and monitor of the clinical study. All the users in management, manufacturing and finance rely on the proper recording of these tasks in order to achieve their individual objectives. Thus, in the system according to the present invention, an important feature is that it can be used by the study monitors as an integral part of their routine. This capability makes possible various secondary objectives. To support this primary objective, the system is broken into distinct modules to organize the 100 plus screens into logical areas that can be readily used by a person acting as a study monitor.

Figure 27A:
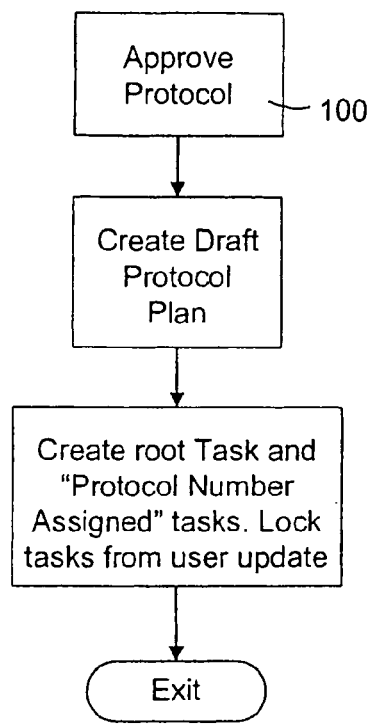
FIGS. 27a to 27i are flow charts of the operations of the Event Manager.
Figure 27B:
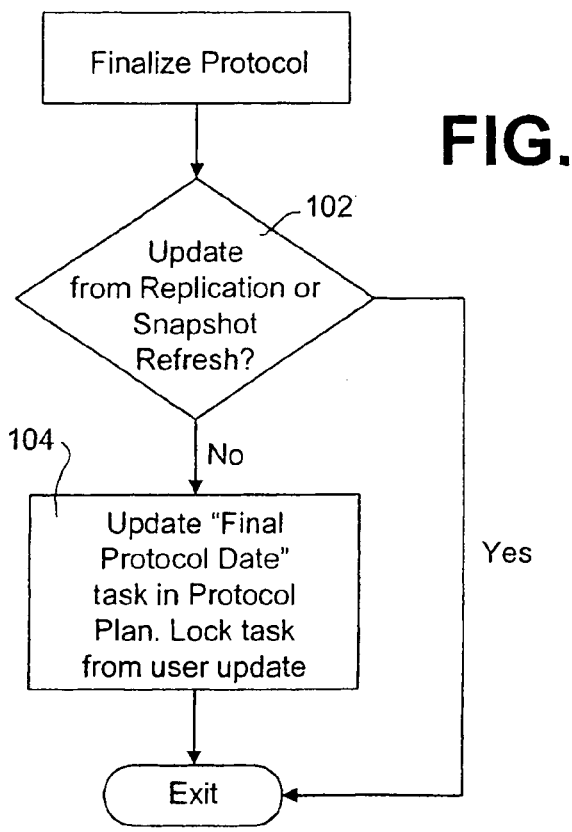
Figure 27C:
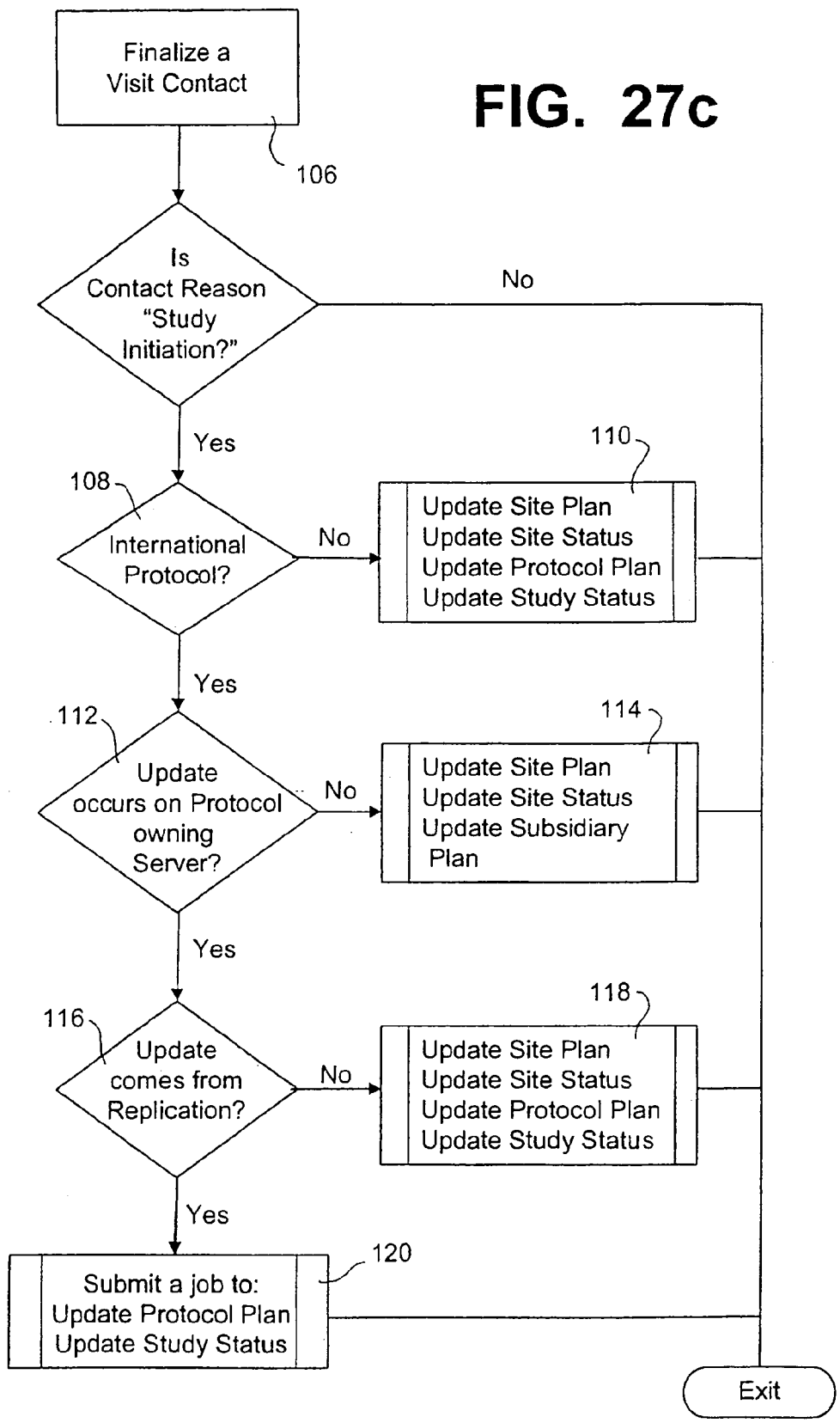
Figure 27D:
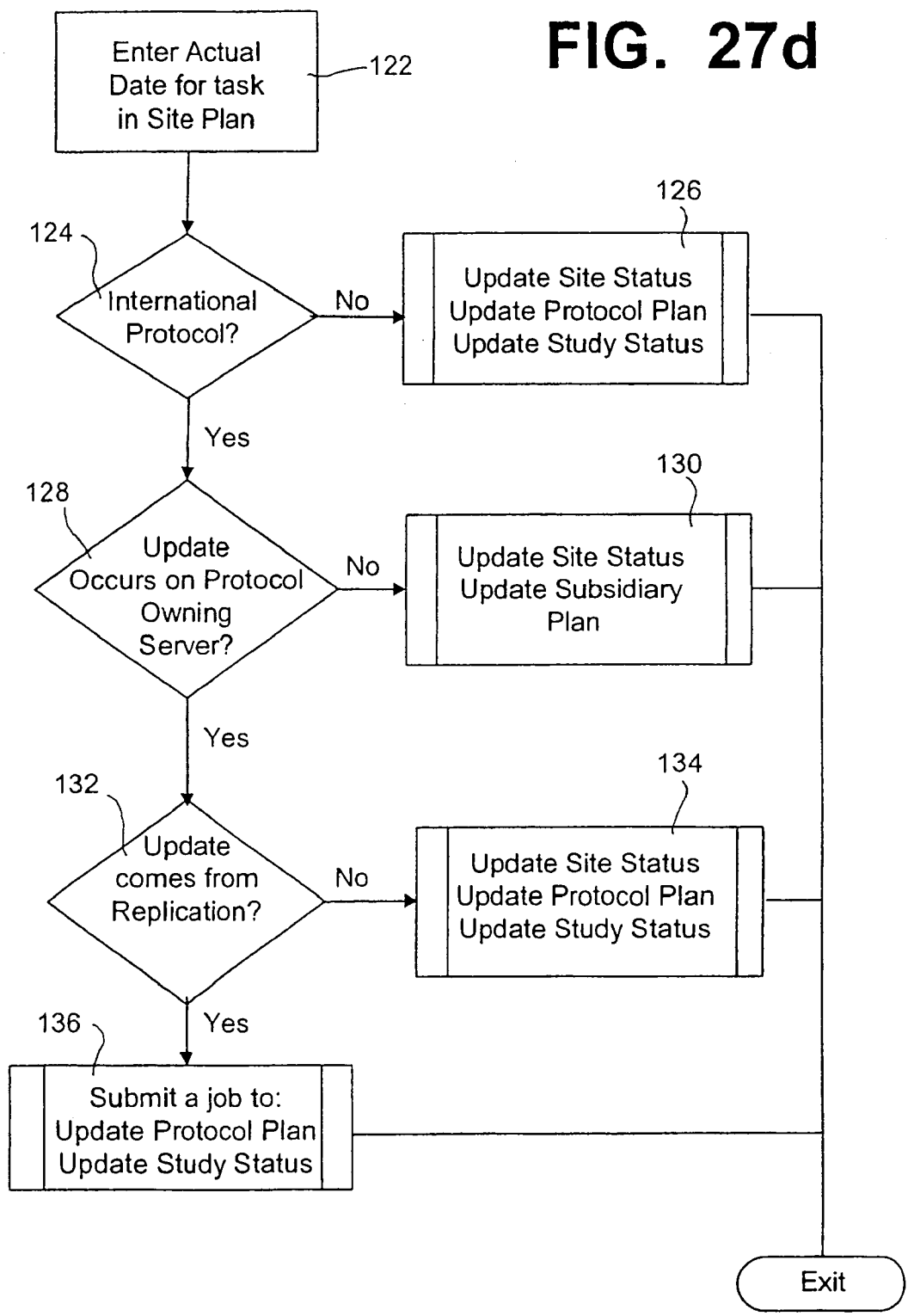
Figure 27E:
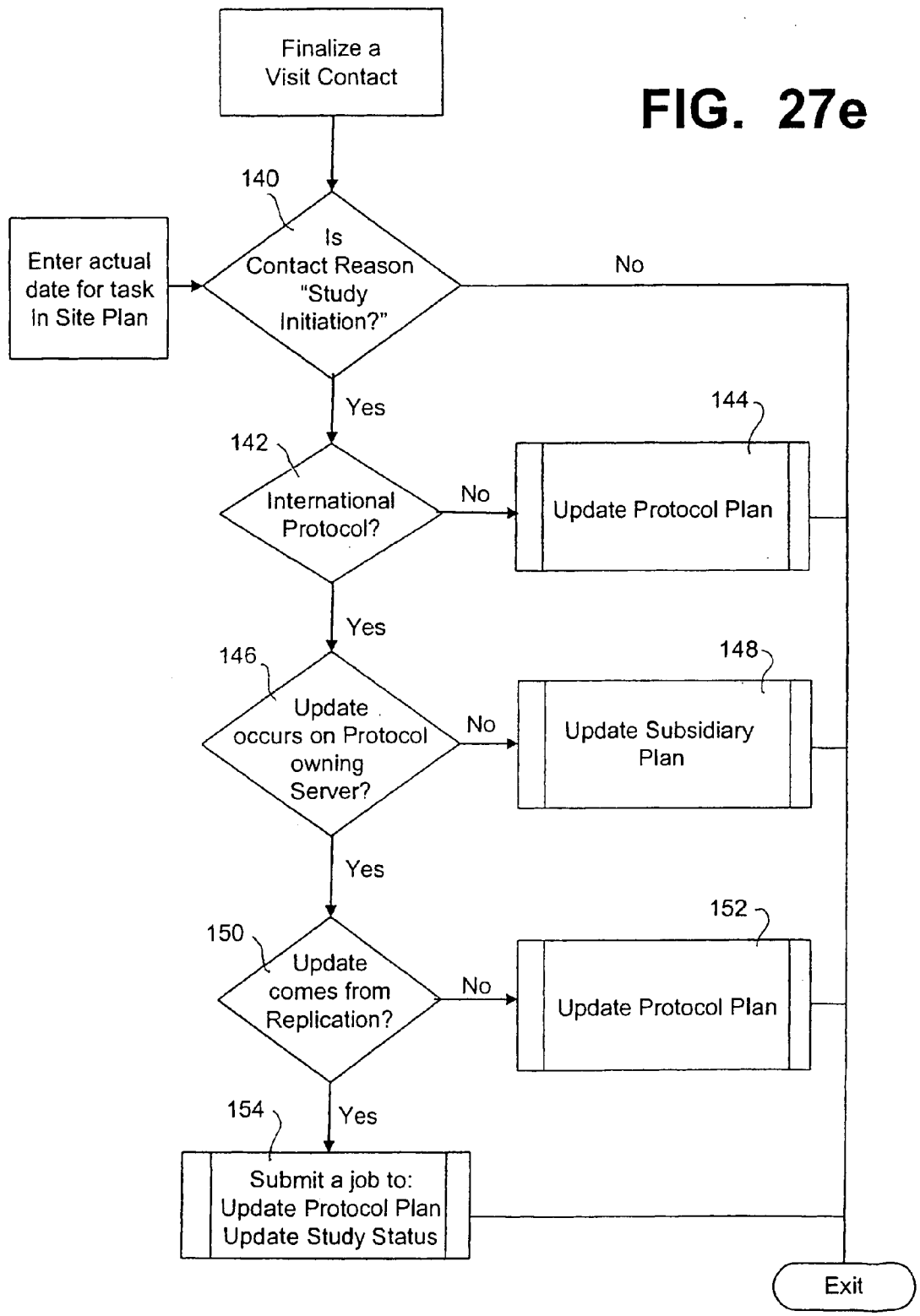
Figures 1, 27F:
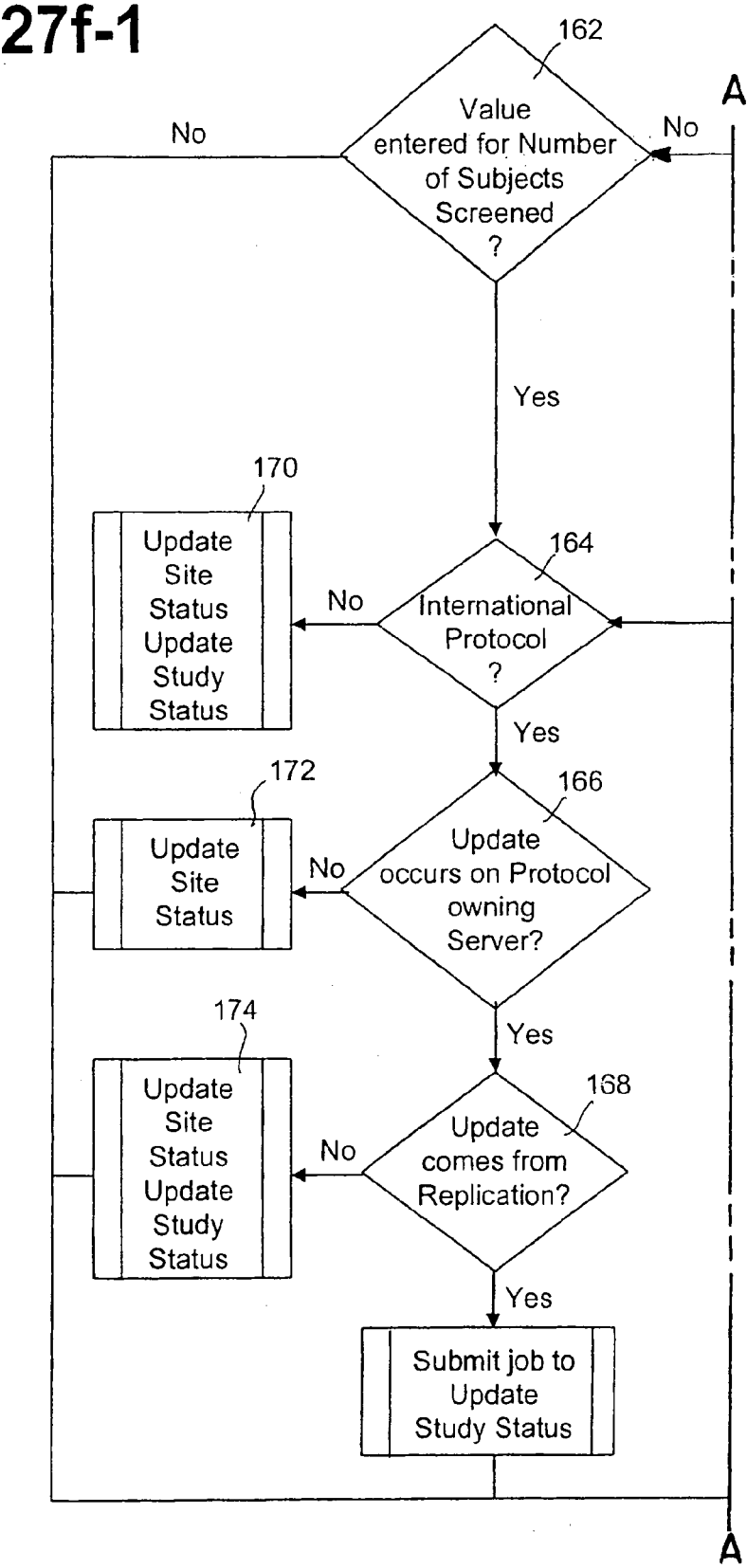
Figures 2, 27F:
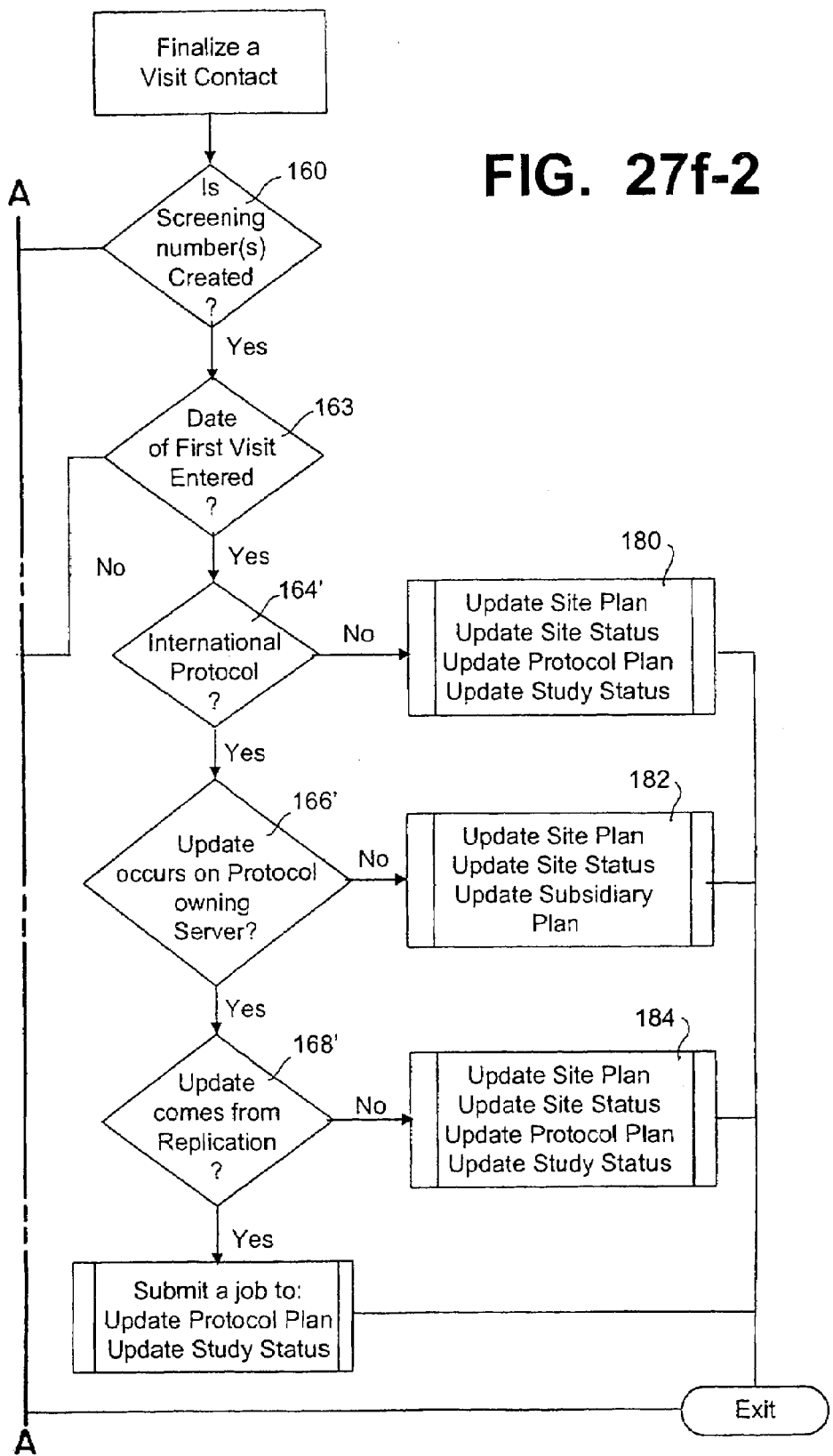

FIG. 2 is a diagram that illustrates the primary interrelationships between many of these various software modules and will be discussed in the order in which a study creator and monitor would use them. In particular, the Site Contacts module 40 includes the Pre-Study Visit sub-module 42 and the Site Contact sub-module 44. These enable a study monitor to record all of the contacts they have with a study site or prospective study site, everything from a simple phone conversation to a site visit where medical records and informed consent documents are verified. The reasons for these site contacts include ascertaining the suitability of a site for participation in a study, monitoring the site's activities during the course of a study, confirming that the protocol is being conducted properly, reviewing the subject records for safety and compliance with the protocol, and assuring the accuracy of the data being recorded in the system.

The recording of information for a pre-study contact through sub-module 42 essentially requires the recording of assessments made by the visitor to the site as to the suitability of the site for the study. Once a study is underway there are four logical levels of contact information with the site that are recorded through Site Contact sub-module 44. The first two levels apply to all site contacts, but detailed information about the patients or their visits can only be recorded based upon a study monitor's visit to the site. The four logical levels are:

Site Contact Recording—Recording high level information about a visit, a phone call, a fax, or an E-Mail. The user keeps track of who participated, when and where the contact took place.

Site Performance Recording—The user records key summary information about the progress of the study at the site, such as how many subjects were enrolled.

Subject Recording—Recording general information on the individual subjects, such as age at enrollment and date of signed consent.

Subject Visit Recording—Recording information on each visit the subject has completed, and the individual procedures performed at each visit.

The Site Management module 50 includes site request, administration, personnel and locations sub-modules 52 and site budget sub-module 54. The Site Management module of the system directly supports the activities of the Site Contact module 40 in both an administrative and planning capacity. From an administrative perspective, the Site Management module 50 allows study monitors to request sites for investigators they have identified as willing and able to participate in a study. The study monitors then associate people and investigator facilities with the site, so that when site contacts are recorded, there are short "rosters" of people and places to select from. These rosters are also used to direct the official correspondence with regard to a study.

In addition to planning site activities, the Site Management module 50 also includes a Site Budget sub-module 54, which is where study monitors can plan the financial requirements for a site. For this the study monitors plug in the costs for the specific investigator, and calculations are then applied by the system according to the planned schedule of visits for each patient in order to budget investigator costs. The output is printed as supporting documentation for requesting a study grant.

The Study Planning and Tracking module 30 includes a Protocol Request and Administrative Design sub-module 38 (shown functionally separate), a Protocol Study Planning and Tracking sub-module 32, a Site Study Tracking sub-module 34 and a Milestones sub-module 36. At the start of the process, a protocol number is requested and certain administrative tasks are completed by sub-module 38. On the planning side, the Site Study Tracking sub-module is where the study monitor can itemize the tasks and key milestones in setting up, monitoring and closing a site. Once established, it records its progress. Some of these tasks get updated automatically, based upon site contact activity, by a component of the system called the Event Manager. The Event Manager can spot key events, such as a site initiation visit recorded as a site contact, and then update the corresponding task in the tracking screen as completed.

The Study Planning & Tracking sub-module 30 of the system serves two primary purposes. From an administrative and design perspective, its sub-module 32 is the foundation for the Site Management and Site Contact modules. In this role the module 32 allows the establishment of the planned visits that study subjects are expected to attend, what procedures are to be conducted at each visit, when the visits should occur, what drugs should be given and in what dosage, and so on. Essentially the full study or protocol is entered into the system in this Study Planning & Tracking sub-module 32.

The second primary purpose of the Protocol Study Planning and Tracking module is to provide a study tracking capability through sub-module 34. The module also disseminates top-down information on the plan of a study into the participating countries so it can be incorporated into their own study plans. Then the module uses Event Manager to implement a bottom-up approach on the tracking of events, rolling completion dates up from the site contacts to the site plans to the respective countries and finally to the overall protocol plan.

The Milestones sub-module 36 is an administrative system to support the Protocol Study Planning and Tracking module 30. The Master Tasks of the Milestones module are the global set of user-defined tasks set for the system by the administrator to be used in creating all plans. Core Tasks are country by country sets of required tasks, so that these pre-determined subsets of the master tasks must be included whenever a plan is created in the system. The Templates are, as the name implies, template plans comprised of the applicable country's core tasks, plus any additional master tasks or user defined tasks that the template author chooses. The templates are typically created to be therapy area specific, but this is entirely a business choice. The general idea is to create templates that minimize the effort required in performing detailed planning, by leveraging on the items that have been included in similar studies. The templates are selected when the user creates a study plan for the first time.

Since much of the usefulness of the system relies on accurate and complete study monitoring information, the system has been designed to travel on the road so that data can be captured at the actual site during visits. In this way Remote module 80 allows information to be received in a laptop computer. This is more a service than a module, since most of the functions proved in the Site Contact module 40 and even some of the functions in Site Management module 50 work on the laptop, and in exactly the same manner as on the stationary system. However, the processing of the laptop service is best described as supporting a check in/check out paradigm, as if checking books in and out of a library. A user checks out the data for one or more sites in preparation for a site visit. Once checked out, no other users of the system can enter or update any other visit information for that same site. Also, the Laptop allows the user to bring forward information from the previous site visit so that the new site visit information can be created by updating the old visit information. The user then records their visit on the laptop, and when back in the office, checks the data back into the main database so it is once again available in the main system. The Check Control aspect of the Remote module 80 allows the administrator access to cancel checkouts or to adjust priorities as needed.

The Check In/Out server components of the Remote module 80 are where the actual processing takes place. When a site is requested for checkout, this server 12 creates a small portable database for the specific site(s) and transfers it to the laptop 11. At check in time, the transactions that were entered on the laptop are transferred onto the server, and applied to the main database. To make all this happen in an automated fashion, numerous queues and programs run on the server 12 unattended.

The Clinical Supplies module 60 of the system generates the various standard forms within the organization for requesting the manufacture, randomization, packaging and shipment of drugs and materials used during the course of a study. Feeds from the clinical supplies manufacturing computer system provide summary information regarding drug quantities on hand and expiration dates. The drug and site location information from the Study Planning and Tracking module 30 and the Site Management module 50, respectively, establish some of the default information to facilitate these activities.

The Country Administration module 90 is a purely administrative module for entering and maintaining information about the people and locations referenced elsewhere in the system. These system rosters are sub-divided so that each subsidiary sees and maintains its own set of data. The personnel can be central office employees as acquired via a feed from the Human Resource system, subsidiary employees as entered in those countries, or consultants acting on behalf of the company, such as when a Contract Research Organization (CRO) participates in studies. The non-company personnel are typically site investigators and their staff members, but can also include others such as contacts at central organizations (labs, IRBs, etc) or billing and administrative contacts. The Facilities rosters contain site facilities, pharmacies, labs, hospitals and the like. Global payees are provided to the system via a feed from the company's Finance database as approved vendors, and the system provides a mechanism for requesting that vendors be added. The Local Payee option is available to subsidiaries, where payments are often made directly without the need to add them to the main Finance system. These administrative rosters form the foundation from which participating locations and people are selected in most of the other modules in the system.

Figure 3:
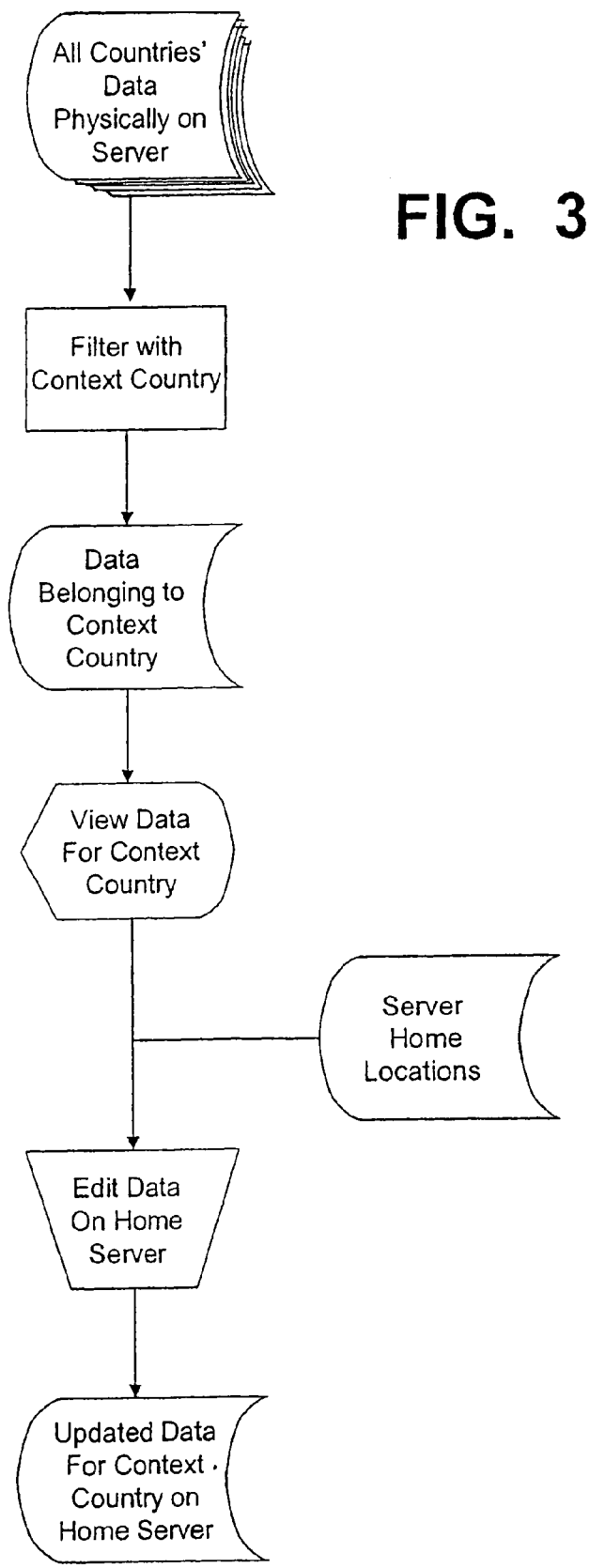
FIG. 3 is logical view of data in the system from the context of the subsidiaries.

The system uses a "context countries" or subsidiaries approach to separate the logical view of the data that the application needs, from the physical implementation of it. This is shown generally in FIG. 3. Each country in which the system operates will be available as a "context country." There is an "All Countries" context as well, which is a view-only context where all data is visible—regardless of what country it belongs to. This context is used largely for cross-country reporting and analysis.

A user's specific security access and the physical deployment of the data will restrict what contexts are available to him. A user is in one logical view or context at a time, and can access and update data based on his context. If he has access to more than one context country, he must choose one at login. The user can change the context at any time while working in the system via an easily accessible pop-up window of choices.

The system will control which rows of data are accessed by implementing views that join with the current context country. Generally speaking, these views will join on a sub-country-cd column, where sub-country-cd represents the country "ownership" of the data. The specific case of the "All Countries" context will be handled by bypassing these views and restricting the data from the application as needed.

In addition to the context country, there is also a "home server" within the application. The home server is where the data updates for a specific country are expected to take place. For instance, if France has a server, then their data resides on both that server and on the main server, e.g., the server in the U.S.—but the server in France is the home server. This home server concept is used to support application triggers, allowing them to control the effects of inserts, updates and deletes based on where they occur within the network topology. For example, site number assignment needs to happen on the Protocol's home server. If it is a French local protocol, that means site numbers are assigned on the French server—but international protocols originating in the United States assign site numbers on the US server. The home server concept allows the writing and distribution of one set of trigger codes to all servers in the system.

3. Data Replication

The home server concept is also used to put the application into a read-only mode for all screens, whenever the context country is not on the user's home server. This avoids possible replication conflicts that could occur if a user in France makes a change to the same piece of data as someone in the US on the same day. As a general rule, each row of data is tagged so it can be updated on one and only one server. There are one or two exceptions to this rule, but the system relies on its multi-country architecture and the concepts of context country and home server to ensure data integrity around the world.

As can be seen from FIG. 1, the system is a truly distributed client/server application. It can run on multiple interconnected database servers around the world, bringing the data close to the users, yet synchronizing all of their activities to ensure data integrity. This distribution improves the access time and processing speed of the system.

The two key elements of data replication in the system that ensure success are first, a logical architecture that insulates the application from the physical implementation; and second, replication conflict avoidance through data row ownership. The logical architecture that isolates the system from the physical database deployment is closely related to the Multi-Country Architecture. Using the Context Country, the system users see a filtered view of all the data physically located on their server. A user in Belgium would see only Belgium data, even if the Belgium user's machine hosts data from all over Europe. This provides tremendous flexibility in the actual deployment, allowing the consolidation or distribution of data across multiple machines as technology shifts.

With this logical isolation, the system capitalizes on several varieties of Oracle's replication product. Some tables are deployed around the world as read-only snapshots, meaning they are updated only on the main database and then shipped around the world as reference tables. The Drug table would be a prime example of a read-only snapshot. A second variety of replication is the system's use of updateable snapshots. These are tables which exist in their entirety on the main database, but have portions that are replicated out to each server worldwide. The exact portion of the table that gets replicated varies from server to server, based on which country or countries it hosts. For example, the Personnel table in the U.S. would contain all employees worldwide. The server in France, on the other hand, would contain only the data belonging to France—in this case the French employees. The third type of table which the system leverages is a basic non-replicating table, used for data intended to be kept private on a particular server. The security table of the system users, is a prime example of this kind of data. By combining these different types of tables and replication modes, the system maintains a flexibility well suited to the dynamics of a global business organization.

The second element of replication avoidance helps ensure that with all this flexibility, data integrity is still maintained. The principal strategy is to tag each row in the global database with a country of origin, or ownership. Since each piece of data in the system can be updated in one and only one place, replication conflicts will never occur. For the most part, the system uses this strategy. There are some notable exceptions, however, for which special programming logic is employed to resolve conflicts, or avoid them in some other way. A prime example of this is the requesting of study sites, which for an international study can be done by the participating country, such as Sweden, on their own server. Alternatively, the site can be requested on Sweden's behalf from the U.S. server. Since each country is limited to the number of sites they are allocated, the potential exists that the U.S. could give Sweden a site, and Sweden could request one at roughly the same time, causing a collision whereby Sweden has been issued too many sites. In this case, the special logic calls for a two-phase granting of sites. In this process, when Sweden requests a site the request must replicate to the U.S. before the request is fulfilled. In this way all those sites are actually committed in one place, and integrity is preserved.

The data integrity attained by replication avoidance and the flexibility of logical isolation from the physical implementation makes the system's replication architecture solid and adaptable. The simple elegance of this approach provides the foundation for future expansion as well. The business and the technologies that support it can evolve and adapt relatively independently.

Now that the overall system has been described, the details of the operation of the system in the process of creating and tracking a clinical trial will be described with particular reference to the graphical user interface and screens which the user manipulates.

4. Protocol Module

The Protocol Module of the system is the portion of the system that supports the initiation, definition, planning and tracking of clinical studies. This module would typically be used by the Clinical Documentation group, the Protocol Requestor, the Project Physician and those designated by the Requestor or Physician to be able to update the Protocol information.

This module consists of five sub-modules. The first sub-module is Request, which is used to obtain a unique Protocol number, indicate the originator of the study, the project physician, the responsible departments, the drug and the form of administration to be studied. This sub-module is also used by the Clinical Documentation group to review and authorize a particular study before the assignment of an identifying number.

The second sub-module is Administration, which is used to define the method of tracking progress through the study and to assign internal and external personnel/organizations to the project. If a study is to be discontinued, this module is used to indicate that change in status. The third sub-module is Design, which is used to define a set of parameters that apply to the entire protocol. These include: study population; clinical indications for the study; valid reason for excluding test subjects both before and after screening; information to be tracked throughout the study; planned subject visits and procedures to be applied during those visits; medications to be tested primarily, comparatively and concomitantly.

The fourth sub-module is Study Planning, which is used to define the planned tasks and events of the study, including their expected start, completion and duration. These are tasks and event milestones that are to be tracked on a high level, and others to be tracked on the site level. The fifth sub-module is Study Tracking, which is used to track progress against the Study Plan and to make adjustments to tasks and events that have not yet started.

4a. Protocol Number Request Sub-Module

A typical process flow within the protocol module starts with the request for a Protocol Number. The request is entered online and submitted for review by the Clinical Documentation area, which either returns it for deficiencies or approves it and assign it a Protocol Number. The user would next prepare a "draft" of the study, alternating among the Administration, Design and Study Planning sub-modules. Although it is possible that all the information for the protocol could be worked out on paper and subsequently entered into these sub-modules, the desired approach is to have the information entered as it becomes available and to use the sub-modules as tools for developing the details of the plan. With this approach the user might start entering some of the static information for the protocol and identify the core team in the Administration sub-module. This team would meet to determine the appropriate Study Objectives, Study Population, Subject Eligibility and Discontinuation qualifications, additional Medications to include, medical Procedures to be provided and when during the study they should be administered. This information would be entered in the Design sub-module and might affect the Personnel and External Organization information entered in the Administration sub-module. This information might next be reviewed with respect to the project plan for the Study, including project milestones and tasks to be performed on both the overall protocol and site levels. This information would be entered in the Study Planning sub-module and might require entries in the Administration sub-module with respect to the use of the "Event Manager" to assist in the tracking of progress. This process can be repeated interactively until the plan is determined to be correct, at which time an authorized member of the team would "Approve" the protocol plan and eventually "Finalize" the protocol study itself.

If, subsequently, a change is determined to be necessary, the protocol could be modified. If this was a change to the basic protocol information (maintained in the Administration and Design sub-modules), the protocol itself would be placed in an "Amendment in Process" status until the changes were completely entered. Once the changes were complete, the status would be changed to "Amended". If this was a change to the protocol plan, then the plan would be placed "In Revision" so that it could be changed. When completed, the plan would be assigned "Revised" status. Once the trial has started to be executed or completed, the plan status would be available for review and update through the Study Tracking sub-module.

Within the system, the Protocol Request initiates the whole process of managing and tracking clinical trials. It is basically a request for an official Protocol number, making it an official activity of the company. The main system screen is shown in FIG. 4. Clicking on Modules, then Protocol, and then Request brings up a list of existing Protocols that concern the user, either because he requested them, he is named as an investigator in it or he has system administrator rights.

This screen also allows the user to request a new number by clicking on the New button to activate a new Protocol Number Request Details screen (FIG. 5). The Protocol Number Request Details window is used to: (a) enter the data for a new Protocol Number Request and save it, (b) enter the data for a new Protocol Number Request and to submit it for approval, (c) review information on a Protocol Number Request that was previously submitted, (d) approve or return a Protocol Number Request that was submitted, (e) change information on a Protocol Number Request that was returned unapproved and save it, and (f) change information on a Protocol Number Request that was returned unapproved and re-submit it. When used to create a NEW request, correct a request that has a status of RETURNED or to change a saved request that has a status of NEW, this window allows the user to enter valid values for each of the data fields by comparing them to values stored in data tables. The field data entry process is supported by "type ahead" and "query" functions. A scrollable free form text icon permits the inclusion of lengthy comments with the request.

When used to review a request with a status of SUBMITTED or ASSIGNED, all fields are protected from change. When invoked by the user responsible for approving requests (the system user assigned the role of maintaining clinical documentation), this window only permits the option to change the status of a SUBMITTED request to either ASSIGNED or RETURNED, and to add explanatory text to the comments field. Requests having any other status may only be reviewed, all fields being protected from change.

This module uses application security to limit the functions available to a particular user. A typical user may create and SUBMIT a new request or change a RETURNED request for which he was the "Requester." A user with authority to approve a request can ACCEPT or RETURN a request, but may not modify any of the fields in the request, other than to add a comment concerning the reason for returning the request.

When the request has been completed, it can be saved by clicking on the save icon. This window can be closed by clicking on the close icon. It should now appear in the list. Double clicking on the newly created protocol will submit it for approval. A protocol number should subsequently be issued. If there is some reason a number cannot be given, a message box will appear with a comment explaining why it cannot be granted.

4b. Protocol Administration Sub-Module

Once a protocol number has been assigned, the protocol has the status of a concept. Before any planning and tracking can take place, more information is needed. This is provided through the Protocol Administration screen or window (FIG. 6). This window is selected on the menu Modules—Protocol—Administration. In effect, the Protocol Administration window and its associated tabs are used to collect high level planning information about the protocol, including the current status of the protocol and the study, as well as Therapeutic Teams, Personnel and External Organizations that will be participating.

The Protocol Administration header is used to select the protocol that is to be acted upon. Once the protocol is selected, the system will determine if the logged on user has been given write access to the protocol and will display the fields on the tabs as protected (no write access) or unprotected (write access).

The Administration tab of the Protocol Administration window collects information about the protocol. This includes the personnel who will be working on the study at this level, and the external organizations participating at this level.

This window can also be used (a) to change the protocol status from "Concept" to "Finalize" (locked from further change) once the Design and Study Planning modules have been used, (b) to amend a protocol (make changes to the protocol design) after it has been finalized and finalize the amendment, and (c) to lock that amendment from additional changes. However, multiple amendments can be made to the protocol.

In addition to changes to the protocol status, the study status can be modified, but only once the "Event Manager" function has been deactivated. The list of available choices for study status is limited by the current saved value of that field. In this way the user is prevented from selecting a status that would logically precede the current one.

The decision to manually track a project or to use the Event Manager must be made while the protocol status is "Concept." The user is programmatically prevented from deactivating/reactivating the Event Manager. When the Event Manager is active, the study status will be programmatically updated.

The Notification field may be used to indicate certain key events that have significance, such as "Canceled", "Enrollment Stopped", "On Hold", "Resume Study" and "Terminated." These selections are limited by the current value of study status such that "Canceled" will be displayed only for a "Study Status" of "Planned" or "Initiated; "Enrollment Stopped" and "On Hold" will be displayed for a "Study Status" later than "Screening Ongoing; "Terminated" will be displayed only for a "Study Status" of "Enrollment Complete" or later; "Resume Study" is available in all "Study Status" stages, however when it is selected the Notification field will be appear empty, rather than contain the words "Resume Study." Once a protocol has been canceled or terminated and this value has been saved, no other "Study Status" may be re-assigned to the protocol.

The Personnel tab of the Protocol Administration window is used to record all the employees associated with the study at the protocol level, as opposed to the site level. The Protocol Requester and Project Physician (entered in the original Protocol Request) are automatically added to this list as active personnel and granted write access to the protocol by default. In addition to identifying the employees, their status and write abilities are set. Further, the screen displays their responsibilities and phone numbers. When an employee is no longer associated with the protocol, this window can be used to deactivate them, removing their write access (if any).

There are special processing rules for this window. In particular, the access, responsibility, and active date belonging to the currently logged on user, can not be changed. Write access authority can not be removed from an active Project Physician. At least one active Project Physician is required for the protocol. Also, at least one person on the project must have write access. The same employee can not be active in the same protocol more than once, and a previously deactivated employee may not be re-activated. Finally, the Inactive date must be greater than the Active date.

Figure 7:
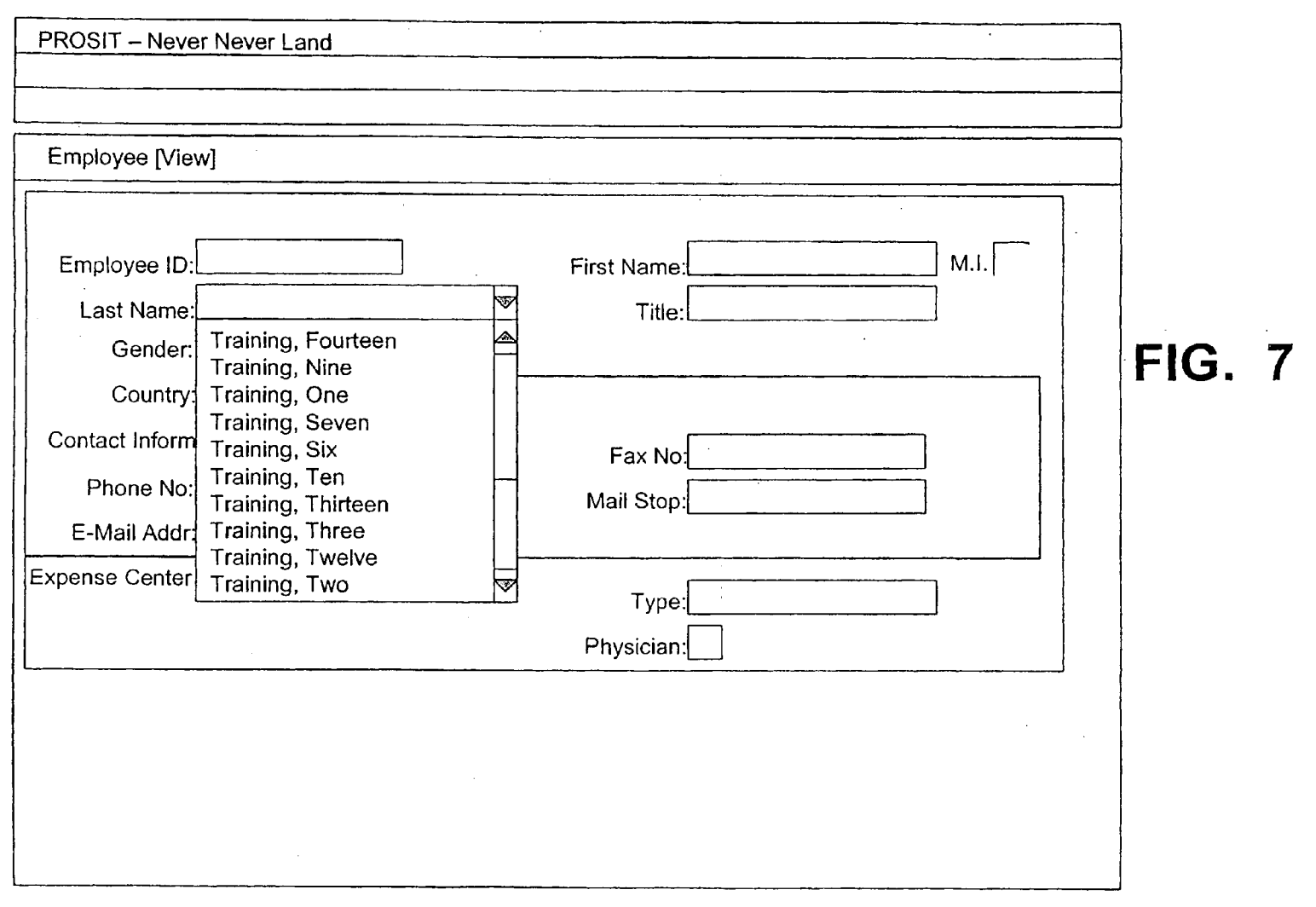

In the Personnel tab, the names of addition people can be added. By going to the Module—Country Administration—Employee level on the drop down menu, access is provided to a list of all past and present employees. Any of these can be incorporated into the personnel of the study. An Employee Roster screen (FIG. 7) allows a search for employees by their last name. The other fields contain relevant information about that selected employee.

The External Organization tab is used to record certain organizations that will participate in the study but which are not part of the company, e.g., a hospital. This tab not only shows the companies available to work on the study, it gives the contact person at each.

4c. Protocol Design Sub-Module

Selection of the items Modules—Protocol—Design on the drop down menu provides the Protocol Design screen (FIG. 8). The Protocol Design sub-module is used to record details regarding the design of the study. There details include such information as the drugs and dosages to be used, the objective and design considerations of the study, the tracking details used in the Site Contact sub-module, the reasons for subject ineligibility and discontinuance from the study, and key information to be gathered from the subject at each visit. However, the most important feature is that this module allows the user to schedule the visits as well as the procedures or treatments which make up the study. This information is displayed in a Visit Map or study flow chart (FIG. 10).

Once the protocol number is selected or entered in the Protocol Design screen, various pieces of previously entered information populate the screen. In the upper part of the screen a more detailed working title can be provided. Further, the primary indication can be inserted from a drop down list of industry standard terms. If the user is not aware of the code, the Search List or a Query option can be used to locate it. Similarly, the Study Population and other information can be filled in. There is a space at the end for a synopsis of up to 2000 characters to explain the purpose of the protocol.

The next tab on the screen, Medication, provides the location for inserting information about the medication involved in the protocol and the dosage instructions (FIG. 9). The primary drug indicated during the protocol number request, will automatically appear on this screen. This drug and its role cannot be edited, but other drugs can be added as concomitants or comparatives using drop down menus on this screen. The test drug within a protocol can have various different dosage details as created on this screen.

However, the multiple dosage instructions as well as the lists of the concomitant or comparative drugs can only be performed when the protocol status is "CONCEPT" or "AMENDMENT IN PROCESS". Each drug can appear only once in the protocol.

Before another drug can be added to the protocol, the data for the current drug must be saved. Once a drug has been added, the drug selection can not be changed. However, the role of the drug can be changed between concomitant and comparative or the entire drug can be deleted and re-added. If a drug is deleted from the protocol, then all its dosage instructions are deleted. Individual drug dosage instructions can be deleted and added. However, the drugs and dosage instructions can not be added/deleted when the status of the protocol is "FINALIZED" or "AMENDED".

The next tab is the most important Visit Map (FIG. 10). The Visit Map tab allows the user to enter the number of visits a subject will be required to make, and when they will take place. The information is linked to the procedures that are expected to occur at each visit. This in turn will facilitate the recording of subject visit information.

In addition to selecting the number of visits by the number of rows activated, each visit is provided with a visit ID and is labeled. Further, the study phase for that visit is selected from a drop down list and the ID of the visit that proceeded it (Prev. Visit ID) is indicated. Further an indication is made of the time period in which the visits are to occur and one visit is identified as the subject enrollment visit.

Figure 11:
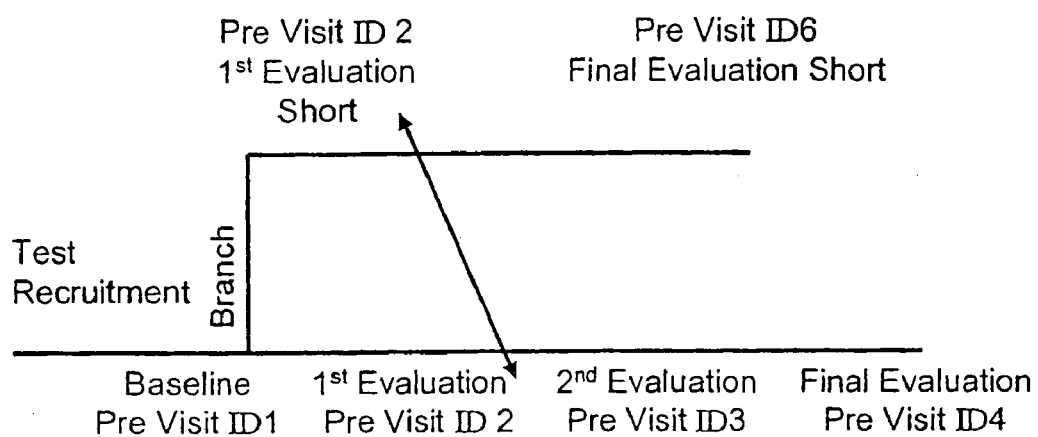
FIG. 11 is a visual representation of a visit plan with a branch.

Most protocols will have a straight visit map with one visit always following another. However, sometimes a protocol may require branching, where based on some criteria, subjects diverge with some following one schedule and others following another schedule. This is handled on the Visit Map by giving two visits the same Prev Visit ID. FIG. 11 is a visual representation of the visit map created with a branch that occurs because the $1^{st}$ Evaluation and $1^{st}$ Evaluation Short share the same Prev. Visit ID.

At the Procedures tab (FIG. 12), the medical procedures associated with a particular visit in the protocol are assigned. These procedures form the basis for tracking subject progress during the monitoring visits, and estimating site budgets. A separate schedule exists for each branch shown in the visit map. The selection is made by checking the box on the row for the treatment under the visit identification. First, the user selects the Treatment Schedule and this causes visit # headings to be displayed with check boxes. In the case where there is a branch in the visit schedule, adding a treatment to a common visit will add it to both schedules.

It frequently occurs that a subject must discontinue the trial. Thus, the system allows for the insertion of a Discontinuation Visit as one of the Treatment Schedules. By selecting it, the user can insert the procedures that are to be followed when a subject discontinues the trial. These procedures may include measurement of vital signs, a physical examination, an ECG, etc.

The next tab is entitled Optional Fields (FIG. 13). It allows the user to input some key subject data as part of the monitoring effort. This data collection does not replace the Case Report Form (CRF) or the Remote Data Entry (RDE) aspects of the study. Instead, it is useful to give some overall indication of the progress of the study. Reporting the results on this level throughout the full life of the protocol can serve as an early warning of both successes and failures of the protocol. It can also be used to make sure that all monitors of the clinical trial who are creating the site contacts are collecting data that can be pooled together.

The Optional Fields tab as shown in FIG. 13 is divided into two distinct areas: a Subject Optional fields and a Visit Optional field. The Subject Optional field created on this screen will appear on the Subject Visit Tracking tab in the Site Visit module. The Visit Optional field will appear on the individual Subject Visit tabs. The Subject Optional Field relates to a person who is a subject of the clinical trial. This information should be either unlikely to change during the course of the study or irrelevant if it does change, e.g., the height of the individual. The intent is that when a monitor visits a site, they can capture this information once about each subject in the study. For data validation purposes, the screen allows the user to specify the format in which the data will appear, e.g., text, a data, a number.

On the other portion of the screen under "Visit Optional Field," there are entries similar to those for a subject, except that these are available for collection each and every visit the subject makes to this site. The Visit Optional fields are used to collect significant data that is likely to change during the course of this study, for e.g., blood pressure or cholesterol level. This data may be critical for safety or continued eligibility reasons.

The next tab on the screen allows for the insertion of Subject Eligibility rules. There are many standard reasons for potential subjects being declared ineligible for a clinical trial prior to screening. This screen, (FIG. 14) allows the reasons to be set up for use in the site and subject tracking modules of the system. The reasons identified at this location, and only these reasons, will be available to monitors of the trial as options for tracking and reporting later in this study. By default, a list of standard core reasons will already be provided and can be selected from drop-down menus. Any reasons that do not apply can be eliminated, and new reasons can be inserted.

As shown in FIG. 15, the right side of the screen allows the user to insert reasons for a subject discontinuing the clinical trial once it has begun. As with the reasons for ineligibility, there are a core set of reasons from which the user can select. Further, the user can add and delete requirements to meet the specific protocol.

The last tab on this screen is the Study Objectives field, which is divided into two main sections: Special Components and Design Considerations (FIG. 16). This tab can be used to record certain information about both special components of the treatment as well as special considerations in the design of the study itself. The special components portions includes a standard listing of special components for studies. It is reached by activating the drop-down menu. There is also a drop-down list of design considerations as shown in FIG. 16. New selections can be made and prior selections can be changed or deleted.

4d. Protocol Amendments Sub-Module

Often, a change is required to the protocol after it has been finalized in the system, and usually after subjects have begun their participation in the study. Changes to the design of a protocol that has been finalized are called "Amendments" to the protocol. To reach a screen where amendments can be made, the Module—Protocol—Administration menu hierarchy is used. The screen of FIG. 17 will appear in which there are certain design fields. These design fields are considered to be "Amendment" fields and they will be tagged with the version of the amendment that changed or added them. Amendment fields require the user to have an open amendment to change them; when the status of the protocol is "FINALIZED" or "AMENDED" they become display only fields.

Not all changes to the protocol made within the system after the protocol is finalized are amendments. Information that is considered to be "administrative" and does not affect the design of the protocol will be modifiable by users with write access to the protocol, without the need to initiate an amendment.

There are some fields that have such far-reaching system effects that no user (including the World Wide System Administrator) can change them. Changes to these fields might alter the ability of the user to access the records, or have some impact on historical tracking of information within the system. These fields are considered excluded fields, which require the assistance of a system or database administrator to alter due to the potential for larger system effects upon change.

A single change in the protocol design may affect one or several modules within the system. For example, if a new procedure is added to the Visit Map, the Site Budget, Subject and the Site Contact modules will be affected. In the system amendments can only add or occasionally modify existing information about the protocol. They cannot delete information. This is to protect information that has been recorded for subjects that have already been processed by the system.

Amendments should be identified in a way that indicates the order in which they were applied. The date on which the amendment was finalized (i.e. approved for implementation) is also a key piece of information for a user. The Protocol Amendment History window will contain the "number" of each amendment, the date on which it was finalized, and a comment. Amendment information will be shown throughout the system on various windows to identify changed information to the user. Since the changes made during an amendment will have many downstream impacts, it is best to enter all amendment information during one session.

Amendments can be accepted at each study site at the Site Administration—Administration menu location, when the site is ready for the changes. Any optional fields, reasons for eligibility, and reasons for discontinuation added during an amendment are reflected at the site as soon as the data is saved (and replicated to the subsidiary, if applicable) regardless of the accepted site amendment. Only amendment changes to the Visit Map and procedures are reflected in the acceptance of an amendment at a site. When the site accepts an amendment, the changes made to the Visit Map and procedures will affect the Site Budget Subjects Costs and Subject Visit Tracking. Since it is up to each site individually to accept an amendment, all sites may not be at the same amendment at a particular point in time. This accurately reflects the business, where separate Institutional Review Board ("IRB") approval may be needed implement changes in the design of a study. A site may choose to skip over an amendment, but doing so will bring all amendment changes that have occurred during and prior to the accepted amendment down to the site (e.g., accepting amendment 3 would be the same as accepting amendment 1, then amendment 2, and then amendment 3).

During an amendment, entirely new visits or even new treatment schedules may be added to the protocol design. Additional procedures may also be added to the Visit Map. Once an amendment is finalized and accepted at the site, these additions will appear in the Site Budget, but only when the budget has a status of "Draft" or "In Revision." Data for these additions can then be added to the Site Budget. Any new treatment schedules will be available for selection. The subjects budgeted for all new visits will be blank and available for entry. The cost fields for all new procedure visits will also be blank and available for entry individually.

Once an amendment is finalized and accepted at the site, new visits will appear in the visit pick list (which is accessible under Subject Visit Tracking—Subject—Create a New Visit menu) as options for the monitor in recording the visits that took place. The Site Amendment Effective Date and amendment label are displayed on this screen to assist the monitor in accurately identifying which version of the protocol design was followed for this visit of this subject.

New procedure visit intersections will appear in the "To be paid" section on the Visit tab (under Subject Visit Tracking—Visit number). Procedures that were added to the visit during an amendment that is effective after the visit date will be displayed in blue. Individual procedures include the amendment label under which the procedure was first added to the protocol. The user can un-check a now exempt procedure for any particular visit that was added to the protocol after the subject has already had the visit.

5. Study Planning And Tracking Module

The Study Planning process makes use of two modules of the system, the Milestones Module and the Protocol Module. Study Planning is the portion of the system that supports development and maintenance of Task Lists, which are then used for the planning and tracking of clinical studies. The Milestones Module would typically be used by the World Wide System Administrator and Local Administrators, whereas the Protocol Module would be used by the Protocol Requestor and the Project Physician. The Protocol Module can also be used by those designated by either the Requestor or Physician to be able to maintain the Protocol information.

5a. Milestones Sub-Modules

The Milestones module consists of three (3) sub-modules. The first sub-module is Master Tasks, which is used to add, change and maintain predefined tasks that may be used by every Study Plan, Site Plan, Template and the Core Task/Core Site Instruction lists. This module can only be used for update by the World Wide System Administrator. However, all other users can use it to view the Master Tasks list. The second sub-module is Core Tasks, which is used by the Local Administrators to define a country specific list of tasks that are to be included in every Protocol Study Plan and Site Study Plan for that country. The third sub-module is Templates, which is used to define sets of country specific models for Study Plans and Site Instructions. Templates are used to "jumpstart" the development of Study Plans by providing a list of tasks with some generic planning already included.

Since the Milestones module is not subject to a large number of updates, the "typical" use is to initially set up the Master Task List and to establish the Core Task/Core Site Instruction Lists and Templates. This latter action is carried out by the Local Administrators. The World Wide System Administrator would start by entering (or importing from an external source) the names of tasks, whether or not they are going to be tracked by the Event Manager, and whether or not the task should be treated as a Milestone event. Once the required tasks have been added to the Master Task list, the Local Administrator identifies those tasks that should be part of every Study Plan and Site Study Plan for their country, as well as the order in which they should initially be presented when creating a new template.

After the Core Tasks and Core Site Instructions have been defined, the Local Administrator for the country creates several templates. These templates are used when Study Plans and Site Instructions are created for a protocol, but only if they are created by a user with the same context country as the Local Administrator. The planer of the Study Plan and Site Instructions for the protocol uses the Study Planning sub-module of the Protocol Module. When first executed for a protocol, a list of the available templates for the context country is displayed. The planner reviews the tasks, adding new tasks and removing unwanted ones (template tasks and milestones can be deleted; core tasks, on the other hand can not), re-organizes the sequence of events, creates task dependencies, defines Milestone events and adds start/end dates and task duration.

For "International Protocols," i.e. protocols which are originated in the main country of the company, e.g., the United States, but have one or more sites in other countries, the Site Instructions entered in the Unites States Study Plan are propagated to the Site Instructions of each of the other countries participating in the protocol. Thus, the planner of that country's Study Plan will see not only the Site Instructions for the template that he has chosen, but a set of additional Site Instructions coming from the main company system, e.g., the United States, study plan.

Once execution of the protocol plan has started, status is reported on the site and study level, through the Site Study Tracking sub-module of the Site Module, and the Study Tracking sub-module of the Protocol Module. If the Event Manager is being used to track the progress of the plan, then information will roll-up from the site study plan level to the country protocol study plan level. In the case of an International protocol, it will roll-up to the originating protocol plan as well. The Protocol Manager (or his designee) uses the Study Tracking sub-module to review the current status of the clinical trial and to modify dates and durations. If additional tasks need to be added to the Study Plan or Site Instructions, he will use the Study Planning sub-module to place the plan "In Revision," make the changes to the Study Plan, and accept the changed plan as "Revised." The system will propagate the changes down to the distributed copies of the Study Plans and Site Instructions. This could conceivably take place several times during a project, but it is unlikely.

Similarly, the Local Administrator may make changes to the Core Task requirements for the country. Should this happen, the tasks are propagated to those templates, study plans and site plans which are currently active.

Selecting "Modules" on the main menu allows for the selection of "Milestones" in which the sub-menus are Master Task, Core Task and Templates. A Milestone is essentially a reference point marking a major event. The Milestone's module and the Protocol Study and Tracking module allow users to create a realistic schedule for the study plan. Through updates by users as well as updates through the "Events Manager", the actual progress of a study can be monitored against the original plan and latest estimates. As shown in FIG. 18, the Master Task List is a storage place of all possible tasks that are associated with preparing, conducting, registering and tracking a clinical study. This list drives the entire Milestone module. All tasks, except those defined by the user, must exist in the Master Task List in order to be used in other parts of the system. The Master Task List is read-only to general users and can only be modified by the World Wide System Administrators. As shown by FIG. 19, the Core Task List, which is reached in the same way as the Master Task List, is a set of mandatory tasks that need to be tracked in all protocols in a subsidiary or country. Core Tasks are selected from the Master Task List and are maintained by the Local System Administrator. This List generally can not be changed. Each country will have it's own country-specific set of Core Tasks, each subsidiary will be able to select tasks according to their own local needs.

There is a difference between tasks that are Milestones and tasks that are Activities. An example of the distinction between a Milestone task and an Activity task is that when a task is used in a template or in the process of study planning, an activity task can have a duration assigned to it while a milestone task always has a duration of zero.

The Core Tasks are separated by type, (i.e., "Summary", "Simple" and "Event Manager Simple") and do not have any additional data items associated with them. When a Core Task is added, removed or modified, the change is propagated to all templates since the templates by definition include all of the Core Task. Changes to the Core Tasks are propagated to plans that have previously been created. The set of Core Tasks available to a user is determined by the context country at the time the program is used.

On the same window as the Core Task, there is a Core Site Instructions tab (FIG. 2). This is used to maintain a list of Site Instructions for each country. This list must be included in every site study plan for studies conducted in the country with which the list is associated. The tasks on these list are selected from the Master Tasks List and are filtered through "Simple", Automatic roll-up", and "Manual Roll-up" task types. They do not have any additional data items associated with them. These tasks can not be deleted from a site plan once the plan is created. When a Core Site Instruction is added, removed or modified, the change is propagated to all templates, since the templates by definition include the Core Instructions.

The last major sub-module is Templates, which can be reached in the same manner as the other sub-modules. Templates, as discussed above, are a pre-defined group of tasks, outlined activities and Milestones set up for a therapy group by the System Administrator for creating study plans or protocols. The core tasks are used to create a base for all templates. Once developed the template can be used again and again with the same group of tasks, outlined activities and milestones. If any core tasks are added or deleted, all templates will be properly updated. These templates are country-specific to allow for customization based on the unique requirements in each country or at each subsidiary.

Once a template number is selected, a sequence of tasks is displayed as shown in FIG. 21. Each task in the template has the number of days or duration planned for the tasks associated with it. Users can also organize a template as an outline effectively creating parent-child relations between tasks. Parent Tasks are used to group a number of detailed tasks and show a summary of tracking information for the group. As shown by FIG. 21, there is a Site Instructions tab on the same screen. Activating this tab gives a list of Site Instructions related to the template.

5b. Study Planning Module

The Study Planning Module, is the place where a template is selected and additional tasks are added to help track the actual progress of a study. It is found by clicking on the Modules-Protocol-Study Planning drop-down menu hierarchy. A screen appears in which a protocol number can be inserted or displayed with a drop-down arrow. Next the drop-down arrow beside the country field is selected and the country is chosen. The plan status is entered in a similar fashion. If draft is selected as the plan status, a dialogue box will appear with a list of different templates, which have names which generally refer to the conditions that will be studied. This is shown in FIG. 22. When a particular template is selected in this way, the screen of FIG. 23 appears. The plan elements may be either "Tasks" (a unit of work having a duration greater then 0) or "Milestones" (a marker of a point in time or an event).

The Protocol Projections tab (FIG. 23) allows overall projections for the protocols to be entered. This includes the number of subjects and number of sites, sites per monitor, etc. This screen on the right hand side, also allow the opportunity to designate the monitoring countries in which the sites will exist, and how many there will be for each monitoring country. The second tab on this screen reveals the Study Planning screen (see FIG. 24). The study planning window is used to create the task plan for a protocol, enter estimates of dates, duration and Milestone events, revise the plan and reported tasks/event status and completions. Some tasks created on this window need to be grouped together in logical groups of high level activities and lower level tasks. This is accomplished using the indent function. Each low level task can have effort, duration, delay and dependencies applied to them. When entering this information, a number of interactions can take place that can change the values of prior or subsequent tasks. These interactions can result in error messages for illogical conditions, the removal of predecessor links, changes of dates in the current tasks, changes of dates in the predecessor tasks or changes of dates in successors tasks.

A predecessor is the establishment of a link between tasks in the plan. When tasks are linked, a relationship between their start and finish dates is defined, which tells the system that one task can not start until all of the tasks are completed that this task is depended upon. A successor is the other side of predecessor. Once a predecessor occurs, the successor can begin.

As new tasks are entered they appear at the bottom of the list. However, they can be moved through a cut-and-paste operation. The indents are left and right arrows on the tool bar. If in filling out the study plan a date is needed, double clicking in the blank space will cause a calendar to appear on which the date can be selected. Dates can also be automatically calculated, e.g., by entering a specific number of days in the planned field and an end date, the start date will automatically be calculated.

A Study Management Plan ("SMP") study plan tab is available under certain circumstances where the protocol is international. Multiple countries need to have been assigned to the protocol and the countries selected by the user must not be the main corporate location, e.g., the United States. This tab is used in subsidiary countries to view the high level SMP created at the main office. No changes to data can be made from this tab. A picture of the screen is shown in FIG. 25.

Under the same conditions the SMP site instructions screen is also available. This screen is used by subsidiary countries to view at the high level the site instructions list created at the main database. It can not be changed. Under normal circumstances, however, a conventional Site Instructions tabs is the only other available tab (see FIG. 24). The site instructions tab is used to identify tasks that are mandated for reporting and tracking. This tab is initially populated with Core Site Instructions (tasks that all sites reporting to the protocol must track, no matter where the sites are located.) For an international study, the core tasks module will compare the list of site instructions in the headquarters and subsidiary plans, and create a single list of Core Site Instructions for the sites.

Once this tab is populated with this base line of tasks, additional site instructions can be added. Tasks added here will be copied to all the sites under the protocol. If the task is added from the Master Task Table and is defined there as a Milestone, it will also be locked as a Milestone in this tab. Tasks can be manually added and deleted while the plan status permits updates. Once the plan is completed it can be approved by clicking on Actions and then clicking on Approved and finally clicking on the Yes button that will appear. Similarly, by clicking Action on the menu and then clicking on Revise, the plan can be sent back to a draft or an amendment mode in which it can be revised.

Drag and drop capability is provided in the Study Plan to allow rearrangement of entries as necessary. Predecessors are established by placing the cursor in the predecessor column and entering the sequence number of a task directly above. If you enter the correct number in the predecessor column, it will link to the task to be completed. Further, in creating the plan, a delay can be added to task. If a delay is added, the system can use the delay when it calculates the start date of the task.

By click on the "Modules" item of the menu and on "Protocol", you can reach Study-Tracking. The Study-Tracking module is where the actual dates are entered as soon as the task is completed or updated. This module may also have entries made by the Event Manager.

6. Event Manager

This module is used to support the requirement for the system generated updates to the system summary and system roll-up tasks. The objective of the Event Manager is to determine when an "event," or change to the system, has occurred that impacts another area of the system. The system determines how to process the events through the use of database triggers and stored procedures.

The Event Manager is a process to roll up site activity to represent a protocol's progress. This process automatically rolls up Milestone information and adjusts study and site status information based on the actual information and workflow activity occurring in the system. Roll-ups are implemented as interactions between plans in the system. At the highest level, a protocol plan lays out the tasks for an entire study. Then each subsidiary participating in the study can have its own country or subsidiary level plan. Finally, at the lowest level, each Site participating in the study has a Site Plan. The majority of roll-ups are Site to protocol and Site to Subsidiary. A subsidiary event may change the protocol Status.

The user can opt, when developing their protocol, to deactivate the Event Manager by un-checking the 'Event Manager Active' check-box on the Protocol Administration screen. The user may turn off the Event Manager only when the Protocol Status is "Concept", the Study Status is "Planned", and Notification is "On-going". If this option is chosen, all updates are completely manual and set by the user. In order to realize the full power of the system, and to assure the most accurate data, the Event Manager active check-box is defaulted to checked.

There are two types of events that the system processes. The first is system driven events. These are events that occur outside of the study plans. The events are the planned/protocol number assigned, the protocol approved, initiated/first site initiated & site initiated, last site initiated (to date), screening ongoing; first subject first visit, enrollment ongoing/first subject enrolled and site closed. The second are Milestone driven events. These are events triggered from within the study plans and may or may not effect other areas of the system. These events are initiated/first site initiated & site initiated, last site initiated (to date), screening ongoing/first subject, first visit, enrollment ongoing/first subject enrolled, enrollment complete, clinically complete, all data in-house, data cleanup complete, database locked, CSR complete and site closed.

To understand this, some key definitions are needed as follows:

"Planned"—A protocol number has been granted and the protocol document is in the concept stage.

"Protocol Approved"—The protocol has been finalized and approved by the appropriate staff.

"Initiated/Site Initiated"—means a site under the protocol was visited by a study monitor for the purpose of conducting the study initiation visit.

"Screening Ongoing/First Subject, First Visit"—means the first subject at a site under the protocol has completed a visit for possible inclusion in the study.

"Clinically Complete"—means all subjects at all sites under the protocol are going to have no more planned study visits.

"All Data In-house"—means all case report forms for a site have been collected and returned to the main monitor.

"Data Cleanup Complete"—means all data exceptions have been resolved and entered into the database.

"Database Locked"—means all data has been entered, and no more changes will be made to the database.

"CSR Complete"—means the "Clinical Study Report" is final and was signed by all appropriate staff.

"Site Closed"—is a special status for a site and it indicates that the study closeout visit has been made to the site for the protocol.

"Study Notification"—a special status that can occur at various times throughout the study which indicates a disruption of the project life cycle, and which generally has effects on the continuance of the study in general and at all sites. Notifications are set independently of the study status. However, there are rules that will be applied for selection and removal. The Protocol notification status will be set at the protocol level and will be displayed at the protocol's sites.

When the Event Manager is active, the protocol or site could be under a notification, while the study status continues to change automatically as data is entered into the system. For example, if the study notification is changed from "Ongoing" (the default) to "Terminated", the study status could still move through the hierarchy from "clinically complete" to "CSR complete", as driven by the Event Manager and the Milestones plans.

There are various Event Manager task types. They include, "Manual Roll-up" tasks, which are site instructions which trigger an update to the site status when an actual date is manually entered by the user on a site plan. "Automatic Roll-up" tasks are site instructions which trigger updates to both the site and study status. When these events are captured by the Event Manager, the actual start and end dates for the corresponding task in the site plan is updated. Additionally, the actual start and end dates for the associated summary task in the subsidiary and protocol plans may be updated.

"Summary Tasks" are protocol and subsidiary level master tasks whose actual start and end dates are updated when the associated roll-up level task is updated on the site plan by either the user or the Event Manager. "Event Manager Simple" tasks are protocol level master tasks which in most cases trigger an update to the study status when an actual date is manually entered by the user on the protocol plan. The event related to a particular task will trigger an update to the actual start and end dates or a particular task in the protocol plan when the event (such as approving a protocol number request of finalizing a protocol) is captured. The Master Tasks are a set of tasks that are mandatory in various plans and a subset of these tasks are an integral part of the Event Manager processing.

Figure 26:
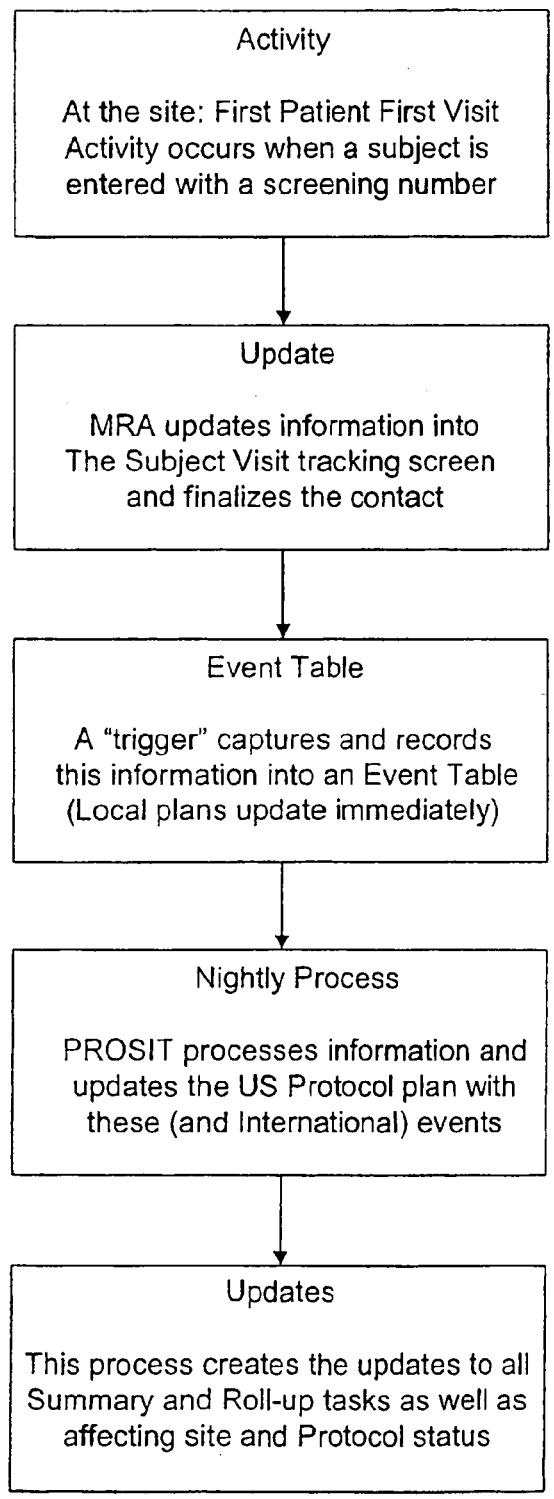
FIG. 26 is a diagram of a simple operation in the Event Manager.

FIG. 26 is a diagram of a simple operation in the Event Manager. FIGS. 27a–27i are flow charts of the various automatic operations of the Event Manager.

FIG. 27a shows the operation of the Event Manager with respect to the assignment of the protocol number. As soon as a request for a protocol number is sent, step 100, the Event Manager creates a draft protocol plan, which includes a root task and protocol number assigned task. The system date on which the protocol number was assigned will be inserted in the planned, latest estimate, and actual start and end date fields for both tasks. The duration of both tasks will be set to zero and the "Protocol Number Assigned" task, duration and date fields will be locked from user update. At this point the process stops.

As shown in FIG. 27b, once the details of the protocol are completed, the user will take steps to finalize the protocol, including entering the date on which the protocol is considered finalized. When the protocol finalize date is updated for a protocol, a determination is made in step 102 as to whether there's an update from replication or a snap shot refresh. If there is, the process is exited. If there is not, the Event Manager will set the actual start and end dates for the Final Protocol Date in the protocol plan, sets the task duration to zero and locks the task from user update, step 104. If the Event Manager is not activated, the user will enter the actual start and end dates for the Final Protocol Date.

The operation of the Event Manager when the first site and subsequent sites are initiated is shown in FIG. 27c. The Event Manager is triggered when a site contact is finalized, step 106. This is achieved by making a determination whether a visit contact with the reason "study initiation" for a site has occurred. If it has not, the process is exited. If it has, all finalized study initiation visits for the site will be scanned for the minimum site contact date. This date will be inserted into the actual start and end date fields in the site study plan for the task called "site initiated." The duration of the task will be set to zero and the task, duration, and date fields will be locked.

The Event Manager will roll this information up to the subsidiary plan level only for sites within the subsidiary and will compare the minimal date for the task called "site initiated" across all site plans. Once identified, this minimum date will be updated in the actual start and end date fields in the subsidiary plan for he task called "First Site Initiated." The duration will be set to zero and the relevant fields locked. Finally, the Event Manager will roll this information up to the protocol plan level for all sites and will compare the minimum date for the task called "site initiated" across all site plans. Once identified, this minimum date will be updated in the actual start and end date fields in the protocol plan for the task called "First Site Initiated," the duration will be set to zero and the relevant fields locked. The Event Manager will also check and correctly set the study status field.

A determination is made in step 108 as to whether the protocol is an international protocol. If it is not, the site plan, site status protocol plan and study status are updated in step 110 and the process is exited. If it is an international protocol, a determination is made in step 112 as to whether an update has occurred on the protocol owning the server (i.e., the server on which the protocol was created). If there has not been, then the site plan, site status and subsidiary plans are updated in step 114 and the process is exited. If there has been an update of the protocol, determinations are made in step 116 as to whether the update came from replication. If it did not, then the site plan, site status protocol plan and study status are updated in step 118, and the process is exited. Finally, if the update did come from replication, the job is submitted to update the protocol plan and study status in step 120.

If the Event Manager was not activated, when the user enters the actual date for the task "Site Initiated" in the site plan, he must also change the status to "initiated."

A Milestone driven event for initiating the first site, screening the first subject's first visit, and enrollment of the first subject are shown in FIG. 27d. First, the user enters an actual date for a task (e.g., "Site Initiated") in the site plan in step 122. The entry could also be the entry of the actual start and end date for the task called "First Site Initiated" in the protocol plan. The trigger event could also be the screening of the first subject at the first visit and the enrollment of the first subject. In any event, based on these trigger events, the Event manager continues with updates to the subsidiary plan, protocol plan and study status as indicated above. In particular, a determination is made as to whether or not an international protocol is involved in step 124. If the answer is no, the site status protocol plan and study status are updated in step 126, and the process is exited. If it is, then a determination is made as to whether an update has occurred on the protocol owning server in step 128. If the answer is no, the site status and subsidiary plan are updated, and the process is exited in step 130. If the update did occur on that server, a determination is made in step 132 as to whether the update came from replication. If the answer is no, the site status plan, protocol plan and study status are updated in step 134, and the process is exited. Finally, if the update did come from replication, then the protocol plan and status plan are updated in step 136 and the process is ended.

If the Event Manager is inactive, the user will enter the actual date for the task in the plan and change the status manually.

For the case where the event is system and milestone driven for a last site initiated, the process of the Event Manager is shown in FIG. 27e. The Event Manager is triggered when a visit contact with a reason of "study initiation" is finalized. When this happens the Event Manager will scan the site plans of all sites monitored by the same subsidiary. The maximum end date of the task called "site initiated" will be selected. This date will be inserted in the actual start and end date fields in the subsidiary plan for the task called "Last Site Initiated (to Date)," the duration will be set to zero and the task, duration and date fields will be locked. The process will then roll this information up to the protocol plan level for all sites and will compare the maximum date for the task called "site initiated" across site plans. Once identified, this maximum date will be updated in the actual start and end date fields in the protocol plan for the task called "List Sited Initiated (to Date)," the duration will be set to zero and the fields locked.

This process begins with the finalizing a visit contact and the entering of an actual date for a task in the site plan. A determination is made in step 140 as to whether the reason for the contact was study initiation. If it is not, the process ends. If it is, a determination is made in step 142 as to whether it is an international protocol. If it is not an international protocol, the protocol plan is updated, and the process is exited. If it is an international protocol, a determination is made as to whether an update occurred on the protocol owning server in step 146. If it is not, then the subsidiary plan is updated and the process stops. If it is, a determination is made in step 150 as to whether the update comes from replication. If the answer is no, the protocol plan is updated and the process ends. If the answer is yes, an update is made to the protocol plan in step 154.

When a subject has completed a visit for possible inclusion in the study, they are considered screened. Where the event is on-going screening of a first subject during a first visit the process is as shown in FIG. 27f. There are three methods that the Event Manager can use to automatically determine when the status of a site and study should be set to "Screening Ongoing."

The first method can only occur when subject-visit level tracking is being done. When a new subject is created, a screening number is assigned and a visit can then be created for the subject. The Event Manager will be triggered when the visit contact is finalized. If the visit date for this or any subject's first visit was entered into the finalized contact, the Event Manager will update the site status to "Screening Ongoing." The Event Manager will then scan for the minimum first visit date of all subjects for the finalized contact. This date will then be inserted in the actual start and end date fields for the site plan task called "First Subject Screened." The duration will be set to zero and the task, duration, and date fields will be locked from user update.

The Event Manager will then roll this information up to the subsidiary plan level only for sites within the Subsidiary and will compare the minimum date for the task called "First Subject Screened" across all site plans. Once identified, this minimum date will be updated in the actual start and end date fields in the subsidiary plan for the task called "First Subject First Visit." The duration will be set to zero, and fields will be locked.

Finally, the Event Manager will roll this information up to the protocol plan level for all sites and will compare the minimum date for the task called "First Subject Screened" across all site plans. Once identified, this minimum date will be updated in the actual start and end date fields in the protocol plan for the task called "First Subject First Visit," the duration will be set to zero and the fields will be locked. Also, the Event Manager will update the study status to "Screening Ongoing."

The second method, like the first, can only occur when subject-visit level tracking is being done. As above, when a new subject is created a screening number is entered, the Event Manager will be triggered when the visit contact is finalized. Because there is no first visit date associated with this occurrence, the Event Manager can only alter the site and protocol status, changing them to "Screening Ongoing" (following the appropriate hierarchy rules).

The third method that will trigger the Event Manager is when a number greater than zero is entered in the site-tracking window (re: site tracking, enrollment tracking) for the field called "Number of subjects screened" for any "as of date" in any visit contact that has been finalized. Because there is no appropriate date associated with this occurrence, the Event Manager can only alter the site and protocol status, changing them to "Screening Ongoing" (again, following the appropriate hierarchy rules).

This process is accomplished according to the flow chart of FIG. 27f by making a determination in step 160 as to whether screening numbers were created. If they were not, a determination is made in step 162 whether there has been entered a value for the number of subjects screened. If not, this protocol ends. If there has been, the series of decisions concerning an international protocol (step 164), an update occurring on the protocol owning server (step 166), an update coming from replication (step 168) are made and processed as in FIG. 27e and which results in updating the site status and study status respectively in each of steps 170, 172 and 174.

Returning to step 160, if screening numbers have been created, a determination is made in step 163 as to whether the date of the first visit has been entered. If it has not the process branches to the sequence of steps 164 through 168. If the date of first visit is entered, then a sequence of steps of 164', 166', 168' are entered which are equivalent to steps 164 through 168. However, each of these decisions triggers steps 180, 182 or 184, respectively, which instead of updating a status as in steps 170–174, update the site plan, site status, protocol plan, study status and subsidiary status as shown in the figure.

The ongoing screening is also Milestone driven when the user enters the actual date for the task called "First Subject Screened" in the site plan. When this happens, the site status will be set to "Screening Ongoing." The Event Manager will then continue with the updates to the subsidiary plan, protocol plan, and study status as above.

The Event Manager is also triggered when the user enters the actual start and end date for the task called "First Subject, First Visit" in the protocol plan. When this happens, the protocol status will be set to "Screening Ongoing."

If the Event Manager is deactivated the user will enter the actual date for the task "First Subject Screened" in the site plan and must manually change the site status to "Screening Ongoing." The user will also have to enter the actual date for the task "First Subject, First Visit" in the protocol and subsidiary plans and change the study status to "Screening Ongoing."

When a subject has completed the enrollment visit for a protocol, they are considered enrolled. When the event is an on going enrollment, the first subject enrolled, the flow chart of FIG. 27g explains the operation of the Event Manager. There are two methods that the Event Manager can use to automatically determine when the status of a site and study should be set to "Enrollment Ongoing."

The first method can only occur when subject-visit level tracking is being done. The Event Manager will be triggered when the visit contact is finalized. If the enrollment date for any subject was entered into the finalized contact, the Event Manager will update the site status to "Enrollment Ongoing." The Event Manager will then scan for the minimum enrollment date of all subjects for the finalized contact. This date will then be inserted in the actual start and end date fields for the site plan task called "First Subject Enrolled." The duration will be set to zero, and the fields will be locked.

The Event Manager will then roll this information up to the subsidiary plan level, but only for sites within the Subsidiary, and will compare the minimum date for the task called "First Subject Enrolled" across all site plans. Once identified, this minimum date will be updated in the actual start and end date fields in the subsidiary plan for the task called "First Subject Enrolled." The duration will be set to zero and the fields locked.

Finally, the Event Manager will roll this information up to the protocol plan level for all sites and will compare the minimum date for the task called "First Subject Enrolled" across all site plans. Once identified, this minimum date will be updated in the actual start and end date fields in the protocol plan for the task called "First Subject Enrolled," the duration will be set to zero and the fields locked. The Event Manager will update the study status to "Enrollment Ongoing."

The second method that will trigger the Event Manager is when a number greater than zero is entered in the site-tracking window for the field called "Number of Subjects Enrolled" for any "as of" date in any site contact that has been finalized. Because there is no appropriate date associated with this occurrence, the Event Manager can only alter the site and protocol status, changing them to "Enrollment Ongoing" (again, following the appropriate hierarchy rules).

Figures 1, 27G:
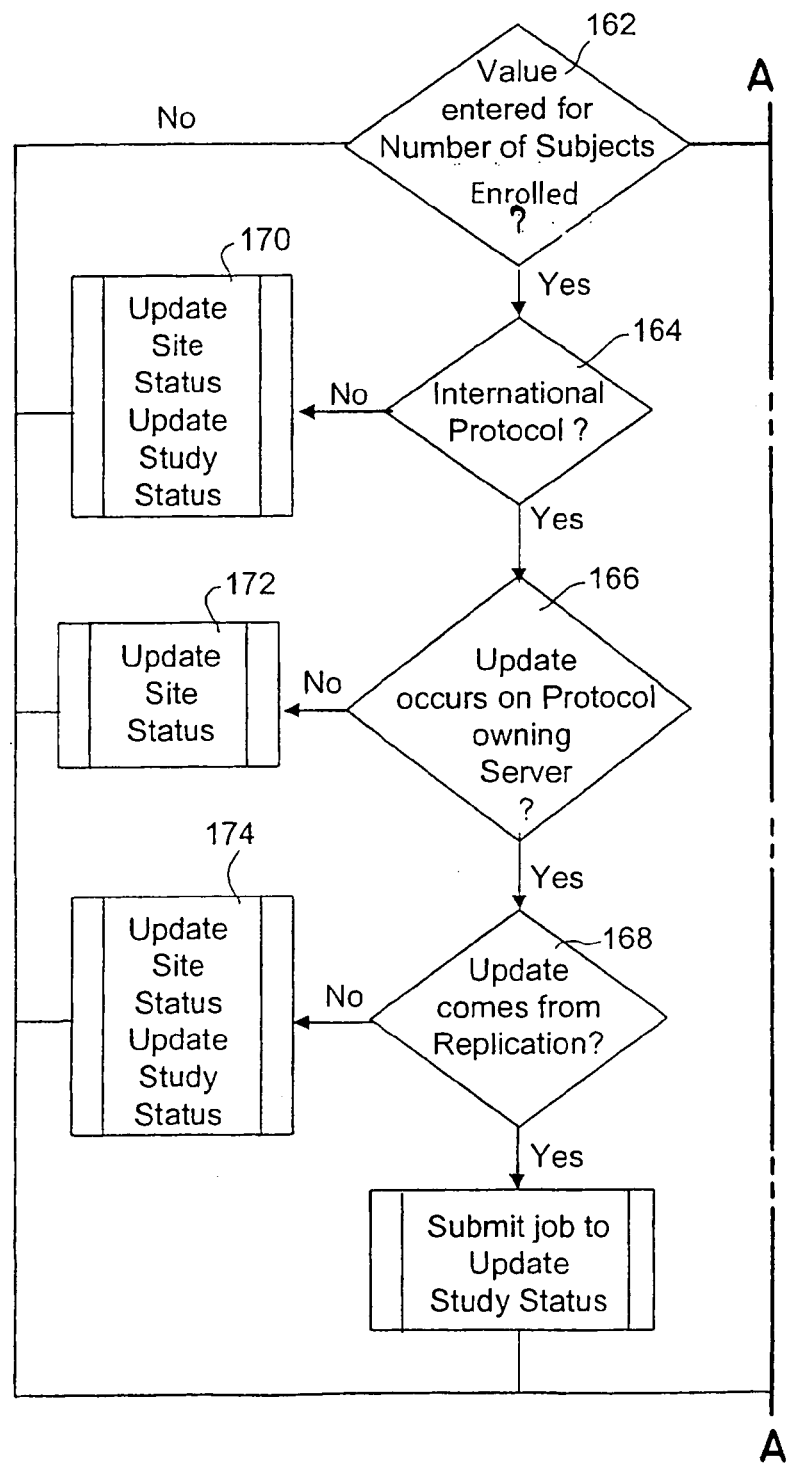
Figures 2, 27G:
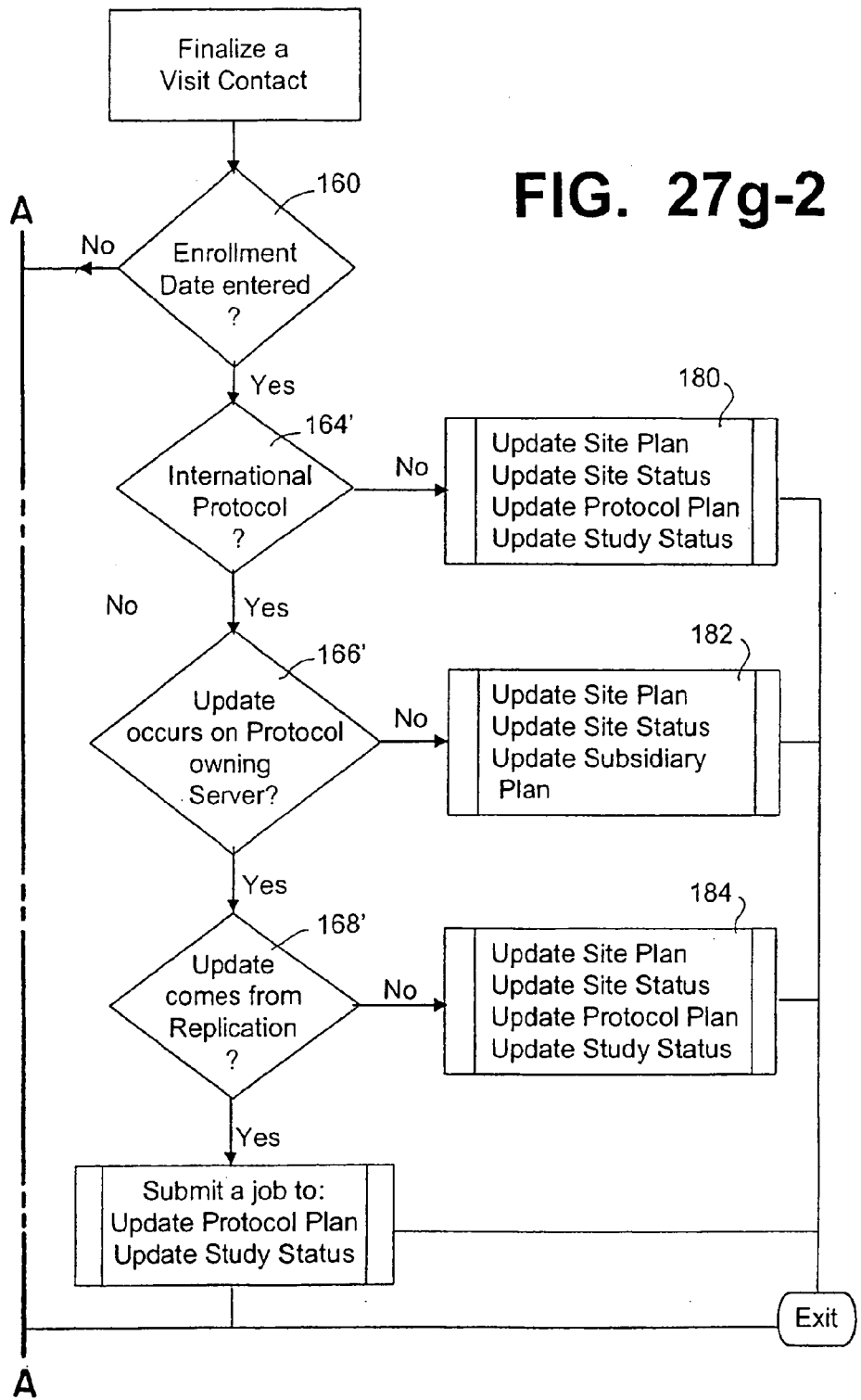

The flow chart for this process in FIG. 27g is essentially the same as the flow chart of FIG. 27f, except that in block 160, a determination is made as to whether the enrollment date is entered as opposed to the screening numbers are created. Also, there is no equivalent determination with respect to the date of first visit entered in step 163, as there is in FIG. 27f, so there is no cross-over line.

In this situation the Event Manager is Milestone triggered when the user enters the actual date for the task called "First Subject Enrolled" in the site plan. When this happens, the site status will be set to "Enrollment Ongoing." The Event Manager will also continue with the updates to the subsidiary plan, protocol plan, and study status as above. The Event Manager is also triggered when the user enters the actual start and end date for the task called "First Subject Enrolled" in the protocol plan. When this happens, the protocol status will be set to "Enrollment Ongoing."

With the Event Manager deactivated the user will enter the actual date for the task "First Subject Enrolled" in the site plan and manually change the site status to "Enrollment Ongoing." The user will enter the actual date for the task "First Subject Enrolled" in the protocol and subsidiary plans and manually change the study status to "Enrollment Ongoing."

Figure 27H:
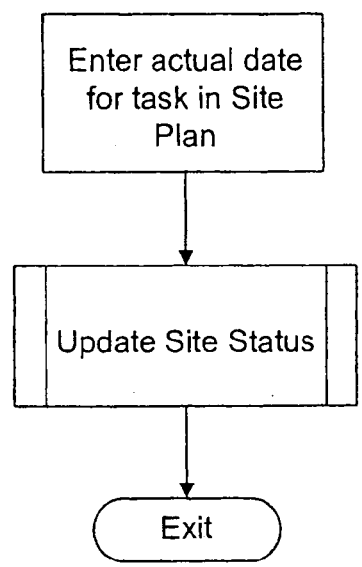

FIG. 27h shows the simple updating of the Site Status in response to the "Enrollment Complete", "Clinically Complete" and "Site Closed" Milestone events.

When the site enrollment or study enrollment is complete, the user will enter the date of this completion in the site, subsidiary, and protocol plans. In this case, the Event Manager is triggered when the user enters the actual date for the task called "Enrollment Complete (Site)" in the site plan When this happens, the site status will be set to "Enrollment Complete." The Event Manager is also triggered when the user enters the actual start and end dates for the task called "Enrollment Cutoff (Protocol)" in the protocol plan. When this happens, the study status will also be set to "Enrollment Complete."

Where the Event Manager is inactive, the user enters the actual date for the task called "Enrollment Complete (Site)" in the site plan and changes the site status to "Enrollment Complete." The user will enter the actual start and end dates for the task called "Enrollment Cutoff (Protocol)" in the protocol and subsidiary plans and change the study status to "Enrollment Complete."

When all subjects at a site have attended all planned study visits, the site is considered "Clinically Complete." The user will enter the date of this completion in the site, subsidiary, and protocol plans. In this case, the Event Manager is triggered when the user enters the actual date for the task called "Last Subject/Last Visit (Site)" in the site plan. When this happens, the site status will be set to "Clinically Complete." The Event Manager is also triggered when the user enters the actual start and end dates for the task called "Last Subject/Last Visit (Protocol)" in the protocol plan. When this happens, the study status will be set to "Clinically Complete."

The user will enter the actual date for the task called "Last Subject/Last Visit (Site)" in the site plan and change the site status to "Clinically Complete" when Event Manager is deactivated. The user will enter the actual start and end dates for the task called "Last Subject/Last Visit (Protocol)" in the protocol and subsidiary plans and change the study status to "Clinically Complete."

After the data cleanup at a site is complete, the study monitor will visit the study site to finalize the study files and ship back any leftover drug supplies. Once these tasks have been accomplished, the site is considered closed. In this case, the Event Manager is triggered when the user enters the actual date for the task called "Site Closed" in the site plan. When this happens, the site status will be set to "Closed." If the Event Manager is inactive the user will enter the actual date for the task "Site Closed" in the site plan and change the site status to "Closed."

Figure 27I:
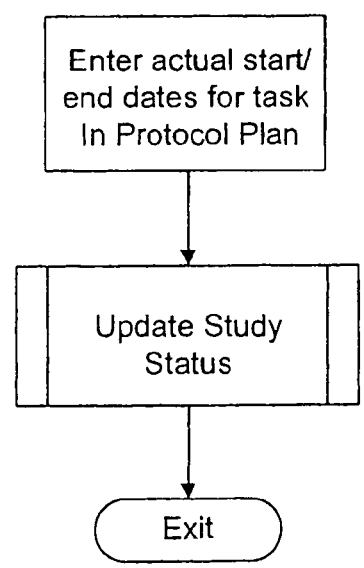

FIG. 27i shows the simple updating of the Study Status in response to the "First Site Initiated & Site Initiated", "First Subject—First Visit", "Enrollment Ongoing" and "Enrollment Complete" events as described above. In addition, it describes updating the Study Status for "All Data In-House", "Data Cleanup Complete", "Database Locked" and "CSR Approved."

When all data at all sites under a protocol has been collected, the protocol status is considered "All Data In-house." In this case, the Event Manager is triggered when the user enters the actual start and end dates for the task called "Last Data In-house/SPRI HQ (Protocol)" in the protocol plan. When this happens, the study status will be set to "All Data In-house." If Event Manager is inactive, the user will enter the actual date for the task called "All Data In-house (Site)" in the site plan. The user will also enter the actual start and end dates for the task "Last Data In-house/SPRI HQ (Protocol)" in the protocol plan and change the study status to "All Data In-house."

When all data exceptions at all sites under the protocol have been collected, the protocol status is considered "Data Cleanup Complete." Here the Event Manager is triggered when the user enters the actual start and end dates for the task called "Data Cleanup Complete (Protocol)" in the protocol plan. When this happens, the study status will be set to "Data Cleanup Complete." With the Event Manager inactive the user will enter the actual date for the task called "Data Cleanup Complete (Site)" in the site plan. Further, the user enters the actual start and end dates for the task "Data Cleanup Complete (Protocol)" in the protocol plan and changes the study status to "Data Cleanup Complete."

When all data for the protocol has been added to the database and all corrections made, the database is locked-down and no more changes can be made. Then, the Event Manager is triggered when the user enters the actual start and end dates for the task called "Database Locked" in the protocol plan. When this happens, the study status will be set to "Database Locked." Should the Event Manger be inactive the user must enter the actual start and end dates for the task "Database Locked" in the protocol plan and change the study status to "Database Locked."

When Medical communications has finalized their write-up of the protocol data and statistical analysis, and a final report is published, the study status is considered "CSR complete." Under these conditions the Event Manager is triggered when the user enters the actual start and end dates for the task called "CSR Approved" in the protocol plan. This causes the study status to be set to "CSR complete." On the other hand, should the Event Manager be inactive, the user will have to enter the actual start and end dates for the task "CSR Approved" in the protocol plan and change the study status to "CSR complete."

7. Site Administration Module

The Site Management module of the system is the portion of the system that pertains to setting up and managing study sites. This module would typically be used by the Site Study Monitor, but they may be assisted in some of these areas by an administrative or clerical support person. The module consists of five sub-modules related to this management. The first is Site Request, which is used to obtain a site number and indicate participation of an investigator in a specific protocol. The second sub-module is Site Administration, used to perform a collection of system and business administration tasks. The third area of the Site Management module is Site Personnel & Locations, used to associate various employees and non-employees and facilities or organizations with the study site. Fourth is Site Budget, used to budget amounts to be paid to the site for participating in the study. The fifth sub-module of the Site Administration module is Site Study Tracking, used to plan and track site related activities.

7a. Site Number Request

A typical process flow within the Site Management module starts with the request for a site number. Once a site number has been issued, based on the required number of sites versus the number of site numbers already issued, the user goes into the Site Personnel & Locations window. After associating the known people and places with the site, the user to Site Administration. In this sub-module the user ties the site to the pre-study visit, indicates the level of budgeting to be done, and updates the number of subjects expected at the site. From here the user goes on to the Site Budget module, and calculates the study costs by assigning prices to procedures and entering in the number of subjects per visit. The next step might be to plan the activities or important milestones for the site in the Site Study Tracking sub-module, such as when enrollment will start and when the last subject is expected to complete their final visit. Known completion dates would also be entered at this time to begin the tracking aspect of the plan. Within the Site Management module, many of these steps are iterative, and it is common for users to continue to associate people or places with the site or update the budgeted costs throughout the entire time of the study. Study Tracking in particular demands ongoing updates to record actual completion of the tasks in the plan.

A site can only be approved if there is an approved Study Management Plan for the protocol. The system also will only allow the user to create up to the number of sites specified for this protocol in the Protocol Study Plan of the Milestones module. The information on the locations and personnel used in this module must first be entered in the Country Administration module. The sites that are available for selection must also initially be entered in the Location sub-module of Country Administration. The employees and non-employees located at the sites must be entered in the rosters. Locations and personnel used in formulating budgets must first be part of the Global Request roster. This information can be manually entered, but preferably it is provided by means of a link to the company's Human Resources and Finance databases.

By clicking on the Modules menu and selecting Request, the Site Number Request screen is displayed as shown in FIG. 28. This window allows the user to see all of the sites previously requested, but only for the protocols to which the user has access. This window also allows the user to request new sites. To enter requests for new site numbers, click on the File and New button and a Site Request Detail screen will appear as shown in FIG. 29. The information is filled in and it is submitted. However, a site can only be approved if there is an approved Study Management Plan for the protocol, and the user can only create up to the number of sites specified for this protocol in the site study plan of the Protocol Module. Returning to the site number screen, searches can be preformed on a list of previous sites using normal windows tools and a records scroll bar provided on the Tools bar. Further, the user can filter records by choosing Filter from the View menu and filling out the dialog box that appears.

7b. Administration

The site administration sub-module is accessed by clicking on Modules and then Site and finally Administration in the menu. This module allows the user to enter and maintain the basic information on a site within a protocol. Its screen (FIG. 30) has two main tabs, Site Administration and Post-Study evaluation. The Site Administration tab, allows the user to enter and maintain administrative information about the site, the enrollment and the budget. Some of this information includes the Site Status, the Data Collection Tool, the Primary Location for a study and a list of Pre-Study Visits that can be associated with this site. Any of this information can be updated as necessary.

FIG. 31 shows the Post-Study Evaluation tab, where the user can enter an overall review of the study for this site, after the study has been completed. The evaluation categories on the screen contain a selection list with choices such as, excellent, very good, etc. The Global Assessment Field allows the user to enter whether or not to recommend the sites for future studies. If a site is not recommended, a comment must be written in the comments icon.

7c. Personnel & Locations

The Personnel and Location sub-module screen is shown in FIG. 32. This window is used to identify and maintain information about the locations, as well as the employees or representatives that will be used for a study at the site.

All the tabs for this sub-module reside on this screen and share a common header. The protocol is selected from the protocol security view, which limits which protocols can be seen by users in any given country. A further filtering takes place based on the drugs to which the current user has access. Once a protocol is selected, all the sites that have been created in the current country, are available to the user. Once the site has been chosen the country, drug and investigator name are displayed in the header and individual tabs are populated with data for the selected sites.

The Locations tab on the screen, is used to identify and maintain the information about the location that will be used for a study site. These may be locations where subject visits will take place, where lab work is done or any of a number of other roles that facilities can play in the course of a study. This tab also allows the user to add new locations by picking them from the Facilities Roster entered into the Country Administration Module. It then allows them to assign a role to the location, identify whether or not the location is still active in a particular role and identify which location is the primary location. If more details about a location are necessary or desired, the user can click on the location and a details box will appear with more information.

The next tab identifies company Personnel as shown in FIG. 33. This tab is used to identify and maintain information about employees who are representatives of the company involved in monitoring or working with a study site involved with processing the study data collected. This tab allows the user to add new personnel by picking them from a Staff Roster entered into the Country Administration Module. It then allows them to assign responsibilities to the personnel, identify whether or not the person is still active in a particular responsibility and identify whether or not the personnel has write access to the study site information maintained in the system. This write access controls who has the ability to enter and edit information in the entire site module, as well as the Site Contact module. When a site is first created in the system, the person requesting the site is automatically added to this list with the responsibilities of site requester and with write access.

The Non-Personnel tab brings up the screen shown in FIG. 34. This tab is used to maintain information about personnel involved in a study site who are not employees or representatives of the company. It operates generally like the employee tab.

The last tab is Non-employee Personnel Locations, this area is used to identify and maintain the relationships between non-employees and the locations where they work or can be reached for a study site. Although a person may be linked to more than one location, one and only one can be designated as the primary location. In other parts of the system, the primary location will be used for things like the location for correspondence to be sent. FIG. 35 illustrates the content of the Non-Employee Location screen.

7d. Site Plan Tracking

From the Modules menu and the Site option, the user can reach the Site Plan Tracking screen (FIG. 36). This window permits the entry of estimated completion dates and actual completion dates on the site level. This window also permits the entry of new Milestones and the creation of task groups using indentation. Site plans are made up of only milestones. When first entering this module or sub-module, a Site Plan is created from the Study Plan and Site Instructions windows, and is copied to the Site Study Plan Instructions. The task list can then be modified. This copy of the Site Instructions is what is accessed on all subsequent executions of this module for this protocol, country and site. If the protocol is being tracked by the Event Manager, once a task has had status reported to it by the Event Manager, manual entry of information for that task is prevented.

7e. Site Budget

The site budget sub-module, allows the user to formulate budgets for the sites within a protocol. The user can plan the cost of procedures, overhead and any additional costs that will be incurred during the study at this site. The budget for sites can be formulated at one of two levels, the user can either budget at the site level or at the procedure level. Procedure level budgets itemize the cost for treatments performed on the subjects during each individual visit. Budgets at the site level can be used to show a higher level line item cost, such as the cost for an entire visit. A procedure level budget can not be accessed unless the protocol has a procedure level Visit Map.

Site budget sub-module screen is reached from the Module—Site Administration menu hierarchy. The Site Budget sub-module is composed of four tabs, Administration, Site Payees, Site Budget and Subject Cost. The Administration tab, as shown in FIG. 37, allows the user to keep track and manage the status of the budget and overhead percentage for this site. From this tab the user will be able to finalize his budget.

The Submit Date field displays the date the budget is submitted. This field will be blank until the Grant module is added to the system. The Effective Date field displays the date that the budget was finalized or that a revision was finalized. The Overhead Percentage field allows the user to enter the overhead percentage that is applied to the line items of the Site Budget tab. The Site Budget sub-module also contains output features. Hard copies of the budget can be printed along with the budgetary information form. Also, available for printing are final payment worksheets used in final confirmation of payments to the sites.

The Site Payees tab allows the user to select the non-employee personnel or locations that will receive the money allocated in this budget. For a particular protocol and site, the user can set the local payee or global payee and finance codes. The site payees that are selected in the screen become the choices on the default payee drop-down list in the site budget tab. The choices in the global payee drop-down list and site payees, comes from the approved Global Payee Roster in the Country Administration module. This roster is maintained by Accounts Payable and Research Finance, preferably through links to their databases. Away from the headquarters location, for example, outside the United States, the local payee roster and the users can select both local and global payees, once a local payee is entered into the system in the Country Administration module. Their name is available for selection as a Site Payee. The Site Payee tab can be edited, a view of this window is shown in FIG. 38.

The next tab is the Site Budget tab shown in FIG. 39, as can be seen, this window allows the user to formulate budgets for the sites within a protocol. The user can plan the cost of procedures, overhead and any additional cost that will be incurred during the study at the site.

The budget for sites can be formulated at the site level or at the procedure level, as noted above. The site budget tab is where the actual budget for this site is formulated. The information entered in the subject cost tab will be the values displayed as procedure costs.

Budgets at the site level can be used to show a higher level line item cost, such as the cost for an entire visit. When budgets are done at the site level, it is not necessary to enter individual procedure cost.

The line on the screen for adjustments allows the user to make budgeting corrections. The Other Cost line gives the user the flexibility to enter additional cost incurred at this site. For each line item in this budget, payee information can be entered and an overhead percentage can be assigned. At the bottom of the screen the system calculates the total budget.

As shown in FIG. 40, the Subject Cost screen, reached from the Subject Cost tab, can be used for budgeting. The formulation of a procedure level budget is begun in the Subject Cost tab. The user must enter the number of subjects to be budgeted during each visit, a treatment schedule is selected, and then the cost for each procedure is assigned. This feature allows the user to accurately budget the anticipated subjects for screening and the normal anticipated enrollment of subjects.

In the Site Budget Subject Cost tab, each procedure gets a unit cost value which is multiplied by the number of subjects for that procedure for that. If a procedure was not entered in the treatment schedule, but needs to be itemized as a cost, it can be entered as an additional visit cost in the subject cost path. If there is a second treatment scheduled for this site, it must also be part of the budget.

A function is available on this tab entitled "Copy Value to Right." This function will copy the value in the current field to all editable fields to the right of the current field. It will be available on the Subjects Budgeted Procedure Cost and Additional Visit Cost fields when the current revision is in "Draft" mode.

Once a treatment schedule has been budgeted, the down arrow next to "treatment schedule" can be clicked and a second schedule selected for budgeting.

Once the budget is complete, the user returns to the Administration screen, where the budget is finalized. The finalization is reached through the actions menu at the header of the screen.

8. The Site Contacts Module

The Site Contacts Module of the system is the portion of the system that supports the initiation, recording, and tracking of site contacts. A Site Contact is an interaction between a study monitor and the personnel at a site or a prospective site. One of the major goals of the system is to automate the collection of site contact data.

The area of the system that supports the recording and tracking of visit contacts made before a site is chosen is called the Pre-Study Visit module. It facilitates the evaluation of a potential location as a study site. In particular, before a site can be used in a research study, pre-study visit(s) must be conducted. They provide the opportunity to evaluate and assess the potential investigator and the potential study location.

The second sub-module is the Site Contacts module, which is used to monitor the site's activities, and confirm that a protocol is being conducted properly. Site Contacts can be either by actual visits to a site, or by phone, e-mail, or fax. There are two broad areas of information that need to be recorded and maintained related to the Site Contacts, and these are captured in the following two features within the system:

(1) Site Tracking (available for both visit contacts and non-visit contacts) allows the monitors to record key summary information about the progress of the study at the site. It enables the monitors to keep statistics on how many subjects are ineligible for the study, how many are enrolled in it, and of these, how many are discontinued and completed.

(2) Subject Visit Tracking (available for visit contacts only) allows monitors to track general and specific information about the individual subjects at a study site. It enables them to review the subject records for safety and compliance with the protocol, and to assure the accuracy of the data being recorded in the Case Report Forms (CRF) or via Remote Data Entry (RDE). This information is later used to generate federally mandated trip reports.

8a. Pre-Study Visits

A typical process flow within these functions starts with the identification of a potential site and a potential investigator for a study. Before a site can be recommended, pre-study visits are made. These visits are tracked via Pre-Study Visit Numbers. Monitors meet with potential investigators and other non-company personnel at a potential site. After gathering information about the overall quality of the site, as well as its ethical aspects, a global assessment is made to either recommend the site, or not, for the study.

The Pre-Study Visit Numbers are used to track the last time an investigator was visited. If this was within one year of the study, a new Pre-Visit is not necessary.

Once the site is selected for the study, monitors will make contacts, either in person (i.e., visit contact), or by phone, e-mail, or fax (i.e., non-visit contacts) with personnel at the site. As these contacts are made, it is very important to record the location, date, the reason for the contact, and the names of those who attended the meetings or were involved in the non-visit contacts. Documentation is provided in the system on a wide variety of topics that might be reviewed during these contacts, as well as the monitor's activities. This enables the monitors to continue to evaluate the acceptability of the site for the study, after the initial recommendation to include the site has been made.

As the study proceeds, the study monitors need to keep track of the individual subjects taking part in the study. After entering statistics about the overall numbers of subjects who were ineligible (and why) for the study, those who were enrolled, screened, discontinued (and the reasons for discontinuation), completed, and those ongoing, the Site Tracking feature performs various calculations so that the monitor has an overall picture of the subjects at the site.

In addition to overall statistics about the subjects, the monitor needs to record and maintain specific information about each subject and the individual visits that they make in conjunction with the study. The monitors use the Subject Visit Tracking feature for this purpose. The design of the protocol mandates a specific series of visits, the procedures to be conducted during each visit, and the kind of data that is to be gathered. The monitor will keep track of information mandated in the protocol design, i.e., whether the subjects' visits were within the prescribed time frames, what phase they are in, and how much data has been verified and collected. Subject Visit Tracking also facilitates keeping track of visits for which there is additional follow up work yet to be done. Finally, the monitor utilizes Subject Visit Tracking to keep a running summary report of all of a subject's visits.

The Pre-Study Visit screen is reached through the Modules selection in the menu. It is the first tab of a screen with five tabs as shown in FIG. 41. It has locations for entering the company representatives in the pre-study visit, as well as the investigators located at the site. The date and time when they visit are identified. Also the potential study location is recorded. If a pre-study is being conducted on a location not yet in the system, it can be added in the system using the Country Administration option. Similarly new investigators can be added. Company personnel can populate the pre-visit screen by means of a drop-down arrow, which list them. This tab allows access to information about these people for e.g., gender, contact information and their associated expense center. The Non-company Personnel tab is used to identify and maintain information about non-employees who participate in a pre-study visit. It allows the user to select them. Input screen is basically the same as for employees (See FIG. 42).

FIG. 43, shows the screen that appears when the Discussions tab is selected. It allows the user to capture pre-study visit discussion items which are preselected by merely clicking on a box. The final tab shown in FIG. 44, is for Evaluations. It captures the overall assessment of the pre-study visit and it requires the user to select a global assessment of either recommended or not recommended. Further, the user can enter supporting comments pertaining to the global assessment. In addition, the user can select an evaluation for each of the criteria to be evaluated. These criteria are dynamically displayed from the previous evaluation table. New criteria for evaluation can be added by the World Wide System Administrator.

8b. Visit and Non-Visit Site Contacts

One of the major goals of the system is to automate the collection of site contact data. A site contact is an interaction between a study monitor and personnel at the site. Site contacts can either be site visits or non-visit contact, such as telephone calls, e-mails and faxes. These screens can be reached through the Modules—Site-Contact menu. The Visit Contact window is used to allow the user to view visit contact information regarding a site, to create a new visit contact information or modify an existing one, and to finalize and lock a visit contact. The screen is shown in FIG. 45. It provides a Visit Contact tab and a Discussion Items tab. The Visit Contact tab, allows the user to identify and maintain information regarding a visit contact. It records general information such as, contact date, time, participants, the reason for the visit contact and a recommendation regarding the investigator and the site. This screen also allows the user access to additional information related to the visit contact such as, site tracking information. This is information regarding the subjects enrolled at the site and those ineligible for screening, as well as tracking information, including but not limited to date of birth, age and enrollment, date of signing consent, etc. The Visit Contact tab allows the user to finalize the visit contact. Once finalized, the user can view the visit contact data, but can not add or change any data associated with it.

Figure 46:
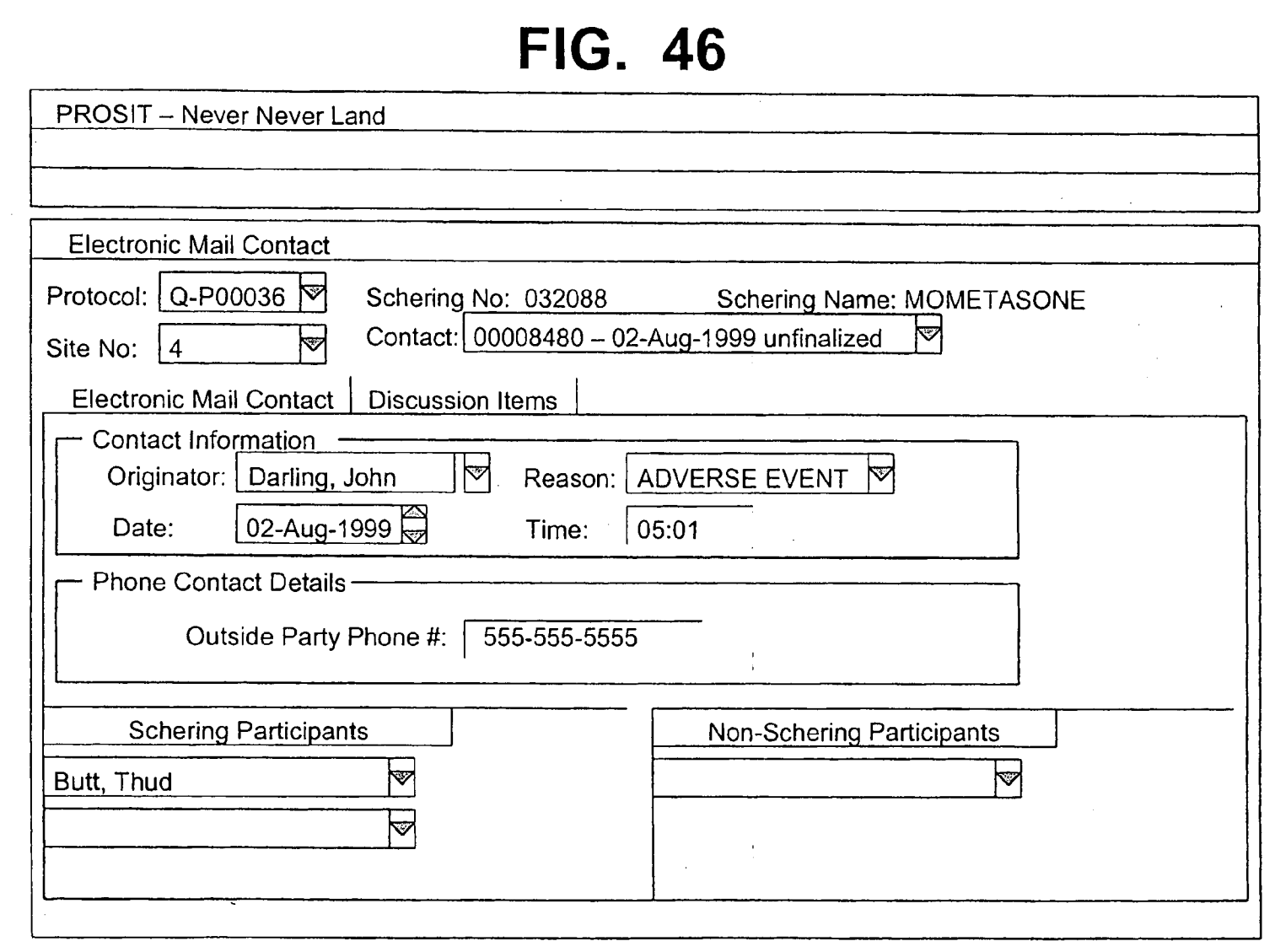

Using the same menu hierarchy, a non-visit contact, such as an electronic mail contact, can be recorded as shown in FIG. 46. The Electronic Mail Contact tab allows the user to record general information about the contact, such as the originator, the reason for the contact, the date and time, the outside party's phone number, and the participants.

In both visit and non-visit contacts, Discussion items tabs are provided. Such Discussion Items tabs are shown in FIG. 47. This tab displays a screen with standardized discussion items, which allow for easy recording and documentation of typical contacts.

8c. Site Plan/Subject Tracking

The site tracking allows the user to record key summary information about the progress of the study at the site. It also allows the user to keep statistics on how may subjects are enrolled, ineligible, complete or discontinued. Site tracking is accessed through "Actions" on the main menu. It is also available through the Visit Site Contact Tab and the Non-Visit contact tabs. The Actions menu also provides access to the Finalize Site Contact and Subject Tracking features.

The Enrollment Tracking tab in the Site Tracking window, (FIG. 48a) allows the user to enter and maintained some summary statistical information. This data pertains to subjects in the site who are being studied for the protocol. It allows the user to keep track of how many subjects are ineligible for screening, how many have been screened, enrolled, discontinued, completed and ongoing. The tab performs various calculations on the statistics for the user. The enrollment data screen, defaults to the values in the most recent site contact.

The next tab on this screen is the Ineligible For Screening tab (FIG. 48b), which keeps track by reason of the number of subjects who were found ineligible for this study. Subjects can be found ineligible for a study based on more than one factor. The number of subjects at this site found ineligible for screening is displayed on this screen and is also displayed on the Enrollment tracking screen. Once the site contact is finalized, the ineligible for screening tab information can not be modified.

In addition to site tracking, subjects can be tracked by means of a Subject Visit Tracking window shown in FIG. 49, this tab allows the user to create and maintain details about subjects at the site. If no Visit Map exists, the user can record and maintain basic information about the subject, for e.g., date of birth, age at enrollment, the date of a signed consent, the beginning and ending date of therapy, the date and reason of discontinuance from the study, etc. If the Visit Map exists, information populates this windows from other windows, e.g. subject visits can be tracked with the corresponding visit categories and study phase according to the Visit Map, which then fills in the last visit number and current phase field of this window. Subject tracking is available only if the contact is a visit and it has not yet been finalized. Subject visit tracking can only be accessed if a protocol design is finalized.

This window also has Visit Summary, Discontinued Visit, and Un-Schedule tabs where comments can be made. The Visit Summary tab screen which is shown in FIG. 50, provides a summary of all visits the subject has made. It includes the visit number and a description of the visit according to the visit map. It further provides an indication of whether any data is yet to be collected. It also provides source document verification and generates required visit contact reports or forms with subject tracking information.

9. Clinical Supplies Module

The Clinical Supplies Module is the portion of the system that supports the initiation, recording, and generation of clinical supply forms (both in draft and final form). These forms and their corresponding information in the system are used to facilitate the manufacturing, packaging, randomizing and shipping of drugs and materials to the sites and subsidiaries involved in clinical studies. This module would typically be used by site monitors.

This module consists of four (4) sub-modules. Within each of these modules, the system enables the generation of the form required to communicate information to carry out the process.

The first sub-module is the Formulated Materials Requisition (FMR) module, which is used to request the manufacture of a specific drug supply that is going to be used in a study. The second module is the Packaging/Shipping Request (PSR) module, which is used to communicate to Clinical Manufacturing Services the appropriate method for packaging and the destination for shipping clinical supplies that are manufactured under a Formulated Materials Request. There are two ways that clinical supplies can be handled under a study, and each one generates a PSR form:

1. Protocol Packaging—Creating one Packaging and Shipping Request for the entire protocol. A Material Transfer Request or MTR (see below) is then used to disburse supplies to the individual sites.

2. Site Packaging—Creating a Packaging and Shipping Request for every site in the study. The PSR indicates the investigator and the location to which the supplies are to be shipped.

The third module is the Material Transfer Request (MTR) module, which is used to communicate with the Clinical Manufacturing Services Warehouse Manager in order to have material from inventory shipped to other locations. The fourth module is the Random Code Request (RCR) module. If a study requires randomization and/or stratification, random codes will need to be prepared by the Biostatistics group. The Random Code memo is issued by Clinical Research to a Biostatistics group for the creation of a randomization code for a protocol. The RCR is usually required to be completed before a PSR can be submitted for packaging. (RCR memo generated)

A typical process flow within these functions starts by gathering information needed if a drug is to be manufactured for the study. The Formulated Materials Requisition ("FMR") is used for this purpose. Data gathered includes the company reference number for the drug to be manufactured, its dose form, strength, number of units required, any requests for a placebo/comparator, the date required for packaging, special directions and blinding information, along with the names of the requesting party and the person who authorizes the FMR. The FMR can also be used if the drug being requested is a commercially marketed product.

The next step in the process is the creation of a Random Code Request (RCR) memo. This memo communicates to the Biostatistics group the need for random codes to be prepared. It outlines for the Biostatistics group how subjects are to be randomized, the number of subjects, how subject numbers will be assigned, the number of sites, and whether there are any stratifications. A copy of the protocol is attached to the RCR when it is distributed.

Following the creation of the RCR memo, the Packaging and Shipping Request (PSR) can be prepared. The PSR communicates the appropriate method for packaging and if the clinical supplies are packaged by site, the PSR also includes the destination for the clinical supplies. It outlines all the components and the quantities required to be taken from inventory and packaged. It also specifies the "Ship To" location for site packaging and international protocol packaging. The "Ship To" information for local protocol packaging is found in the MTR.

Finally, for local Protocol Packaging, a Material Transfer Request (MTR) is used to disburse supplies to the individual sites. It specifies the material type, appropriate batch numbers, PSR numbers, FMR numbers, the quantity on hand, the quantity needed, and the "Ship To" location information.

9a. Formulated Material Requisition (FMR)

The Clinical Supplies screen is reached through the Modules menu. The Formulated Materials screen is one of the selections in this menu. The FMR window and its associated tabs (FIG. 51) are used to request the drugs to be used in a clinical program or an individual study. The drug requested might need to be manufactured or it may be purchased. An FMR form is produced by the system and is then submitted to Clinical Manufacturing for processing.

The Administration tab of the FMR window identifies key information about the program or study for which that the material is being used. The protocol information (protocol no.) is not required for submission of the FMR. However, if the FMR is for a particular protocol, the protocol number should be included. If the drug is for a variety of studies, then the protocol number is not necessary. If known, a list of the protocol numbers requiring the drug should be included in the special instruction section.

The FMR Administration tab identifies the Program Code, Company Number, and Marketed Dose form of the primary drug that is being studied. The expense center of the area sponsoring and financing the trial is included in this tab, as well as the person requesting the FMR and the person who can approve the request.

Each FMR needs to identify the group responsible for initiating the FMR request, the date required for packaging, whether or not the drug needs to be blinded and any special instructions. This is all completed in the Administration tab of the FMR window. When the FMR is saved, an FMR Req. ID number is automatically generated. When the FMR is completed, it must be finalized before being printed and submitted to Clinical Manufacturing. This finalization process is also done in this tab.

The Materials tab of the FMR identifies specific information about the drug that is being requested for a clinical program or individual study. All drugs that are requested and used have a Company No. associated with them, regardless of whether they are produced by the company. The drug that is being requested will have certain characteristics that need to be identified in the FMR. This includes the strength/concentration, the form in which the drug will be manufactured, and the drug's package description and fill. The Materials section of the FMR also includes the number of units to be manufactured, if the material to be supplied is left packaged as it is by the original manufacturer, and if it is a substance controlled by the Drug Enforcement Agency.

If the drug is to be used as a comparator or placebo, the primary drug must be identified in a separate section of the Materials tab (the lower section). The characteristics of the primary drug are identified in this section.

9b. Packaging/Shipping Request (PSR)

The PSR screen (FIG. 52) creates the PSR form which is used to communicate information to Clinical Manufacturing regarding clinical supplies that were manufactured under a FMR. This information includes the appropriate method for packaging the supplies, as well as the destination to which they are to be shipped. The PSR information tab allows the user to record accounting and expense center data, whether the Protocol/Site is new, the study type, the names of the study monitors, the person requesting and the person authorizing the PSR, shipping and labeling dates, special instructions and any attachments that are to be sent with the PSR.

In the Protocol Packaging PSR information tab, the selected site and Random Code Generation ID are recorded in addition to the above data. The latter two data fields do not appear in the PSR Information tab for Site Packaging.

9c. Materials Transfer Request (MTR)

The Components tab (FIG. 53) of the PSR Screen allows the user to inform the packaging area as to the drug, its dose form, strength/concentration, package description, and the number of units required, that are to be taken from inventory to package the drug correctly for the given PSR. The "Ship To" tab (FIG. 54) is used in Protocol Packaging only for international protocols. The Ship To tab is always used in Site Packaging.

The Materials Transfer Request ("MTR") is a form used to communicate with the Clinical Manufacturing Services Warehouse Manager on the disbursement of drugs and supplies to be used in the study. It facilitates the shipping of material from inventory to other locations. The data on the request includes the appropriate packaging and shipping information for the disbursement of supplies stored in the warehouse.

Among the data included in the MTR Details tab (FIG. 55) is the inventory location, the names of the persons requesting and authorizing the MTR, the requested shipping date, the expense center of the protocol associated with the request, notes on the intended use of the material, and information on the type and quantity of material being requested. Also, the user can generate a Material Transfer Request Form from this tab.

The "Ship To" tab (FIG. 56) allows the user to record and maintain information on the "Ship To" location address, and its phone and fax numbers. It also allows the user to enter shipping/packaging instructions.

9d. Random Code Request (RCR)

All studies requiring randomization and/or stratification require that a Biostatistics group prepare random codes. The Random Code Request memo is issued by the Clinical Research group to the Biostatistics group for the creation of a randomization code for a protocol. A copy of the protocol needs to be attached with the RCR memo. The RCR is usually required to be completed before a PSR can be submitted for packaging.

The Random Code Request window (FIG. 57) allows the user to request a randomization code for a protocol. It resembles a memo, e.g., "To" and "From." Subjects are randomized by protocol, site or country. This window allows the user to select how the subjects will be randomized, and to select the type of random code that is being requested for the selected protocol. It also allows them to identify the Random Code Generation ID, which identifies which sites are to be packaged under the specific random code. This window further allows the user to select how patients will be replaced (from protocol), and several other pieces of information for the RCR memo.

10. The Remote Collection or Laptop Module

The Remote or Laptop Module of the system is the portion of the system that supports the remote collection of protocol data. This module is used by the site monitors before and after they make site visits. This feature permits them to Check-Out data to the laptop and lock the server data for a Protocol/Site (to prevent data synchronization errors). Once the date has been checked out, the user can enter data from their site visit using the system on the laptop with the local copy of the Protocol/Site data. Upon returning from the visit, they can then Check-In the updated Protocol/Site data from the laptop, which in turn will unlock the server data.

This module consists of 3 sub-modules. The first sub-module is Check Out/In, which is used to queue a request to the server to 1) lock and compress data on the main database for one or more protocols and sites, 2) transfer the compressed data to the laptop and 3) decompress the data on the laptop. Alternatively, it can be used to queue a request to the server to 1) compress the laptop data, 2) transfer the compressed laptop data to the server, 3) decompress and update the server database and 4) unlock the server data. This module can also be used to remove laptop Data.

The second sub-module is Check Cntl, which is used to determine what Protocols and Sites have been checked out. If need be, the Local Administrators or the user making the request can use this window to remove the lock on a Protocol/Site that has been checked out (either because of an error, because the laptop data is corrupted or invalid, or for some other reason). There can only be one checked-out database to a laptop.

The third sub-module is a set of background Check Out/In Server Processes that prepare the laptop data for transfer, execute the transfer and protect the integrity of data on the server.

A typical process flow within the Laptop module starts with the request for the Check Out of data for a Protocol/Site to a laptop by the Site Monitor, prior to the Site Visit. The request is entered, selecting all the protocols and sites that the monitor will need until he is ready to return the data to the server. When the request is saved, it becomes part of a queue of background work to be performed by the server. The priority of the request, relative to other requests, can be increased, if necessary. Periodically, the server checks the queue to determine if there is any request to be executed. Once a request has been completed, it is marked completed in the control table and removed from the queue, causing the next lower item in the queue to now be the next to be serviced.

The background process takes the data identified in the request and locks it from further update on the server. The data is now copied and compressed with sufficient additional space to support the "off-line" laptop data entry function. Once the data file is compressed and transferred to the laptop, the Site Monitor will disconnect from the server and use the Site Contact sub-module of the system to collect the information from the Site Visit. When the Site Monitor has completed entering the updates for the Site Visit, he will reconnect to the server (at the office or a via dial-up connection) and request that data be returned to the server. The background process transfers the data from the laptop, cleans up the laptop, updates the server's database with the updated information and unlocks that server data. The intent of this feature is to allow personnel responsible for monitoring the research activities at the various sites involved in a study to physically visit a site and enter information into the system via the laptop. This feature eliminates concerns over dial-up connectivity issues, security over public networks, support for another data collection method, etc.

Preferably, instead of using the main server 10, the system uses a Check Out/In server 12 shown in FIG. 1. While not all functionality is available when using checked out data, the features deemed necessary to support pre-study visits and site monitoring activities are present. Upon returning to the office, users are able to process information entered while off-site and have it reflected in the system's database. This process, referred to as checking data in and out, is supported by a pair of processes running on the Check Out/In server 12. There are no system windows for these processes.

This feature is available to both domestic and international users of the system. The first process—The system's Check Out/In Server process—is responsible for creating a database file which will be transferred to the user's laptop. It is also responsible for applying the updates to the system's database 10, when data is checked back in. Another process—the Check In/Out File Transfer process—is used to transmit/receive the necessary files between the server and the laptop. Both can be set to start up when the server is (re-)started for unattended operation. To duplicate the functionality deemed necessary to support pre-study visits and site monitoring, the system may utilize a Sybase SQL Anywhere 5.0 database; a small-footprint, single-user relational database and management system. To minimize the modifications required to the application to support two different Relational Database Management Systems (RDMS's), the SQL Anywhere database schema (tables, constraints, indexes, etc.) are the same as those found in the main database.

There are several basic functions performed by the processes. A parameter in the Check Out/In Server process' configuration file indicates when the process should create a partial SQL Anywhere database. This is the Generic Build, which is normally initiated early in the morning-after replication between the main and subsidiary databases has occurred-so as to minimize the impact on other processing. This partially loaded database will serve as the basis for any Check Out requests processed that day. During this phase, the database system tables are queried to extract information related to all of the system's database tables and views; attributes such as columns, data types, indexes, primary and foreign keys, etc. This information is saved to a series of ASCII text files and reformatted into valid SQL Anywhere DDL (Data Definition Language) syntax. It is then applied to the SQL Anywhere database to create a nearly identical copy of the database schema.

To provide for a higher degree of compatibility between database and SQL Anywhere, five user-defined functions are also loaded into the SQL Anywhere database. These user functions mimic commonly used built-in Oracle functions and eliminate the need to modify the system application depending upon which DBMS is being used. Certain of the system tables are static in nature; updates to the system's Country table are uncommon, for example. To save time when processing users' check out requests, these static tables can be loaded during the Generic Build phase. Any tables frequently updated throughout the day are best loaded when a Check Out request is processed to ensure users have access to the most current data. The decision to extract data from the main database and load the corresponding SQL Anywhere table during the Generic Build is based upon an indicator found in the "Check Out/In Tables" table and can be changed as necessary.

Data is then extracted from the main database for any table indicated to be loaded during the Generic Build phase. These tend to be reference tables (for reasons mentioned above) and all rows are retrieved; there is no criteria limiting selection. The extracted data is written to a series of ASCII text files; the names of which are specified in the "Check Out/In Table." Once data has been extracted from all tables designated to be loaded during the Generic Build phase, the ASCII data files are processed by the Data Compressor. This is done to speed the database load.

The files are then loaded into the SQL Anywhere database based upon an order specified in the "Check Out/In Tables" database table. The order of the load is important because of the referential integrity now present in the database. This is the final step of the Generic Load; the SQL Anywhere database is stored for use as Check Out requests are processed.

When a user requests a Check Out, rows are inserted into two of the main database tables: the "Check Out/In Queue" and "Site Contact Lock" tables. The Check Out/In Server 12 process spends most of the day polling the "Check Out/In Queue" table. When it detects a new Check Out request, it queries the "Site Contact Lock" table to determine the state of the protocol(s) and site(s) associated with the request. As its name suggests, the "Site Contact Lock" table also restricts updates to Visit Contact information by other users associated with the Protocol and Site in question.

As the Check Out request is processed, the request entry is deleted from the "Check Out/In Queue" table and an entry is inserted in the "Check Out/In Control" table. This table contains information such as the User ID of the individual requesting the Check Out, the date and time of the request, the status of the request and a unique filename to identify this request's Checked Out database. The unique filename is obtained from a sequence generator stored in the main database. The status of the request is periodically updated as it is processed. The system users can monitor the status of their requests from the Check Out/In and Check Control modules.

The Check Out/In Process next queries the "Check Out/In Tables" of the main database table to determine from which tables data is now to be extracted (these are tables which were not loaded during the Generic Build phase). In some instances, it may only be necessary to extract data related to the protocol(s) and site(s) requested. That is determined by entries in the "Check Out/In Criteria" table. The purpose of this table is to supply selection criteria to be used when extracting data from the database tables. Common selection criteria limits retrieval of data based upon the requested protocol(s) and/or Site(s) but can consist of any valid SQL WHERE clause syntax.

By reading the "Check Out/In Tables" and "Check Out/In Criteria" tables, the Check Out process builds an ASCII text file containing SQL SELECT statements it will submit against the main database (similar to what is done during the Generic Build phase) via, e.g., Oracles DOS batch query facility (SQLPLUS). As the database processes the SQL SELECT statements, it will write any output to a series of ASCII text files; the names of which are specified in the "Check Out/In Tables" table. Because of the complexity of the SQL SELECT statements (often consisting of JOINS and Sub SELECTS), this step is usually the most time-consuming (especially if multiple protocols and/or sites are requested) of the entire Check Out process.

After the data is extracted, the Check Out server process invokes the Data Compressor and processes all of the ASCII data files to strip any leading or trailing spaces from the alphanumeric data fields. The SQL Anywhere database created during the Generic Build process is then copied and renamed (the name of which is stored in the Check Out/In Control table).

Similar to the Generic Load process, all of the data files are loaded into the copy of the Generic SQL Anywhere database. The database load is driven by an ASCII text file created based upon the information found in the "Check Out/In Tables" (including what data file will be used to load what database table and the order in which the tables are to be loaded).

Upon successful completion of the load, the Private SQL Anywhere database is compressed, e.g. using PKZip, (typical size is about 10 MB prior to compression, although it is usually compressed to half that, depending upon the number of protocols and/or sites). The Status of the request is updated to indicate the Private SQL Anywhere database is ready to be transmitted to the requestor's laptop. The Check Out/In Server process then continues to monitor the "Check Out/In Queue" table for more requests.

After the Checked Out database has been transferred to the requestor's laptop, the user is no longer required to be connected to the network and the main database. They are now able to personally visit the site(s) involved in a clinical study and continue to use the system to capture pertinent information.

When the user has completed his visit and returns to the office, it's now necessary to transfer the information captured while away from the office to the system's main database. This is commonly referred to as checking data in and is initiated by the user from the system's Check Out/In module.

While using the system in Laptop mode, a built-in feature of SQL Anywhere has been employed to capture any modifications made to the Checked Out database. By applying the transactions stored in the log file, it is possible to have all modifications made, while the user was running the system in Laptop mode be reflected in the system's main database. This way, the information gathered can be shared among the relevant parties.

When a user is ready to check data back in, they log onto the system in-house (i.e., connected to main database) and use the system's Check-In facility to submit the Check In request. The client application obtains a unique number from the Check Out/In Oracle sequence generator. This unique number will represent the name of the file being checked in. The transaction log file is copied and renamed and a backup copy of the transaction file is created in the event the file is lost or corrupted in transit.

The system's client application then connects to the Check Out/In Server File Transfer process. This process establishes a TCP/IP connection between the client's workstation and the server. The transaction file is then compressed, e.g. using PKZIP, and transferred to the server via FTP. The client application then updates the appropriate row in the "Check Out/In Control" table with the Check In file name and a row is inserted into the "Check Out/In Queue" table request a Check In.

When the Check Out/In Server process detects the new row in the Check Out/In Queue table, it begins to process the Check In request. It locates the corresponding row in the Check Out/In Control table to obtain the name of the file being checked in and updates the status to indicate that the request is being processed. It then deletes the row from the "Check Out/In Queue" table.

Once it locates the Check In file, it is decompressed using, e.g. PKUnzip. The Check Out/In Server process next invokes an SQL Anywhere utility to convert the transaction log file into a readable ASCII text file containing all of the SQL statements applied to the SQL Anywhere database while the data was checked out.

Because there are some minor differences between SQL Anywhere SQL syntax and, e.g., Oracle SQL syntax, a translation step may be required. During this step, the SQL Anywhere transaction file is parsed. As the SQL statements are read, they are translated into valid Oracle SQL syntax and written to an ASCII text file. This ASCII text file will be applied to the main database so that the information entered into SQL Anywhere will now be reflected in the main database.

Upon successful application of the SQL statements, the status is updated in the "Check Out/In Control" table to indicate that the information has been successfully checked in and the corresponding row(s) is/are deleted from the "Site Contact Lock" table. Other users are now able to view, edit and/or check out information related to these protocol(s) and/or site(s).

The Check Out/In File Transfer Process is a distributed application allowing for file transfers between the Check Out/IIn Server 12 and the client laptop 11. Unlike the Check Out/In Server process, which never directly communicates with the system client application (all "communication" is accomplished via table entries), an actual TCP/IP communication channel is established when the system client application connects to the File Transfer Process.

After a Check Out request has been processed, the system client application will obtain the name of the compressed private SQL Anywhere database from the Check Out/In Control table. It will then establish a connection with the File Transfer Process and copy that file to the system directory on the local machine, decompressing it using PKUNZIP. When requesting a Check In, the system client application will attach to the File Transfer Process and copy the compressed SQL Anywhere transaction log file to the Check Out/In Server.

The length of time it takes to transfer a file depends primarily upon the size of the file and the method of network connectivity. Compressed SQL Anywhere databases tend to be approximately 5 MB and usually takes less than a minute when connected to the Server In-House. The transaction log file is usually quite small; perhaps 500 KB after compression (though the size depends upon the amount of modifications made to the SQL Anywhere database while checked out). Transferring files during the Check In process is considerably quicker than it is when transferring the Check Out database to the client's laptop.

While it is possible to transfer an SQL Anywhere database over a dial-up connection, it is not recommended. In addition to the length of time necessary to transfer the file, there is an increased risk of file corruption due to line noise or disconnection. Because the file involved is substantially smaller, users are more likely to experience a successful Check In than Check Out over a standard dial-up line.

Like most Windows NT services, the system's Check Out/In Server processes are designed to run without intervention. A status window is provided, however, which can be used to monitor Check Out/In activities. As requests are processed, the Check Out/In Server process will periodically update the Status window indicating the progress of a particular request. Additionally, the process can be shut down or a Generic Build can be initiated from this window. The ability to initiate a Generic Build may prove useful if some of the system's "static" tables were updated mid-day. A new Generic Build would allow any users requesting Check Outs to have the most current data present in their Checked Out databases. The lower-left portion of the Status window (FIG. 58) allows for viewing all of the parameters specified in the Check Out/In Server configuration file. The Check Out/In File Transfer process also has a Status window, but since it's a much simpler process, the Status window is considerably simpler as well:

The most important items displayed are the "Rc:" and "Err:" entries at the bottom of the window. "Rc" stands for Return Code; a Return Code of 0 indicates no errors. If the Return Code is not "0," the text of a system error message would appear following the "Err:" entry. This would be a Windows NT Server error message.

Because the system's Check Out/In Server processes are designed to run unattended, additional error-handling features are included. These features include attempting to reconnect to the main database numerous times if the connection is lost due to network or database problems, and shutting down and restarting itself if experiencing repeated connectivity errors. Additionally, the process is capable of sending an e-mail message to Production Support personnel when it encounters problems.

The process also retains files for a user-specified length of time (one month for example). This is useful in troubleshooting issues or confirming that all information transferred from the laptop was actually applied to the main database. After the specified length of time has elapsed, older files related to Check Out and In requests are purged.

Numerous parameters can be specified in the Check Out/In Server configuration files to allow for customization. They include specifying the directories containing required applications, files, etc.; the number of times the process should attempt to reconnect/restart after an error; an e-mail distribution list for personnel to be notified in the event of an error; a delay in the start of the application to allow for the start of the database; the time the Generic Build should be initiated; a period in which the process goes idle (in support of backups or database maintenance), etc.

11. Reporting Features

The Reporting features in the system allow the users to generate printouts of the data entered into the system. Creating a report is a two step process. Within the Reports Modules, reached through the Modules—Reports menu, the user first generates a search for the information desired. The system then generates a formatted Report based on the information retrieved. Reports that can be created include the following: subject information, site information, protocol summary, drug summary, and contact information. Users however, can only create reports based on the access that they have to the information within the system.

The Report Module is composed of two sub-modules: Site/Subject Status and Protocol Status. Site/Subject Status allows the user to create general and/or detailed reports regarding the subjects and the sites. The Protocol Status sub-module gives the user the ability to create summary reports about protocols, and detailed reports about the subjects involved in clinical experiments.

The Subject Detail Report (FIG. 59) is a detailed summary of each subject at a site including identification, demographics, study details and monitoring. The report also includes information for each of the subject's visits, such as the date of the visit, the number of days outside of the planned visit date, the type of source document verification completed for each visit, and the status of the CRF pages for each visit. It allows the user to review in a snapshot the primary information of the subjects enrolled in a specified site, study, or drug program. This report is helpful to monitors in tracking and reporting to their managers the status of the source document verification and CRF collection at a site. Other potential users would be the Project Physician and site personnel.

If only site level tracking is done, this report will not be available. If subject level tracking without visit level tracking is done, the report will only contain the subject level details.

The report is divided into three sections. The header contains all the necessary information about the protocol which comes from the protocol administration screen and includes the Site No, Study Location and monitor.

The second portion has the subject level details and it prints as a different set for each different subject. It includes all the columns found in the Subject Summary tab of the Subject level Tracking screen of the system, such as Gender of the subject, age, date of birth, signed consent date, evaluation, last visit date, last visit label, therapy start date, end date, number of days on therapy and reason for discontinuation.

The third section of the report gives the visit details of the subject, such as visit label date, which is also known as the delta, and the number of days outside of the planned visit date, the SDV status, CRF status and Pages collected.

Figure 60:
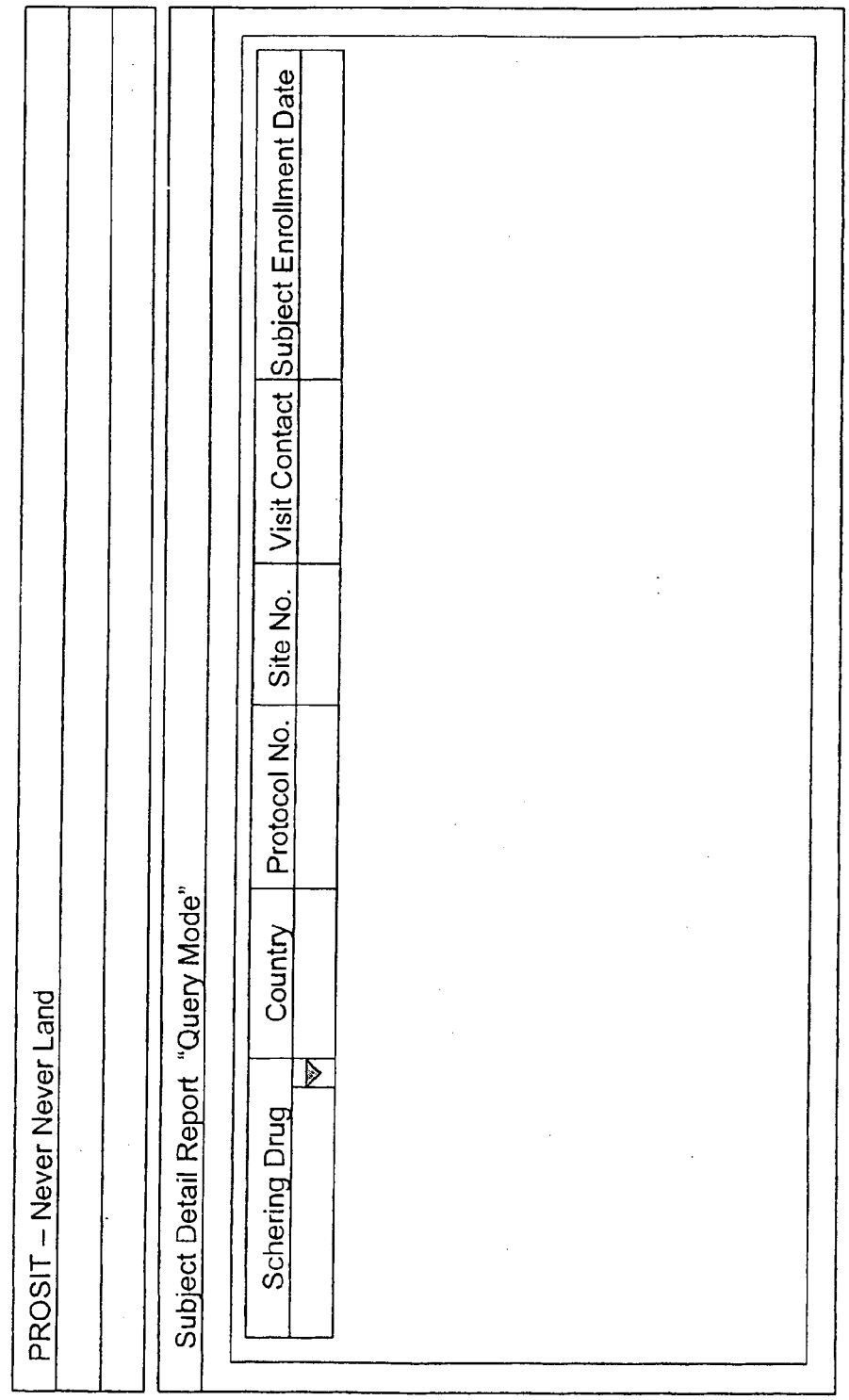
FIG. 60 shows the Reports Query screen of the invention.

To generate this report and others, the user selects Modules—Reports from the menu and then chooses Site/Subject Status—Subject Data. This opens a Query screen (FIG. 60) which is used to extract specific information on which reports will be generated. The column headings are the names of the fields by which the user can filter the data selected. The cells below the column headings allow the user to select the report criteria for extraction.

In order to have data available the user must select a company drug. The drop-down list displays only the company drugs to which the user has access. If the user specifies a Protocol number as a criteria, only the subjects for that Protocol number will be returned. If a site is also selected as a criteria, the user will only see the subjects from that site in that specified protocol.

The Site/Subject Summary report allows the user to retrieve summary information about the subjects used in a study. This report is not as detailed as a Subject Detail report. The information in Site/Subject summary reports is a combination of site tracking and subject tracking data entered in the Site Contact module.

The Site/Subject Summary Report (FIG. 61) is a summary of the site information. The report includes the totals for enrollment, key status markers (such as first enrolled and last enrolled to date), and discontinuation reasons. It also contains basic information on the subjects. This report will display the current status for each subject at a site. The status includes the subject identifiers (screening number, initials, enrollment numbers), the subject's current status in the study, the last visit or phase completed, and the monitoring status of a subject (CRF review and collection status, source document verification). It allows the user to review the primary information of a site participating in a specific study, or using a specific drug. The users of this report are the monitor, manager, Project Physician, the therapeutic area director and the site personnel. This report is an effective tool for monitors and managers to review details regarding all sites at a glance and will be especially helpful when site reassignment or site sharing occurs.

If site level tracking is done, only the site level information and Milestones will be available. If subject-visit level tracking is not being done, the report will contain the subject level details only. If a Milestone date is a latest estimate, instead of an actual one, then it will appear in parenthesis. If a user chooses multiple site selection (e.g. Canada/ Europe, country, monitor sites, etc.), then the report is printed for each site.

The report is divided into three sections. The header contains all the protocol related common information, such as company No., working study title, protocol no./site no., principal investigator, study location and monitor. The second section has the site level details of the report, which again are divided into three categories such as Enrollment Summary, Milestones, Monitoring Summary. The third section has the per Subject Summary of all the details regarding the subjects including the reason for discontinuation, and Therapy start date and end date.

Monitoring Status Reports (FIG. 62) provide the user summary information on the monitoring status at sites. This includes the visits monitored for each subject as well as summary statistics for the site.

It allows the user to review the status of the subjects, the CRF review and correction, and plan monitoring accordingly. It is also a useful tool to verify the rule that 20% of the subjects have had 100% source document verification ("SDV"). It offers also the opportunity to view in a glance the progress of the subjects. It is used by the monitor, manager, project physician, therapeutic area director and site personnel.

This report will be available only if subject-visit level tracking and visit mapping are done. If a user chooses multiple site selections (e.g. Canada/Europe, country, monitor sites, etc.), the Site number is specified in the headings such as Site 1 Summary and Site 1 Details. The entire report with the header, detail and summary are printed first for the first site followed by the next site, etc.

The report is divided into three sections. The first section, which is the header, has all the protocol related information like company No., working title, Protocol number/Site Number, principal investigator, Study Location and monitor. The second section has the Site Summary details like the "as of" date, Contact number, details of the status of the protocol, site and visit details, and also the subjects' details at the site level. The third section of the report deals with the Subject level visit details providing the completed and monitored information for each visit of all the subjects with their identification numbers.

The Site Personnel and Location report (FIG. 63) displays all company employees, non-employees and locations listed by role for the selected site. The report will list address and phone number information for each person and location. It allows the user to create a mailing list of personnel and locations involved in the sites of the study.

Protocol summary reports provide the user with high level protocol information, such as the projected enrollment, medications, study location and external organizations. The Protocol Summary Report is a detailed listing of data related to a protocol and the current status in terms of Milestone dates, enrollment goals, and monitoring requirements. The report also includes key design information, such as the study medications, and external organizations involved in the protocol. The bottom of the report lists the protocol synopsis.

Contact Information Reports (FIG. 64) provide details of the personnel and the locations involved with a particular protocol. The report will list address and phone information for each person and location.

The Protocol Study Plan Report is used to report the study planning projections made for a particular protocol and the details of the tasks carried out and their completions. The header reports the projected number of subjects to enroll and the evaluable subjects. It also reports the number of sites in the US and the number of international sites, as well as the overall protocol status (e.g. whether enrollment is ongoing/ complete or screening is on going on etc.). The detail portion lists all the tasks completed for the particular protocol with their planned, estimated and completed dates.

The Protocol Enrollment—Actual/Plan Summary Report displays both enrollment and milestone plan information for sites within a protocol. The enrollment information displayed compares actual site level data to planned data. The Milestone information shows planned and actual dates for both at the protocol and site level. The report is used by clinical monitors, managers and executives.

The report is divided into four sections, (1) the general protocol information, (2) information related to the creating and enrolling of patients at the protocol sites, (3) detailed information about each of the sites that are participating in the protocol study, and (4) summary information about the sites participating in the study.

The Protocol Enrollment—Site Contact and Subject Level Report displays both enrollment and milestone plan information for sites within a protocol. The enrollment information displayed compares site level data to subject visit level data. The Milestone information shows planned and actual dates at the protocol and site level. The report is used by clinical monitors, managers and executives. It allows users to see how much actual monitoring (site visits) are being done. Each monitor, on average will run the report weekly. The report is divided into four sections: (1) General protocol information; (2) Milestone (protocol study plan) Information related to the creating and enrolling of patients at the protocol sites; (3) Detail information about site level subject data verses subject level subject data for the most recent "As Of" date for most recent contact at each of the sites that are participating in the protocol study; and (4) Summary information about the sites/subjects participating in the study.

The Site Personnel & Locations Information Sheet (FIG. 63) displays all personnel, and locations listed by role for the selected site(s). The report will list address and phone information for each person and location.

The Site Study Plan report establishes the details of the site study tracking module. The report consists of details of the site like the protocol number and the location of the site, etc. It also gives information about the date when the site was initiated, actual number of subjects enrolled in that site and also the last visit date of the last subject. The report is made up of two parts, the header and the detail. The header information is related to both the protocol and the site, whereas the detail data is from the site study tracking module. It consists of the task name, latest estimate and actual completion dates for each task.

This memo is used to get new Payees added to the AP vendor file in Memphis. The memo prints all Global Payees identified in the Country Administration Module that have a status of "submitted".

12. Forms Generation

As noted above the system has the capability of using the data collected and integrated by the software to generate completed forms. While it is common for computer database systems to printout selections of data, with the present invention at least some of the forms are those required by governmental health authorities (e.g. the FDA in the United States) in the conduct of all clinical trials. These forms also allow the Company to maintain compliance with health authority guidelines.

In order to generate the necessary and/or desirable forms, the user clicks on "Forms" on the main menu. (FIG. 65) This provides the following selection of forms that can be generated:

FDA Form 1572
Investigator's Agreement
Investigator Visit
Non-Visit Contact Report
Pre-Study Investigate Visit
Trial Initiation And Authorization (TIA)
SMP Form
Formulated Materials Registration Form
Packaging/Shipping Request Form
Material Transfer Request Form Thus, any of these forms can be created from this menu.

12a. FDA 1572 Form

The system creates the form using information entered within the system as the clinical sites are identified and tracked within the normal flow of business practices. The principal and/or co-principal investigator(s) who plan to conduct studies under an IND must sign an FDA 1572 FORM. This form, issued by the Department of Health and Human Services, Food and Drug Administration, informs the investigator under the "Statement of Investigator" of some of the precepts under which the study is to be conducted and outlines their major responsibilities.

Thus, the system automatically prepares and prints this form using data already in the system. This provides a significant savings in time and assures the accuracy and consistency of the form.

12b. Investigator's Agreement Form

The Investigator's Agreement and Investigator Visit forms allow for easy and uniform dealing with investigators. They can be modified by the System Administrator based on the advice of legal counsel to be suitable for use in various geographical regions.

12c. Investigator Visit and Non-Visit Contact Forms

After information has been entered and finalized (using the Action menu) as to a Site Contact or a Non-Visit Contact Report can be printed. It will use the information entered as described for contact and non-contact visits. Those forms are typically required by health authority guidelines.

12d. Pre-Study Visit Forms

One requirement is the documentation of a pre-study visit to a site where a clinical trial may be conducted to judge the facilities and the capabilities of the principal investigator at that site. Once the pre-visit report has been completed as set forth above, the user can print this form.

12e. Trial Initiation Form (TIA)

The system creates the Trial Initiation Form, internal compliance form, by using planning and tracking information within the normal flow of business practices. In an effort to achieve uniformity in the procedures governing the release, shipment, and delivery of clinical supplies for both domestic and international investigational sites, the TIA form is designed for international studies. This form serves as a checklist, transmittal and acknowledgment document. All required pre-study documents must be obtained and sent to the Company main office with the completed TIA form from the system.

12f. Study Management Plan (SMP)

The Study Management Plan (SMP) for international studies is shown in FIG. 25 and was discussed above. The forms menu allows this document to be printed.

12g. Clinical Supplies Forms

The Formulated Materials Request Form, Packaging/Shipping Request Form and the Material Transfer Request Form were discussed above in connection with the Clinical Supplies module.

Thus the system allows for the creation of required forms (e.g. FDA 1572) as well as convenient forms (e.g. Investigator Agreement) based on information already in the system.

While the present invention has been particularly shown and described with reference to a preferred embodiment thereof, it will be understood by those skilled in the art that various changes in form and details may be made therein without departing from the spirit and scope of the invention.

We claim:

1. A clinical trial management system comprising:
a main database of information concerning prior clinical trials and resources available to conduct future clinical trials, the information concerning prior clinical trials being at least in part in the form of a protocol of (a) scheduled visits of a test subject to a treatment site, (b) measurement of prescribed physical attributes of the subject during the visits and (c) administration of at least one prescribed medical product to the subject during the visit to determine over time the subject's response thereto, the protocol of a prior clinical trial being stored in said main database in the form of a software template;
a main processor controlling access to said main database; and
at least one user processor in communication with said main processor to negotiate access to said main database, said user processor and main processor running a program that designs and tracks at said user processor of a clinical trial through access by said user processor to at least one software template in said main database and modification of the template for formulating a new clinical trial.

2. The clinical trial management system of claim 1 further comprising:
a subsidiary database;
a subsidiary processor controlling access to said subsidiary database, said subsidiary processor being in communication with said main processor to controlling replication of a portion of the data in the main database to said subsidiary database;
at least one subsidiary user processor in communication with said subsidiary processor, said subsidiary processor and subsidiary user processor running the program so as to permit the design and tracking at said subsidiary user processor of a clinical trial based on data in said subsidiary database.

3. The clinical trial management system of claim 2, wherein said subsidiary processor, subsidiary database and subsidiary user processor are located in a certain geographical location remote from the location of said main database and said main processor; and wherein the portion of data replicated to said subsidiary database relates to clinical trials in said certain geographical location.

4. The clinical trial management system of claim 3 wherein the portion of data in said subsidiary database includes at least one template of a clinical trial protocol previously created according to requirements prevalent in the certain geographical location.

5. The clinical trial management system of claim 3, wherein the portion of data in said subsidiary database can be altered by said subsidiary user processor and the data in the main database can be altered by said user processor; and wherein said main processor and said subsidiary processor periodically operate to synchronize the replicated and changed data at said main database and said subsidiary database, with changes at said main database predominating over changes at said subsidiary database.

6. The clinical trial management system of claim 3 wherein the program includes a site management module for indicating the conditions at the certain geographical location, including the portion of any protocol to be carried out in that geographical location.

7. The clinical trial management system of claim 6 wherein information about the completion of tasks in the protocol at the certain geographical location are entered by the subsidiary user processor in the subsidiary database, and the site management nodule updates the portion of the protocol related thereto.

8. The clinical trial management system of claim 1 wherein said main processor and main database are in an organizational environment which includes other databases with specialized information useful in formulating clinical trials; and further including a communications link with said other databases and means for replicating selected portions of the data in the other databases into the main database.

9. The clinical trial management system of claim 8 wherein the other databases are one of a human resources database of personnel and location information, a finance database of budget authorization and cost information and a clinical supplies database of information on the availability of various clinical medical products.

10. The clinical trial management system of claim 1 further including a display at the user processor which is operative to display the clinical trial protocol as a list of visits in sequence that form the protocol, with minor tasks that make up a major task indented under the major task.

11. The clinical trial management system of claim 10 wherein said users processor can used to input information concerning completion of tasks in the protocol, and the display is updated to show progress of the trial.

12. The clinical trial management system of claim 11 wherein the program automatically indicates the completion of a major task when all of its minor related tasks are completed.

13. The clinical trial management system of claim 1 wherein the program is in the form of modules.

14. The clinical trial management system of claim 13 wherein the program includes a reports module that generates reports of the status of the trial for presentation on the display.

15. The clinical trial management system of claim 13 wherein the program includes a reports module that generates messages to personnel concerning actions to take to advance the trial.

16. The clinical trial management system of claim 15 wherein at least one of the messages is to a provider of clinical supplies for the trial to inform it of the medical products needed for the trial.

17. The clinical trial management system of claim 1 further including a portable processor running the program, said portable processor operating with said main processor to transfer to the portable processor a copy of a portion of the main database related to a site for the clinical trial in a certain geographical area, said main processor locking the portion of the main database that was copied said portable processor receiving information about the completion of tasks in the protocol at the certain geographical area and modifying the copy as a result thereof, and said portable processor operating with said main processor to transfer to and update the main database with the modified copy of the data and to unlock that portion of the main database.

18. A clinical trial management system comprising:

a main database of information concerning resources available to conduct clinical trials;

a main processor controlling access to said main database;

at least one user processor in direct communication with said main processor to negotiate access to said main database, said user processor and main processor running a program that designs a clinical trial in the form of a protocol of tasks to be completed and tracks the completion of the tasks in the protocol at said user processor;

a subsidiary database;

a subsidiary processor controlling access to said subsidiary database, said subsidiary processor being in communication with said main processor to controlling replication of a portion of the data in the main database to said subsidiary database;

at least one subsidiary user processor in communication with said subsidiary processor, said subsidiary processor and subsidiary user processor running the program so as to design and track at said subsidiary user processor a protocol based on data in said subsidiary database.

19. The clinical trial management system of claim 18, wherein said subsidiary processor, subsidiary database and subsidiary user processor are located in a certain geographical location remote from the location of said main database and said main processor; and wherein the portion of data replicated to said subsidiary database relates to clinical trials in said certain geographical location.

20. The clinical trial management system of claim 19 wherein the portion of data in said subsidiary database includes at least one template of a clinical trial protocol previously created according to requirements prevalent in the certain geographical location.

21. The clinical trial management system of claim 19, wherein the portion of data in said subsidiary database can be altered by said subsidiary user processor and the data in the main database can be altered by said user processor, and wherein said main processor and said subsidiary processor periodically operate to synchronize the replicated and changed data at said main database and said subsidiary database, with changes at said main database predominating over changes at said subsidiary database.

22. The clinical trial management system of claim 18 wherein said main processor and main database are in an organizational environment which includes other databases with specialized information useful in formulating clinical trials; and further including a communications link with said other databases and means for replicating selected portions of the data in the other databases into the main database.

23. The clinical trial management system of claim 22 wherein the other databases are one of a human resources database of personnel and location information, a finance database of budget authorization and cost information and a clinical supplies database of information on the availability of various clinical medical products.

24. The clinical trial management system of claim 18 further including displays at the user processor and subsidiary user processor which are operative to display the clinical trial protocol as a list of visits in sequence that form the protocol, with minor tasks that make up a major task indented under the major task.

25. The clinical trial management system of claim 24 wherein said user processors and subsidiary user processors can used to input information concerning completion of tasks in the protocol, and the display is updated to show progress of the trial.

26. The clinical trial management system of claim 25 wherein the program automatically indicates the completion of a major task when all of its minor related tasks are completed.

27. The clinical trial management system of claim 26 wherein the program includes a reports module that generates reports of the status of the trial for presentation on the display.

28. The clinical trial management system of claim 27 wherein at least one of the messages is to a provider of clinical supplies for the trial to inform it of the medical products needed for the trial.

29. The clinical trial management system of claim 26 wherein the program includes a reports module that generates messages to personnel concerning actions to take to advance the trial.

30. The clinical trial management system of claim 18 wherein the program is in the form of modules.

31. The clinical trial management system of claim 18 wherein the program running on said subsidiary user processor includes a site management module for indicating the conditions at the certain geographical location, including the portion of any protocol to be carried out in that geographical location.

32. The clinical trial management system of claim 31 wherein information about the completion of tasks in the protocol at the certain geographical location are entered by the subsidiary user processor in the subsidiary database, and the site management module updates the portion of the protocol related thereto.

33. The clinical trial management system of claim 18 further including a portable processor running the program, said portable processor operating with said main processor to transfer to the portable processor a copy of a portion of the main database related to a site for the clinical trial in a certain geographical area, said main processor locking the portion of the main database that was copied, said portable processor receiving information about the completion of tasks in the protocol at the certain geographical area and modifying the copy as a result thereof, and said portable processor operating with said main processor to transfer to and update the main database with the modified copy of the data and to unlock that portion of the main database.

34. The clinical trial management system of claim 18 wherein there are a plurality of user processors located at different clinical trial sites in the geographical area in which the main processor and main database are located.

35. The clinical trial management system of claim 18 wherein there are a plurality of subsidiary processors and subsidiary databases each located in respective geographical areas that are different from the geographical area in which the main processor and main database are located.

36. The clinical trial management system of claim 35 wherein there are a plurality of subsidiary user processors located in each geographical area in which a subsidiary processor and subsidiary database are located, said plurality of subsidiary user processors being connected to the subsidiary processor in their respective geographical area.

37. The clinical trial management system of claim 36 in which the geographical areas are countries.

38. The clinical trial management system of claim 18 wherein the system manages a plurality of clinical trials with separate protocols, at least some of the separate protocols having major tasks made up of a plurality of minor tasks that are common to them, and wherein the program automatically indicates the completion of a common major task in the separate protocols when all of the minor related tasks are completed.

39. A clinical trial management system comprising:
a main database of information concerning resources available to conduct clinical trials;
a main processor controlling access to said main database;
at least one user processor in direct communication with said main processor to negotiate access to said main database, said user processor and main processor running a program that designs a clinical trial and the input of information with regard to the completion of tasks forming a protocol for the clinical trial and tracks the completion of the tasks at said user processor, a portion of said program printing forms determined by the data in the system.

40. The clinical trial management system of claim 39,
further including a subsidiary processor, subsidiary database and subsidiary user processor located in a certain geographical location remote from the location of said main database and said main processor; and
wherein a portion of data in the main database is replicated to said subsidiary database and relates to clinical trials in said certain geographical location.

* * * * *